US009070272B2

(12) United States Patent
Gettings et al.

(10) Patent No.: US 9,070,272 B2
(45) Date of Patent: Jun. 30, 2015

(54) ELECTRONIC DEVICE WITH ENVIRONMENTAL MONITORING

(71) Applicant: Leeo, Inc., Palo Alto, CA (US)

(72) Inventors: Adam Matthew Gettings, Red Wing, MN (US); Andrew Gettings Stevens, Palo Alto, CA (US); Bjorn Hovland, Woodside, CA (US)

(73) Assignee: Leeo, Inc., Palo Alto, CA (US)

( * ) Notice: Subject to any disclaimer, the term of this patent is extended or adjusted under 35 U.S.C. 154(b) by 0 days.

(21) Appl. No.: 14/283,057

(22) Filed: May 20, 2014

(65) Prior Publication Data

US 2015/0020614 A1    Jan. 22, 2015

Related U.S. Application Data

(60) Provisional application No. 61/847,079, filed on Jul. 16, 2013, provisional application No. 61/847,555, filed on Jul. 17, 2013, provisional application No. 61/858,563, filed on Jul. 25, 2013.

(51) Int. Cl.
*G08B 17/10*    (2006.01)
*G01N 21/84*    (2006.01)
(Continued)

(52) U.S. Cl.
CPC ............... *G08B 21/18* (2013.01); *G01N 21/84* (2013.01); *G01D 7/00* (2013.01); *G01N 33/00* (2013.01);
(Continued)

(58) Field of Classification Search
CPC . G01N 1/2226; G01N 1/2247; G01N 1/2258; G01N 1/2273; G01N 15/06; G01N 21/35; G01N 21/53; G01N 21/783; G01N 21/3504; G01N 33/0031; G01N 33/497; G01N 2001/022; G01N 2001/245; G01N 2001/2223
See application file for complete search history.

(56) References Cited

U.S. PATENT DOCUMENTS 4,093,867 A *   6/1978   Shah et al. .................... 250/576
4,418,333 A      11/1983   Schwarzbach et al.
(Continued)

FOREIGN PATENT DOCUMENTS

EP      1500955      1/2005
GB      2454731      5/2009
(Continued)

OTHER PUBLICATIONS

Carriazo-Osorio, Fernando, "Impacts of Air Pollution on Property Values: an Economic Valuation for Bogota, Colombia", http://www.demogr.mpg.de/papers/workshops/01 0518yaper02.pdf, Aug. 19, 2007.

(Continued)

*Primary Examiner* — David A Rogers

(57) ABSTRACT

An environmental monitoring device that includes a sensor mechanism is described. During operation of the environmental monitoring device, heat generated by a processor in the environmental monitoring device may result in a convective fluid flow over the sensor mechanism that facilitates measurements of sensor data associated with an environmental condition in an external environment that includes the environmental monitoring device. Alternatively, a fluid driver (such as a fan) associated with the processor may produce the fluid flow over the sensor mechanism. Note that the fluid flow may include an airflow and/or a liquid flow. Moreover, the environmental monitoring device may include baffles that direct the fluid flow over a selected sensor in a set of sensors in the sensor mechanism.

19 Claims, 29 Drawing Sheets

(51) Int. Cl.
*G08B 21/18* (2006.01)
*G01D 7/00* (2006.01)
*G01N 33/00* (2006.01)
*G01J 1/04* (2006.01)
*G01J 1/42* (2006.01)
*G08B 13/02* (2006.01)
*H01R 13/62* (2006.01)
*H01R 13/627* (2006.01)
*G08B 29/18* (2006.01)
*G08B 3/00* (2006.01)

(52) U.S. Cl.
CPC .............. *G01J 1/0437* (2013.01); *G01J 1/42* (2013.01); *G08B 13/02* (2013.01); *H01R 13/6205* (2013.01); *H01R 13/627* (2013.01); *G08B 17/10* (2013.01); *G08B 29/181* (2013.01); *G08B 3/00* (2013.01)

(56) References Cited

U.S. PATENT DOCUMENTS

| | | | |
|---|---|---|---|
| 4,450,436 A | 5/1984 | Massa | |
| 4,896,039 A | 1/1990 | Fraden | |
| 5,045,833 A | 9/1991 | Smith | |
| 5,156,203 A | 10/1992 | Funakoshi et al. | |
| 5,159,315 A | 10/1992 | Schultz et al. | |
| 5,532,660 A | 7/1996 | Smith et al. | |
| 5,646,591 A | 7/1997 | Issa et al. | |
| 5,675,070 A * | 10/1997 | Gelperin ..................... | 73/23.34 |
| 5,801,297 A * | 9/1998 | Mifsud et al. ............... | 73/23.34 |
| 6,023,223 A | 2/2000 | Baxter, Jr. | |
| 6,216,956 B1 | 4/2001 | Ehlers et al. | |
| 6,415,205 B1 | 7/2002 | Myron et al. | |
| 6,428,334 B1 | 8/2002 | Skarie et al. | |
| 6,492,907 B1 | 12/2002 | McCracken | |
| 6,672,129 B1 * | 1/2004 | Frederickson et al. ......... | 73/1.06 |
| 6,753,776 B2 | 6/2004 | Drinkard | |
| 6,753,786 B1 | 6/2004 | Apperson et al. | |
| 6,759,763 B2 | 7/2004 | Barton | |
| 7,089,780 B2 * | 8/2006 | Sunshine et al. .............. | 73/23.2 |
| 7,098,782 B1 | 8/2006 | Peckham et al. | |
| 7,116,213 B2 | 10/2006 | Thiesen et al. | |
| 7,257,397 B2 | 8/2007 | Shamoon et al. | |
| 7,304,259 B2 * | 12/2007 | Schwarz et al. ............... | 209/584 |
| 7,337,078 B2 | 2/2008 | Bond et al. | |
| RE40,437 E | 7/2008 | Rosen | |
| 7,400,594 B2 | 7/2008 | Pereira et al. | |
| 7,515,041 B2 | 4/2009 | Eisold et al. | |
| 7,522,036 B1 | 4/2009 | Preuss et al. | |
| 7,764,180 B2 | 7/2010 | Huang | |
| 7,784,293 B2 | 8/2010 | Violand et al. | |
| 7,818,184 B2 | 10/2010 | Penny et al. | |
| 7,825,546 B2 | 11/2010 | Li et al. | |
| 7,905,154 B2 * | 3/2011 | Jones, Jr. ..................... | 73/864.81 |
| 7,952,475 B2 | 5/2011 | Ivanov et al. | |
| 7,994,928 B2 | 8/2011 | Richmond | |
| 8,113,069 B2 * | 2/2012 | Settles ........................ | 73/864.35 |
| 8,125,194 B2 | 2/2012 | Nethken | |
| 8,170,722 B1 | 5/2012 | Elberbaum | |
| 8,224,576 B2 | 7/2012 | Jensen et al. | |
| 8,242,640 B2 | 8/2012 | Lee et al. | |
| 8,289,135 B2 | 10/2012 | Griffin | |
| 8,301,271 B2 | 10/2012 | Lee et al. | |
| 8,335,936 B2 | 12/2012 | Jonsson et al. | |
| 8,451,132 B1 | 5/2013 | Van Vleet | |
| 8,475,367 B1 | 7/2013 | Yuen et al. | |
| 8,489,437 B1 | 7/2013 | Dlott et al. | |
| 8,605,091 B2 | 12/2013 | Bradbury et al. | |
| 8,610,587 B2 | 12/2013 | Tropper | |
| 8,639,391 B1 | 1/2014 | Alberth, Jr. et al. | |
| 8,683,236 B2 | 3/2014 | Ukita et al. | |
| 2001/0007800 A1 | 7/2001 | Skarie et al. | |
| 2002/0011947 A1 | 1/2002 | Stolarczyk | |
| 2002/0050932 A1 | 5/2002 | Rhoades et al. | |
| 2002/0069076 A1 | 6/2002 | Faris et al. | |
| 2002/0097546 A1 | 7/2002 | Weinberger | |
| 2002/0152037 A1 * | 10/2002 | Sunshine et al. ................ | 702/23 |
| 2003/0074092 A1 | 4/2003 | Carrabis | |
| 2003/0227220 A1 | 12/2003 | Biskup et al. | |
| 2004/0025604 A1 * | 2/2004 | Call et al. .................... | 73/863.22 |
| 2004/0069046 A1 * | 4/2004 | Sunshine et al. .............. | 73/23.34 |
| 2004/0075566 A1 | 4/2004 | Stepanik et al. | |
| 2004/0147038 A1 * | 7/2004 | Lewis et al. ................... | 436/149 |
| 2004/0158193 A1 | 8/2004 | Bui et al. | |
| 2005/0136972 A1 | 6/2005 | Smith et al. | |
| 2005/0148890 A1 | 7/2005 | Hastings | |
| 2005/0229452 A1 | 10/2005 | Shimasaki | |
| 2006/0004492 A1 | 1/2006 | Terlson et al. | |
| 2006/0173580 A1 | 8/2006 | Desrochers et al. | |
| 2006/0250236 A1 | 11/2006 | Ackley et al. | |
| 2006/0250260 A1 | 11/2006 | Albert et al. | |
| 2007/0038334 A1 | 2/2007 | Chou et al. | |
| 2007/0061393 A1 | 3/2007 | Moore | |
| 2007/0155349 A1 | 7/2007 | Nelson et al. | |
| 2007/0168088 A1 | 7/2007 | Ewing et al. | |
| 2007/0173978 A1 | 7/2007 | Fein et al. | |
| 2007/0225868 A1 | 9/2007 | Terlson et al. | |
| 2007/0241615 A1 | 10/2007 | Goodrich | |
| 2007/0276548 A1 | 11/2007 | Uzunovic et al. | |
| 2007/0278285 A1 | 12/2007 | Ehrensvaerd | |
| 2008/0024089 A1 | 1/2008 | Meng et al. | |
| 2008/0097809 A1 | 4/2008 | Stroman et al. | |
| 2008/0106424 A1 | 5/2008 | Bouse | |
| 2008/0173817 A1 * | 7/2008 | Goldstein et al. .......... | 250/338.1 |
| 2008/0211683 A1 | 9/2008 | Curt et al. | |
| 2008/0221714 A1 | 9/2008 | Schoettle | |
| 2008/0291036 A1 | 11/2008 | Richmond | |
| 2009/0054770 A1 * | 2/2009 | Vrtis et al. ..................... | 600/532 |
| 2009/0066513 A1 | 3/2009 | Kondo et al. | |
| 2009/0096620 A1 | 4/2009 | Kuo | |
| 2009/0141898 A1 | 6/2009 | Huang | |
| 2009/0157839 A1 | 6/2009 | Diederichs et al. | |
| 2009/0193578 A1 | 8/2009 | Jang et al. | |
| 2009/0195382 A1 | 8/2009 | Hall | |
| 2009/0225480 A1 | 9/2009 | Baxter | |
| 2009/0271013 A1 | 10/2009 | Chen | |
| 2009/0278868 A1 | 11/2009 | Nakahira et al. | |
| 2010/0025449 A1 | 2/2010 | Longobardi | |
| 2010/0090822 A1 | 4/2010 | Benson et al. | |
| 2010/0101264 A1 | 4/2010 | Nishino | |
| 2010/0145543 A1 | 6/2010 | Middlemiss | |
| 2010/0164742 A1 | 7/2010 | Anderson | |
| 2010/0235004 A1 | 9/2010 | Thind | |
| 2010/0249955 A1 | 9/2010 | Sitton | |
| 2010/0298957 A1 | 11/2010 | Sanchez Rocha et al. | |
| 2010/0306033 A1 | 12/2010 | Oved et al. | |
| 2010/0313748 A1 | 12/2010 | Schluter | |
| 2010/0318236 A1 | 12/2010 | Kilborn et al. | |
| 2011/0025499 A1 | 2/2011 | Hoy et al. | |
| 2011/0027626 A1 | 2/2011 | Lattin | |
| 2011/0108724 A1 * | 5/2011 | Ewing et al. ................... | 250/282 |
| 2011/0187542 A1 | 8/2011 | Dittmer et al. | |
| 2011/0202193 A1 | 8/2011 | Craig et al. | |
| 2011/0216453 A1 | 9/2011 | Haines et al. | |
| 2011/0245988 A1 | 10/2011 | Ingels et al. | |
| 2011/0260851 A1 | 10/2011 | Richman | |
| 2011/0270458 A1 | 11/2011 | Liu | |
| 2011/0273283 A1 | 11/2011 | Schmuttor et al. | |
| 2011/0316355 A1 | 12/2011 | Gruber et al. | |
| 2012/0022886 A1 | 1/2012 | Ohnemus | |
| 2012/0023555 A1 | 1/2012 | Putterman | |
| 2012/0095610 A1 | 4/2012 | Chapel et al. | |
| 2012/0109398 A1 | 5/2012 | Bhakta | |
| 2012/0130544 A1 | 5/2012 | Mohan et al. | |
| 2012/0154126 A1 | 6/2012 | Cohn et al. | |
| 2012/0209634 A1 | 8/2012 | Ling et al. | |
| 2012/0265361 A1 | 10/2012 | Billingsley et al. | |
| 2012/0303554 A1 | 11/2012 | Osann | |
| 2012/0316661 A1 | 12/2012 | Rahman et al. | |
| 2012/0325023 A1 * | 12/2012 | Calio et al. ................. | 73/863.02 |
| 2013/0006436 A1 | 1/2013 | Masters et al. | |
| 2013/0038470 A1 | 2/2013 | Niemeyer et al. | |
| 2013/0049466 A1 | 2/2013 | Adams | |

(56) References Cited

U.S. PATENT DOCUMENTS

| | | |
|---|---|---|
| 2013/0082817 A1 | 4/2013 | Gruenbacher et al. |
| 2013/0083805 A1 | 4/2013 | Lu et al. |
| 2013/0085609 A1 | 4/2013 | Barker |
| 2013/0166089 A1 | 6/2013 | Craig et al. |
| 2013/0174646 A1 | 7/2013 | Martin |
| 2013/0184880 A1 | 7/2013 | McMahon |
| 2013/0201033 A1 | 8/2013 | Cohn et al. |
| 2013/0238153 A1 | 9/2013 | Warwick et al. |
| 2013/0275148 A1 | 10/2013 | Attaluri et al. |
| 2013/0289919 A1 | 10/2013 | Wilson et al. |
| 2013/0338839 A1 | 12/2013 | Rogers et al. |
| 2013/0339766 A1 | 12/2013 | Chen et al. |
| 2014/0006506 A1 | 1/2014 | Frei et al. |
| 2014/0025221 A1 | 1/2014 | Chapel et al. |
| 2014/0028097 A1 | 1/2014 | Augur |
| 2014/0032003 A1 | 1/2014 | Chapel et al. |
| 2014/0046599 A1 | 2/2014 | Smith et al. |
| 2014/0069131 A1 | 3/2014 | Masui |
| 2014/0092765 A1 | 4/2014 | Agarwal |
| 2014/0098445 A1 | 4/2014 | Hooper |
| 2014/0099941 A1 | 4/2014 | Ji et al. |
| 2014/0100700 A1 | 4/2014 | Matsumoto et al. |
| 2014/0156084 A1 | 6/2014 | Rahman et al. |
| 2014/0188286 A1 | 7/2014 | Hunka |
| 2014/0236372 A1 | 8/2014 | Ewing et al. |
| 2014/0257572 A1 | 9/2014 | Mohan et al. |
| 2014/0277869 A1 | 9/2014 | King et al. |

FOREIGN PATENT DOCUMENTS

| | | |
|---|---|---|
| WO | WO 2005/063006 | 7/2005 |
| WO | WO 2007/148299 | 12/2007 |

OTHER PUBLICATIONS

Hayashi et al., "A Network-Centric Approach to Sensor-data and Service Integration," Sep. 13-18, 2011, SICE Annual Conference, pp. 2037-2042.

Huang et al., "Pervasive, Secure Access to a Hierarchical Sensor-Based Healthcare Monitoring Architecture in Wireless Heterogeneous Networks," May 4, 2009, IEEE Journal on Selected Areas in Communications, vol. 27, No. 4, pp. 400-411.

Miyaho et al., "Sensor Network Management for Healthcare Applications," 2010, IEEE Computer Society, pp. 14-20.

"Consumer Safety Notice for Nest Protect: Smoke + CO Alarm," nest.com/letter-from-the-ceo/, May 22, 2014.

"Definition of Symptom," http://www.merriam-webster.com/medical/symptom, Apr. 23, 2009.

"For $129, the best smoke detector on the market," CNET, http://www.cnet.com/product/nest-protect/, Jul. 8, 2014.

"Guidance Regarding Methods for De-identification of Protected Health Information in Accordance with the Health Insurance Portability and Accountability Act (HIPAA) Privacy Rule," Department of Health and Human Services, http://www.hhs.gov/ocr/privacy/hipaa/understanding/coveredentities/De-identification/guidance.html, Dec. 1, 2012.

"Nest Labs Recalls to Repair Nest Protect Smoke + CO Alarms Due to Failure to Sound Alert," http://www.cpsc.gov/en/Recalls/2014/Nest-Labs-Recalls-to-Repair-Nest-Protect-Smoke-CO-Alarms/, May 21, 2014.

"Privacy Protector: 6 Good Reasons to De-Identify Data," http://privacyguidance.com/blog/6-good-reasons-to-de-identify-data/, Mar. 2012.

"What is Nest Wave and how does it work?," support.nest.com/article/what-is-nest-wave-and-how-does-it-work/, Apr. 4, 2014.

Brown, Rick, "Nest pulls Protect smoke detector from retail on safety issue," CNET, www.cnet.com, Apr. 3, 2014.

Chapter Five Global Positioning System, Jul. 1, 2008.

Internet Archive Way Back Machine Date confirmation for reference, Chapter Five Global Positioning System, Jul. 1, 2008.

McCracken, Harry, "Nest's Smoke Detector 'Recall' Doesn't Mean You Need to Send Yours Back," Tech Technologizer, www.time.com, May 21, 2014.

Mogg, Trevor, "Nest Recalls 440,000 Protect Smoke Alarms, Issues Software Update That Fixes Glitch," www.digital trends.com. May 21, 2014.

Nest Protect, Manual, Oct. 2013.

Noh et al., "Design of a Room Monitoring System for Wireless Sensor Networks", Jul. 2013, pp. 1-7.

* cited by examiner

ELECTRONIC DEVICE WITH ENVIRONMENTAL MONITORING

CROSS REFERENCE TO RELATED APPLICATION

This application claims priority under 35 U.S.C. §119(e) to: U.S. Provisional Application Ser. No. 61/847,079, entitled "Lighting Device with Environmental Monitoring System," by Adam M. Gettings, Eddy Y. Chan, Andrew G. Stevens, and Bjorn H. Hovland, filed on Jul. 16, 2013; U.S. Provisional Application Ser. No. 61/847,555, entitled "Safety Detector with Environmental Monitoring System," by Adam M. Gettings, Eddy Y. Chan, Andrew G. Stevens, and Bjorn H. Hovland, filed on Jul. 17, 2013; and U.S. Provisional Application Ser. No. 61/858,563, entitled "Switch with Environmental Monitoring System," by Adam M. Gettings. Eddy Y. Chan, Andrew G. Stevens, and Bjorn H. Hovland, filed on Jul. 25, 2013, the contents of all of which are herein incorporated by reference.

BACKGROUND

1. Field

The described embodiments relate generally to an environmental monitoring device, and more specifically to techniques for monitoring environmental conditions in an environment and accordingly modifying operation of the environmental monitoring device.

2. Related Art

Trends in connectivity and in portable electronic devices are resulting in dramatic changes in people's lives. For example, the Internet now allows individuals access to vast amounts of information, as well as the ability to identify and interact with individuals, organizations and companies around the world. This has resulted in a significant increase in online financial transactions (which are sometimes referred to as 'ecommerce'). Similarly, the increasingly powerful computing and communication capabilities of portable electronic device (such as smartphones), as well as a large and growing set of applications, are accelerating these changes, providing individuals access to information at arbitrary locations and the ability to leverage this information to perform a wide variety of tasks.

Recently, it has been proposed these capabilities be included in other electronic devices that are located throughout our environments, including those that people interact with infrequently. In the so-called 'Internet of things,' it has been proposed that future versions of these so-called 'background' electronic devices be outfitted with more powerful computing capabilities and networking subsystems to facilitate wired or wireless communication. For example, the background electronic devices may include: a cellular network interface (LTE, etc.), a wireless local area network interface (e.g., a wireless network such as described in the Institute of Electrical and Electronics Engineers (IEEE) 802.11 standard or Bluetooth™ from the Bluetooth Special Interest Group of Kirkland, Wash.), and/or another type of wireless interface (such as a near-field-communication interface). These capabilities may allow the background electronic devices to be integrated into information networks, thereby further transforming people's lives.

However, the overwhelming majority of the existing background electronic devices in people's homes, offices and vehicles have neither enhanced computing capabilities (such as processor that can execute a wide variety of applications) nor networking subsystems. Given the economics of many market segments (such as the consumer market segment), these so-called 'legacy' background electronic devices (which are sometimes referred to as 'legacy electronic devices') are unlikely to be rapidly replaced. These barriers to entry and change are obstacles to widely implementing the Internet of things.

Furthermore, there remain many environments (such as the interiors of trucks, trains, boxes, etc.) that currently do not regularly include electronic devices. As a consequence, it may also be difficult to extend the advantages of connectivity and enhanced computing capabilities into these environments.

In addition, many of the existing background electronic devices used in people's homes, offices and vehicles are difficult to use. For example, it is often challenging to replace a battery or to modify the functions of these existing background electronic devices.

Hence, there is a need for an environmental monitoring device that addresses the above-described problems.

SUMMARY

The described embodiments relate to an environmental monitoring device that includes a housing having walls that define a cavity within the housing, and flow vents in at least one of the walls that, during operation of the environmental monitoring device, direct a fluid flow into and out of the cavity. Moreover, the environmental monitoring device includes a sensor mechanism, within the cavity, that provides sensor data based on measurements of an environmental condition in an external environment that includes the environmental monitoring device. Furthermore, the environmental monitoring device includes a processor, within the cavity, that processes the sensor data. The fluid flow is associated with operation of the processor, and the processor is positioned relative to the sensor mechanism so that the fluid flow is directed over the sensor mechanism to facilitate the measurements.

In some embodiments, the fluid flow includes a convective fluid flow associated with heat generated during operation of the processor. Alternatively or additionally, the environmental monitoring device may include a fluid driver, and, during operation of the processor, the fluid driver may force the fluid flow into and out of the cavity.

Note that the fluid flow may include an airflow and the fluid driver may include a fan. Alternatively, the fluid flow may include a liquid flow and the fluid driver may include a pump. Thus, the fluid flow may include: an airflow, and a liquid flow.

Moreover, the sensor mechanism may include: an air-quality sensor, a particle counter, and/or a volatile-organic-compound sensor.

In some embodiments, the sensor mechanism includes a set of sensors, and the environmental monitoring device includes a baffle that directs the fluid flow over a selected sensor in the set of sensors. For example, an orientation of the baffle may change in response to an external force applied to the baffle. Alternatively or additionally, the environmental monitoring device may include a steering mechanism that changes an orientation of the baffle based on the selected sensor. In particular, the control mechanism may provide an output signal to the steering mechanism based on the selected sensor, and the output signal may specify the selected sensor.

Another embodiment provides a computer-program product for use in conjunction with the environmental monitoring device. This computer-program product may include instructions for at least some of the aforementioned operations performed by the environmental monitoring device.

Another embodiment provides a method for processing the sensor data, which may be performed by the processor in the environmental monitoring device. During operation, the processor generates the fluid flow over the sensor mechanism in the environmental monitoring device, where the fluid flow is associated with operation of the processor, and where the processor is positioned relative to the sensor mechanism so that the fluid flow is directed over the sensor mechanism to facilitate measurements. Then, the processor receives the sensor data from the sensor mechanism based on the measurements of the environmental condition in the external environment that includes the environmental monitoring device. Next, the processor processes the sensor data.

The preceding summary is provided as an overview of some exemplary embodiments and to provide a basic understanding of aspects of the subject matter described herein. Accordingly, the above-described features are merely examples and should not be construed as narrowing the scope or spirit of the subject matter described herein in any way. Other features, aspects, and advantages of the subject matter described herein will become apparent from the following Detailed Description, Figures, and Claims.

BRIEF DESCRIPTION OF THE FIGURES

Note that like reference numerals refer to corresponding parts throughout the drawings. Moreover, multiple instances of the same part are designated by a common prefix separated from an instance number by a dash.

DETAILED DESCRIPTION

Figure 1:
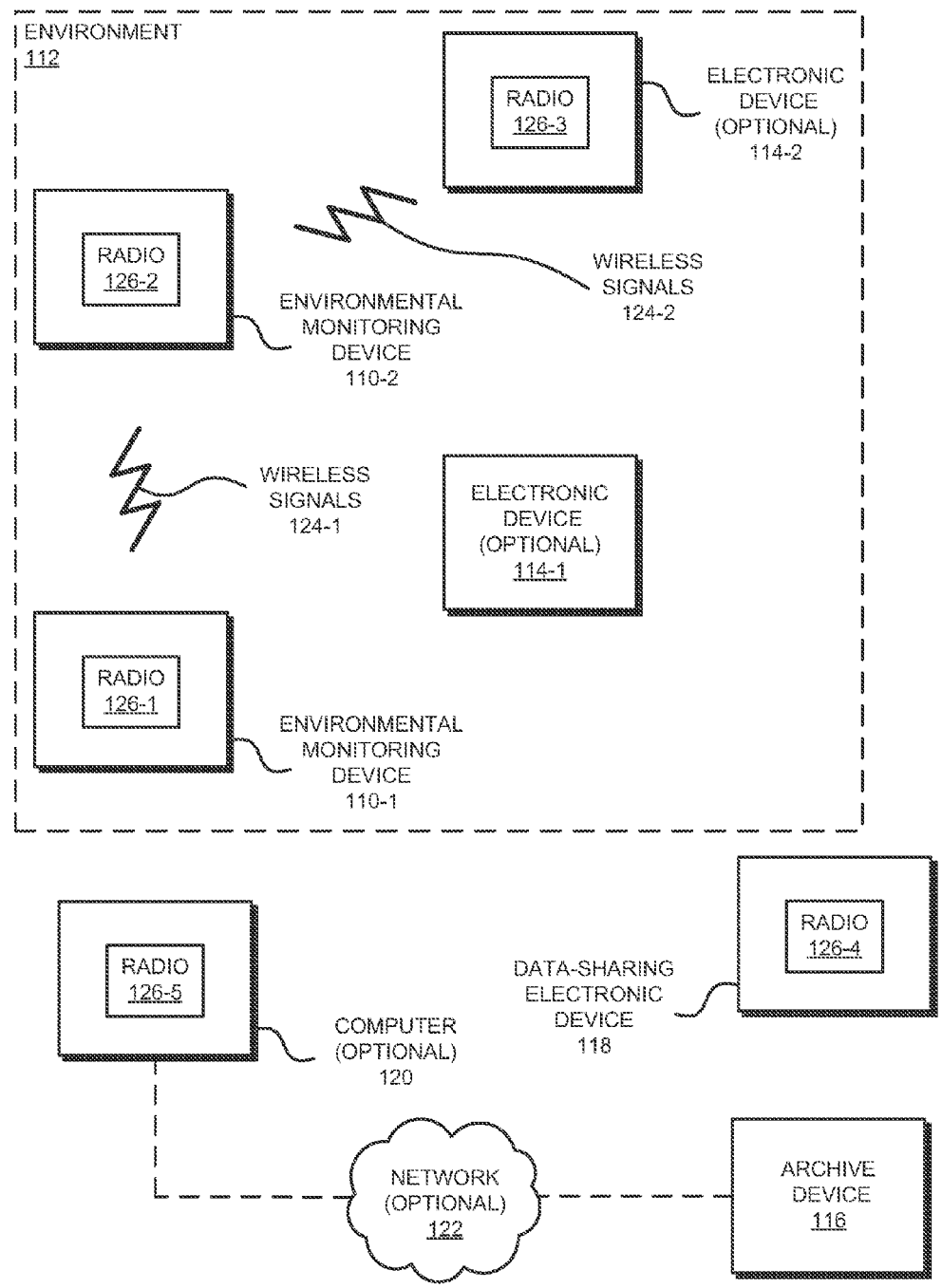
FIG. 1 is a block diagram illustrating electronic devices communicating in accordance with an embodiment of the present disclosure.

An environmental monitoring device that includes a sensor mechanism is described. During operation of the environmental monitoring device, heat generated by a processor in the environmental monitoring device may result in a convective fluid flow over the sensor mechanism that facilitates measurements of sensor data associated with an environmental condition in an external environment that includes the environmental monitoring device. Alternatively, a fluid driver (such as a fan) associated with the processor may produce the fluid flow over the sensor mechanism. Note that the fluid flow may include an airflow and/or a liquid flow. Moreover, the environmental monitoring device may include baffles that direct the fluid flow over a selected sensor in a set of sensors in the sensor mechanism.

In this way, the environmental monitoring device may facilitate low-power and/or low-cost measurements of the environmental condition. These capabilities promote sales of the environmental monitoring device (and, more generally, commercial activity) and may enhance customer satisfaction with the environmental monitoring device.

Communication between electronic devices (such as the environmental monitoring device and an alarm device) may utilize wired, optical and/or wireless communication. For example, the wireless communication may involve communicating packets or frames that are transmitted and received by radios in the electronic devices in accordance with a communication protocol, such as: Bluetooth™ (from the Bluetooth Special Interest Group of Kirkland, Wash.), an Institute of Electrical and Electronics Engineers (IEEE) 802.15 standard (such as ZigBee® from the ZigBee® Alliance of San Ramon, Calif.), an Institute of Electrical and Electronics Engineers (IEEE) 802.11 standard. Z-Wave, a power-line communication standard, an infra-red communication standard, a universal serial bus (USB) communication standard, a near-field-communication standard or specification (from the NFC Forum of Wakefield, Mass.), another wireless ad-hoc network standard, and/or another type of wireless interface. In some embodiments, the communication protocol may be compatible with a $2^{nd}$ generation or mobile telecommunication technology, a $3^{rd}$ generation of mobile telecommunications technology (such as a communication protocol that complies with the International Mobile Telecommunications-2000 specifications by the International Telecommunication Union of Geneva, Switzerland), a $4^{th}$ generation of mobile telecommunications technology (such as a communication protocol that complies with the International Mobile Telecommunications Advanced specification by the International Telecommunication Union of Geneva, Switzerland), and/or another cellular-telephone communication technique. For example, the communication protocol may include Long Term Evolution or LTE. In the discussion that follows, ZigBee® is used as an illustrative example. In addition, the communication may occur via a wide variety of frequency bands, including frequencies associated with the so-called 'white space' in frequencies bands associated with analog television broadcasting.

The communication between the electronic devices is shown in FIG. 1, which presents a block diagram illustrating communication among environmental monitoring devices 110, optional electronic devices 114 (such as regulator devices e.g., optional electronic device 114-2, and/or legacy electronic devices, e.g., optional electronic device 114-1) and data-sharing electronic device using wireless signals, and communication with optional computer 120 and optional network 122 (such as the Internet, a wireless local area network, an Ethernet network, an intra-net, an optical network, etc.) and aggregating or archive device 116 (which may or may not involve wireless signals). As described further below with reference to FIGS. 11-29, environmental monitoring devices 110 may monitor environmental conditions in an environment 112 (which is sometimes referred to as an 'external environment'), such as a portion of a building, the building, a container or a package, a vehicle, a liquid, and/or a train car. (Note that one or more of environmental monitoring devices 110 may be immersed in a liquid, and environment 112 may be at a fixed location or time-varying locations.) For example, at least some of environmental monitoring devices 110 may include sensors that provide sensor data that reflects the environmental conditions in environment 112. In general, the sensor data may be provided without or excluding interaction (such as communication and/or electrical coupling) between environmental monitoring devices 110 and optional electronic devices 114. Thus, sensors in environmental monitoring devices 110 may indirectly infer information about the operation and/or the performance of optional electronic devices 114 based on the monitored environmental conditions. However, in some embodiments at least some of environmental monitoring devices 110 interact directly with at least some of optional electronic devices 114 (via communication or electrical coupling), thereby facilitating direct measurement of the sensor data, as well as feedback control of these electronic devices by at least some of environmental monitoring devices 110. In some embodiments, one or more of environmental monitoring devices 110 is integrated into one or more other electronic device, such as one or more of optional electronic devices 114.

The sensor data may be analyzed locally by at least one of environmental monitoring devices 110 and/or remotely by archive device 116. Moreover, the sensor data and/or the analyzed sensor data may be communicated among environmental monitoring devices 110. In particular, environmental monitoring devices 110 may form a ZigBee® mesh network, with ZigBee® end devices communicating with a ZigBee® coordinator (such as environmental monitoring device 110-1) via one or more optional ZigBee® routers. Then, environmental monitoring device 110-1 may communicate (wirelessly and/or via optional computer 120 and optional network 122) the sensor data and/or the analyzed sensor data to archive device 116.

In addition, the sensor data and/or the analyzed sensor data may be communicated or shared with one or more other electronic devices, such as data-sharing electronic device 118 (e.g., a cellular telephone or a portable electronic device) and/or remote servers or computers not shown in FIG. 1. For example, the sensor data and/or the analyzed sensor data may be communicated to data-sharing electronic device 118 by at least some of environmental monitoring devices 110, such as the one or more optional ZigBee® routers and/or the ZigBee® coordinator. (Thus, at least some of environmental monitoring devices 110 may function as sensor-data hubs for other environmental monitoring devices 110.) Alternatively, the sensor data, the analyzed sensor data and/or operational information (such as remaining battery life) about at least some of environmental monitoring devices 110 may be communicated to data-sharing electronic device 118 by archive device 116 using wired, optical and/or wireless communication. Data-sharing electronic device 118 may display or provide this information to a user. In some embodiments, data-sharing electronic device 118 compares the information from multiple environmental monitoring devices 110 to ensure consistency before presenting the information to the user. This may reduce the likelihood of false alarms or misinformation. Alternatively, data-sharing electronic device 118 can present comparisons of the information from multiple environmental monitoring devices 110.

In general, the sensor data and/or the analyzed sensor data that is communicated and/or stored by environmental monitoring devices 110 and/or archive device 116 may be protected. For example, the sensor data may be encrypted, digitally signed and/or securely hashed (such as using a one-way cryptographic hash function) by environmental monitoring devices 110. Furthermore, archive device 116 may store the sensor data and/or the analyzed sensor data in secure, certified historical records or logs of the environmental conditions in environment 112. In principle, the information stored by archive device 116 may be protected. However, in some embodiments, users of environmental monitoring devices 110, who, in general, control how their data is used and shared, may instruct environmental monitoring devices 110 to provide, via the mesh network, information to archive device 116 that allows archive device 116 to unprotect the sensor data and/or the analyzed sensor data. Similarly, in response to requests from authorized recipients for the sensor data and/or the analyzed sensor data (such as a request from data-sharing electronic device 118), archive device 116 may provide access to the stored sensor data and/or the analyzed sensor data. If the sensor data and/or the analyzed sensor data are protected, the associated environmental monitoring devices 110 may provide protection information to data-sharing electronic device 118 that allows data-sharing electronic device 118 to unprotect the sensor data and/or the analyzed sensor data.

Environmental monitoring devices 110 may allow a variety of services to be offered to: users associated with environmental monitoring devices 110 (such as owners or renters of these environmental monitoring devices), suppliers of components or spare parts, maintenance personnel, insurance companies, insurance brokers, realtors, leasing agents, apartment renters, hotel guests, hotels, restaurants, businesses, organizations, governments, potential buyers of physical objects, a shipping or transportation company, etc. For example, as described further below with reference to FIGS. 13-20, based on the analyzed sensor data feedback about the operation of one or more of optional electronic devices 114 (such as a legacy electronic device) may be provided by one or more of environmental monitoring devices 110 on displays, using speakers and, more generally, on physiological output devices that provide sensory information (such as lighting or an illumination pattern). Thus, a user may be alerted if a legacy electronic device is activated or if it is not functioning properly. More generally, the feedback may indicate the presence of an environmental condition in environment 112, such as: presence of an allergen, fire, flooding, a power outage, a chemical contaminant, an infestation, opening of a door, an individual getting out of bed, an individual waking up, an individual crying, an individual tossing and turning in bed, an individual shivering, a change in health condition of an individual (such as an illness, a chronic disease, etc.), etc.

In addition, environmental monitoring devices 110 may include a variety of features to facilitate the monitoring of the environmental condition and the providing of the feedback. For example, as described further below with reference to FIGS. 11 and 12, at least one of environmental monitoring devices 110 may include an imaging device that has different spatial sensitivity in different regions of environment 112, which defines a field of view of the imaging device. Moreover, as described further below with reference to FIGS. 21 and 22, during operation of at least one of environmental monitoring devices 110 may heat generated by a processor (and, more generally, a processing subsystem) may result in a convective fluid flow (such as a liquid flow or airflow) over one or more sensors in a sensor mechanism in one of environmental monitoring devices 110 that facilitates the monitoring. Alternatively or additionally, a forced fluid driver (such as a fan) may produce the fluid flow. Furthermore, as described further below with reference to FIGS. 23-25, at least one of environmental monitoring devices 110 may include a power source with a primary power source and a secondary power source. The secondary power source may have at least a 10-year life (and, more generally, an N-year life, where N is an integer, such as 5-20 years), and may power at least a subset of the functionality of at least the one of environmental monitoring devices 110 in the event the primary power source fails or there is a power outage. For example, a sensor mechanism in one of environmental monitoring devices 110 may include a smoke detector and/or a carbon-monoxide detector that is powered by the secondary power source in the event the primary power source fails. Additionally, as described further below with reference to FIGS. 26-29, at least one of environmental monitoring devices 110 may be remateably mounted to a base that is on or underneath a wall in environment 112. If the one of environmental monitoring devices 110 is removed from a spatial location of the base without first receiving a security code, this environmental monitoring device 110 may provide an alert, thereby determining theft or tampering.

Additionally, one or more of environmental monitoring devices 110 provide a maintenance notification based on the analyzed sensor data, which is associated with the operation of one of optional electronic devices 114 (such as a legacy electronic device or an electronic device that is included in a feedback loop with one of environmental monitoring devices 110) and/or which represents an environmental condition in environment 112. For example, the maintenance notification may include an instruction to replace a battery. In addition, the maintenance notification and any subsequent remedial action (such as a repair or service performed on one of optional electronic devices 114) may be stored in a historical record or log for environment 112 (such as a historical record maintained by archive device 116).

In some embodiments, a regulator device (such as one of optional electronic devices 114, e.g., a thermostat, a humidifier, an air purifier, a ventilator device, a fan, a motor, a window opener, a door opener, an access-control device for the environment, etc.) that regulates an environmental condition is modified based on a comparison of the sensor data and a target value of the environmental condition in environment 112. For example, one of environmental monitoring devices 110 may provide a control signal to the regulator device to modify an environmental condition (such as the temperature, humidity, airflow, etc.) based on a comparison of the sensor data and a target value performed by the environmental monitoring device.

In these ways, environmental monitoring devices 110 and/or archive device 116 may be used to: implement an information network with one or more legacy electronic devices; securely aggregate and selectively disseminate sensor data about environmental conditions; provide feedback about one or more environmental conditions in environment 112 (such as an alert provided by one of optional electronic devices 114); allow users to remotely control alerts provided by environmental monitoring devices 110 by modifying alert settings of environmental monitoring devices 110; dynamically change illumination patterns in environment 112; and facilitate monitoring and maintaining of one or more environmental conditions in environment 112.

As noted previously, the communication between environmental monitoring devices 110, optional electronic devices 114, archive device 116, data-sharing electronic device 118 and/or optional computer 120 may involve the exchange of packets. These packets may be included in frames in one or more wireless channels.

Figure 2:
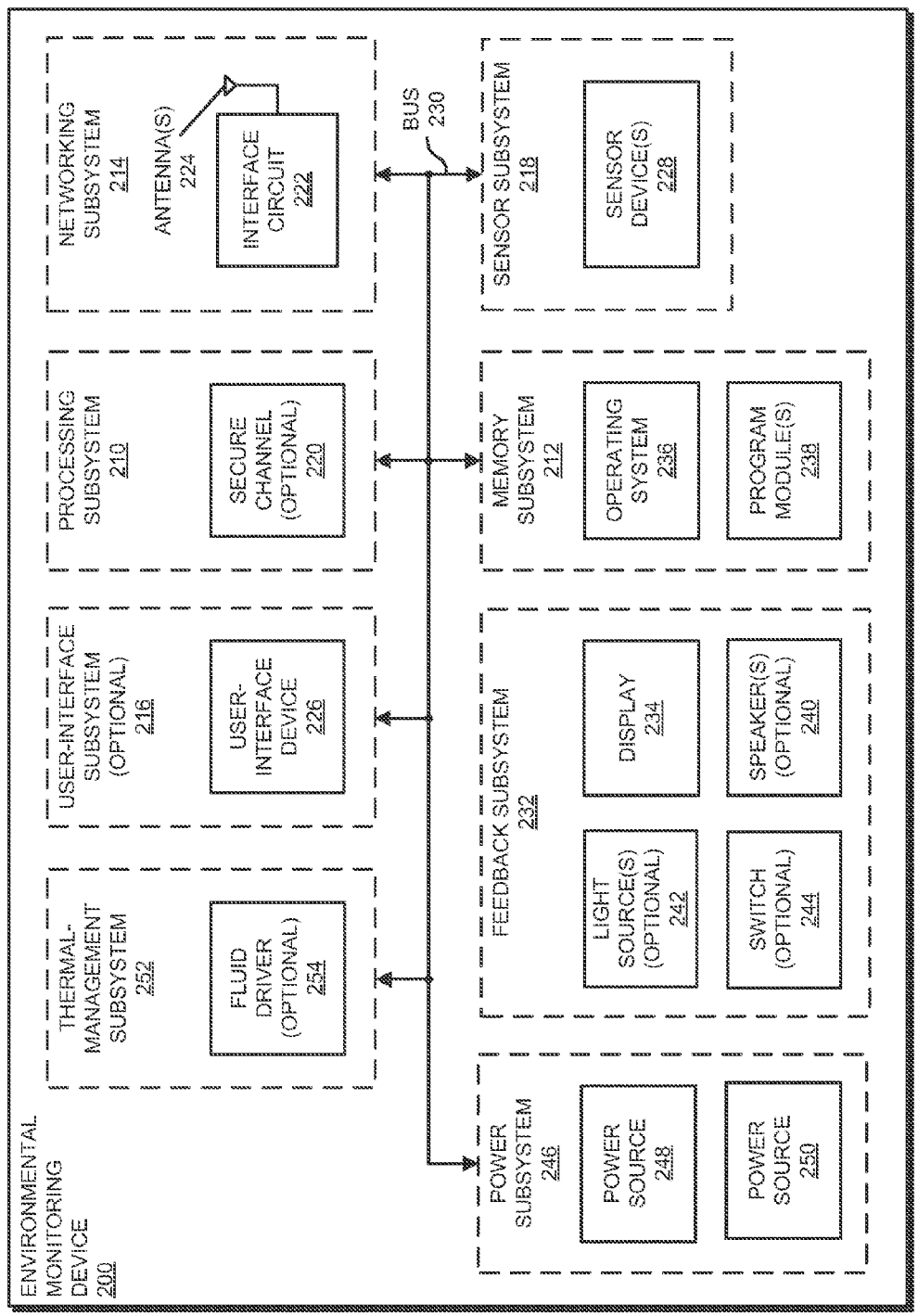
FIG. 2 is a block diagram illustrating an environmental monitoring device of FIG. 1 in accordance with an embodiment of the present disclosure.

Moreover, as described further below with reference to FIG. 2, environmental monitoring devices 110, archive device 116, data-sharing electronic device 118, optional computer 120 and/or optionally some of optional electronic devices 114 (such as optional electronic device 114-2) may include subsystems, such as: a networking subsystem, a memory subsystem, a processing subsystem, an optional user-interface subsystem, and a sensor subsystem. In addition, these electronic devices may include radios 126 in the networking subsystems. More generally, environmental monitoring devices 110, archive device 116, data-sharing electronic device 118, optional computer 120 and/or optionally some of optional electronic devices 114 can include (or can be included within) any electronic devices with networking subsystems that enable wirelessly communication with another electronic device. This can comprise transmitting frames on wireless channels to enable the electronic devices to make initial contact, followed by exchanging subsequent data/management frames (such as connect requests or petitions to establish a connection or link), configuring security options (e.g., encryption on a link or in a mesh network), transmitting and receiving packets or frames, etc.

As can be seen in FIG. 1, wireless signals 124 (represented by a jagged line) are transmitted from/received by radios 126 in environmental monitoring devices 110, data-sharing electronic device 118, optional computer and/or optionally some of optional electronic devices 114 (such as optional electronic device 114-2). In general, wireless communication among these electronic devices may or may not involve a connection being established between the electronic devices, and therefore may or may not involve communication via a wireless network. (Note that the communication between optional computer 120 and archive device 116 may occur via optional network 122, which may involve wired or optical communication with a different communication protocol than wireless signals 124.)

Furthermore, the processing of a packet or frame in an electronic device (such as environmental monitoring device 110-1) may include: receiving wireless signals 124 with the packet or frame; decoding/extracting the packet or frame from received wireless signals 124 to acquire the packet or frame; and processing the packet or frame to determine information contained in the packet or frame (such as at least a portion of a certified data packet).

As noted previously, in general communication among the electronic devices may be protected. This may involve encryption using an encryption key (such as an encryption key associated with one of environmental monitoring devices 110 and/or a secure channel in a processor in one of environmental monitoring devices 110). The encryption key may use symmetric or asymmetric encryption techniques. Alternatively or additionally, a secure hash function (such as SHA-256) may be used. For example, the secure hash may supplement encryption that is associated with a network interface in one or more of environmental monitoring devices 110.

Although we describe the environment shown in FIG. 1 as an example, in alternative embodiments, different numbers or types of electronic devices may be present. For example, some embodiments comprise more or fewer electronic devices.

We now describe embodiments of the environmental monitoring device, the archive device, and other electronic devices in FIG. 1. FIG. 2 presents a block diagram illustrating environmental monitoring device 200, such as one of environmental monitoring devices 110. This electronic device includes processing subsystem 210, memory subsystem 212, a networking subsystem 214, an optional user-interface subsystem 216, sensor subsystem 218 (i.e., a data collection subsystem), feedback subsystem 232, power subsystem 246 and thermal-management subsystem 252. Processing subsystem 210 includes one or more devices configured to perform computational operations. For example, processing subsystem 210 can include one or more microprocessors, application-specific integrated circuits (ASICs), microcontrollers, programmable-logic devices, and/or one or more digital signal processors (DSPs).

In addition, processing subsystem 210 may include an optional secure channel 220 that performs secure processing of information, securely communicates with other components in environmental monitoring device 200, and more generally performs secure services. This secure channel may include one or more processors, a secure boot ROM, one or more security peripherals, and/or other components. The security peripherals may be hardware-configured to assist in the secure services performed by optional secure channel 220. For example, the security peripherals may include: authentication hardware implementing various authentication techniques, encryption hardware configured to perform encryption, secure-interface controllers configured to communicate over a secure interface to other components, and/or other components. In some embodiments, instructions executable by optional secure channel 220 are stored in a trust zone in memory subsystem 212 that is assigned to optional secure channel 220, and optional secure channel 220 fetches the instructions from the trust zone for execution. Optional secure channel 220 may be isolated from the rest of processing subsystem 210 except for a carefully controlled interface, thus forming a secure region for optional secure channel 220 and its components. Because the interface to optional secure channel 220 is carefully controlled, direct access to components within optional secure channel 220 (such as a processor or a secure boot ROM) may be prevented. In some embodiments, optional secure channel encrypts and/or decrypts authentication information communicated with optional user-interface subsystem 216 and/or received via networking subsystem 214, and encrypts and/or decrypts information (such as sensor data) communicated with sensor subsystem 218.

Memory subsystem 212 includes one or more devices for storing data and/or instructions for processing subsystem 210, networking subsystem 214, optional user-interface subsystem 216 and/or sensor subsystem 218. For example, memory subsystem 212 can include dynamic random access memory (DRAM), static random access memory (SRAM), and/or other types of memory. In some embodiments, instructions for processing subsystem 210 in memory subsystem 212 include: one or more program modules 238 or sets of instructions (such as an environmental monitoring application, an environmental illumination program, a data-logging application, a data-sharing application and/or a maintenance application), which may be executed in an operating environment (such as operating system 236) by processing subsystem 210. Note that the one or more computer programs may constitute a computer-program mechanism or a program module. Moreover, instructions in the various modules in memory subsystem 212 may be implemented in: a high-level procedural language, an object-oriented programming language, and/or in an assembly or machine language. Furthermore, the programming language may be compiled or interpreted, e.g., configurable or configured (which may be used interchangeably in this discussion), to be executed by processing subsystem 210.

In addition, memory subsystem 212 can include mechanisms for controlling access to the memory. In some embodiments, memory subsystem 212 includes a memory hierarchy that comprises one or more caches coupled to a memory in environmental monitoring device 200. In some of these embodiments, one or more of the caches is located in processing subsystem 210.

In some embodiments, memory subsystem 212 is coupled to one or more high-capacity mass-storage devices (not shown). For example, memory subsystem 212 can be coupled to a magnetic or optical drive, a solid-state drive, or another type of mass-storage device. In these embodiments, memory subsystem 212 can be used by environmental monitoring device 200 as fast-access storage for often-used data, while the mass-storage device is used to store less frequently used data.

Networking subsystem 214 includes one or more devices configured to couple to and communicate on a wired, optical and/or wireless network (i.e., to perform network operations), including an interface circuit 222 (such as a ZigBee® communication circuit) and one or more antennas 224. For example, networking subsystem 214 can include: a ZigBee® networking subsystem, a Bluetooth™ networking system (which can include Bluetooth™ Low Energy, BLE or Bluetooth™ LE), a cellular networking system (e.g., a 3G/4G network such as UMTS, LTE, etc.), a USB networking system, a networking system based on the standards described in IEEE 802.11 (e.g., a Wi-Fi® networking system), an Ethernet networking system, an infra-red communication system, a power-line communication system and/or another communication system (such as a near-field-communication system or an ad-hoc-network networking system).

Moreover, networking subsystem 214 includes processors, controllers, radios/antennas, sockets/plugs, and/or other devices used for coupling to, communicating on, and handling data and events for each supported networking or communication system. Note that mechanisms used for coupling to, communicating on, and handling data and events on the network for each network system are sometimes collectively referred to as a 'network interface' for the network system. Moreover, in some embodiments a 'network' between the electronic devices does not yet exist. Therefore, environmental monitoring device may use the mechanisms in networking subsystem 214 for performing simple wireless communication between environmental monitoring device 200 and other electronic devices, e.g., transmitting advertising frames, petitions, beacons and/or information associated with near-field communication.

Optional user-interface subsystem 216 may include one or more processors, controllers and devices for receiving information for a user of environmental monitoring device 200. For example, optional user-interface subsystem 216 may include a user-interface device 226 (and, more generally, a user-input mechanism), such as: a keypad, a touch-sensitive display, optical character recognition, image recognition, gesture recognition, biometric recognition (such as a fingerprint, a palm print, a retinal pattern, etc.), and/or voice recognition. The information may include: authentication information from the user (such as a passcode or a security code for unlocking access to environmental monitoring device 200, some of the functionality of environmental monitoring device 200 and/or to allow environmental monitoring device 200 to be moved from a current location); user-feedback about a request for access to sensor data associated with environmental monitoring device 200; and/or user preferences for operation of environmental monitoring device 200 (such as alarm settings, when and/or how to provide notifications, etc.). This information may be securely communicated to processing subsystem 210 (such as by encrypting the information). In addition, the information communicated may also include an encryption key that is specific to environmental monitoring device 200 and/or components in environmental monitoring device 200, such as optional secure channel 220.

Furthermore, sensor subsystem 218 may include one or more sensor devices 228 (or a sensor array), which may include one or more processors and memory. For example, the one or more sensor devices 228 may include: a thermal sensor (such as a thermometer), a humidity sensor, a barometer, a camera or video recorder (such as a CCD or CMOS imaging sensor), one or more microphones (which may be able to record acoustic information in mono or stereo), an infrared sensor (which may be active or passive), a microscope, a particle detector (such as a detector of dander, pollen, dust, exhaust, etc.), an air-quality sensor, a particle sensor, an optical particle sensor, an ionization particle sensor, a smoke detector (such as an optical smoke detector or an ionizing smoke detector), a radon detector, a carbon-monoxide detector, a chemical sensor or detector, a volatile-organic-compound sensor, a combustible gas sensor, a chemical-analysis device, a mass spectrometer, a microanalysis device, a nano-plasmonic sensor, a genetic sensor (such as a micro-array), an accelerometer, a position or a location sensor (such as a location sensor based on the Global Positioning System or GPS), a gyroscope, a motion sensor (such as a light-beam sensor), a contact sensor, a strain sensor (such as a strain gauge), a proximity sensor, a microwave/radar sensor (which may be active or passive), an ultrasound sensor, a vibration sensor, a fluid flow sensor, a photo-detector, a Geiger counter, a radio-frequency radiation detector, and/or another device that measures a physical effect or that characterizes an environmental factor or physical phenomenon (either directly or indirectly).

Moreover, the one or more sensor devices 228 may include redundancy (such as multiple instances of a type of sensor device) to address sensor failure or erroneous readings, to provide improved accuracy and/or to provide improved precision. Note that sensor data acquired by the one or more sensor devices 228 may be securely communicated to processing subsystem 210 (such as by encrypting the sensor data). In addition, the sensor data communicated may also include a digital signature that is specific to environmental monitoring device 200 and/or components in environmental monitoring device 200, such as optional secure channel 220.

Feedback subsystem 232 may include a display 234 for displaying information, such as: feedback about an environmental condition in an environment that includes environmental monitoring device 200, information about the operation of environmental monitoring device 200, and/or a maintenance notification associated with a regulator device in the environment or environmental monitoring device 200 (such as when one of power sources 248 and 250 needs to be replaced). In particular, feedback subsystem 232 may include a display driver and display 234, such as: a liquid-crystal display, an e-ink display, an organic light emitting diode display, a braille output device, a laser projection display, a multi-touch touchscreen, a color-wheel display, etc. Note that display subsystem 232 may be included in optional user-interface subsystem 216.

In addition, feedback subsystem 232 may include one or more light sources 242 (and, more generally, an illumination mechanism), such as: incandescent light sources, electroluminescent light sources (e.g., light emitting diodes), etc. These light sources may provide different illumination patterns, which may be programmable. The different illumination patterns may have: different spatial patterns in the environment that includes environmental monitoring device 200, different wavelengths of light and/or different light intensities. Thus, a particular illumination pattern may illuminate at least a portion of the environment.

During operation of environmental monitoring device 200, processing subsystem 210 may execute one or more program modules 238, such as an environmental monitoring application. In particular, environmental monitoring application may instruct one or more sensor devices 228 to measure or acquire sensor data that represents one or more environmental conditions in an environment that includes environmental monitoring device 200. For example, the environmental condition may include: presence of an individual (such as a resident or a potential burglar), opening of a door, an individual getting out of bed, an individual waking up, an individual crying, an individual tossing and turning in bed, an individual shivering, presence of a chemical compound (such as exhaust, carbon monoxide, radon, smoke, a non-volatile organic compound and/or a volatile organic compound), presence of an allergen (such as dander or pollen), presence of dust, presence of a fungus, a fire, presence of smoke, flooding, a water leak, a chemical leak, presence of an insect or rodent (and, more generally, an infestation), discharge of a firearm, a possible altercation or criminal act (such as domestic violence), a medical emergency, a change in health condition of an individual, availability of electrical power (such as whether there is a power failure), a lighting condition (such as whether the lights are on or off), temperature deviating from a predefined target, and/or humidity deviating from a predefined target. In some embodiments, the environmental condition is associated with the operation of a regulator device (which may or may not be a legacy electronic device). The regulator device (and, more generally, one of optional electronic devices 114 in FIG. 1) may include: a smoke detector, a thermostat, a carbon-monoxide detector, an appliance, a pet or animal feeder, a plant or animal watering device, a clock, a security alarm, a humidifier, an air filter, a switch, a light, etc. Note that the monitoring of the sensor data may be continuous, periodic (such as after a time interval has elapsed) or as needed (such as event-driven monitoring).

The sensor data may be communicated to processing subsystem 210. Then, the environmental monitoring application may optionally analyze the sensor data, e.g., calculating a discrete or a Fourier transform, determining a histogram, performing filtering or signal processing, performing data compression, calibrating one or more of sensor devices 228, managing power consumption of environmental monitoring device 200, identifying one or more of sensor devices 228 that are not working or which are outputting erroneous sensor data, applying another transformation, calculating statistics (such as moments of a distribution), performing supervised learning (such as Bayesian analysis), performing noise reduction, normalizing the sensor data, converting units, etc. (Alternatively or additionally, the sensor data or a document summarizing the sensor data may be communicated to another electronic device using networking subsystem 214 and the analysis may be performed remotely, e.g. by archive device 116 in FIGS. 1 and 4.) For example, the analysis may determine whether an environmental condition is present in the environment. (In some embodiments, this analysis is based on information, such as sensor data and/or environmental conditions, received from other environmental monitoring devices. This may allow calibration settings, such as environment-specific threshold values, to be determined for the environment and/or environmental monitoring device 200.) Then, the environmental monitoring application may provide feedback to a user of environmental monitoring device 200, data-sharing electronic device 118 (FIG. 1) and/or directly to one of optional electronic devices 114 in FIG. 1 (if this electronic device is able to communicate with environmental monitoring device 200 via networking subsystem 214). In particular, the environmental monitoring application may instruct feedback subsystem 232 to provide sensory information, such as a text or graphical message, a graph, a report, a chart, a spectrum, a video displayed on display 234, a sound or audio message (such as an alert) output by optional speakers 240 and/or an illumination pattern output by optional light sources 242. For example, the sensory information may include: a range of values, numerical measurements, shades of gray (or grayscale), colors, chemical formulas, images, illumination patterns, textures, patterns (which may correspond to one or more environmental conditions), tessellations with gradients of larger or smaller element sizes, and/or tessellations of increasing or decreasing element sizes (such as tessellation that are adjusted to be larger or smaller as a given environmental condition increases or decreases). Thus, in some embodiments the sensory information includes a change in the color of environmental monitoring device 200. Alternatively or additionally, the feedback may include a change in the illumination pattern provided by optional light sources 242. In some embodiments, the feedback is communicated using networking subsystem 214 and presented to the user (or other individuals) on another electronic device, such as data-sharing electronic device 118 (FIG. 1) or a different electronic device (such as the user's cellular telephone, tablet computer or computer) that is used for remote visualization of: the sensor data, the analyzed sensor data, the environmental condition and/or the feedback.

In some embodiments, the environmental monitoring application may provide, via networking subsystem 214, the feedback to one or more of environmental monitoring devices 110 (FIG. 1) and/or other electronic devices (such as computers or servers associated with or operated on behalf of: component suppliers, retailers, insurance companies, maintenance organizations, shipping companies, landlords or property owners, a corporate-compliance organization, inspectors, businesses, government agencies, etc.). For example, the environmental monitoring application may utilize a Short Message Service, email, a social network and/or a messaging service with a restricted number of characters per message. Alternatively or additionally, the feedback may be posted to a web page or website (and, more generally, a location on a network), and one or more recipients may be notified via networking subsystem 214, e.g., a link to the location may be provided to the recipients.

In turn, an electronic device (such as data-sharing electronic device 118 in FIG. 1) may, via networking subsystem 214, modify settings of environmental monitoring device 200 (such as alarm settings) that change how the feedback is provided locally (e.g., using optional speakers 240) and/or remotely (e.g., using networking subsystem 214). For example, a user of data-sharing electronic device 118 in FIG. 1 may access a web page associated with a provider of environmental monitoring device 200 to modify the settings.

Figure 3:
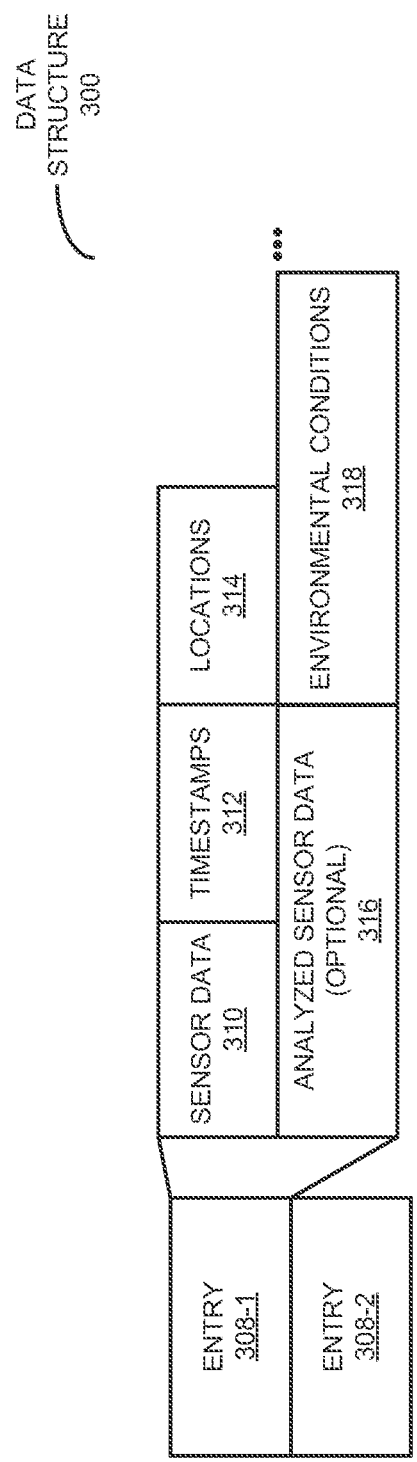
FIG. 3 is a block diagram illustrating a data structure with sensor data in the electronic device of FIG. 2 in accordance with an embodiment of the present disclosure.

Note that the sensor data and/or the analyzed sensor data may be stored, at least temporarily, in a data structure in memory subsystem 212. This is shown in FIG. 3, which presents a data structure 300. In particular, data structure 300 may include entries 308 with: sensor data 310, timestamps 312, locations 314, optional analyzed sensor data 316, and/or environmental conditions 318. Note that locations 314 (or location information) may specify locations were the sensor data was acquired or measured. For example, the location information may be measured using a sensor device in environmental monitoring device 200 in FIG. 2 (such as a location monitor) and/or the location information may be received from another electronic device that is proximate to environmental monitoring device 200 in FIG. 2 (such as an individual's cellular telephone). Thus, the location may be determined via GPS and/or a cellular-telephone network (such as triangulation or trilateration).

Referring back to FIG. 2, in some embodiments imaging data from one or more imaging sensors (or imaging devices) in sensor devices 228 is analyzed to determine the environmental condition. In order for environmental monitoring device 200 to have more accurate or focused monitoring of at least a portion of the environment (such as in different regions relative to a remainder of the environment), environmental monitoring device 200 may have a restricted field of view. This field of view may be associated with different spatial sensitivity of the one or more imaging sensors in the different regions of the environment. For example, the imaging sensor may include a lens with a predefined distortion that provides the different spatial sensitivity, such as Fresnel lens. In some embodiments, a mechanical stop provides the different spatial sensitivity. Alternatively, processing subsystem 210 (and, more generally, a control mechanism) provides a control signal that selectively rotates an angular adjustment mechanism (such as a motor) in sensor subsystem 218 about an axis to change an orientation of the field of view. However, in some embodiments the angular adjustment mechanism selectively rotates in response to an external force (or torque), such as an external force applied by a user of environmental monitoring device 200. Note that the restricted field of view may allow processing subsystem 210 (and, more generally, a detection mechanism) to use the sensor data and/or the analyzed sensor data to detect: motion of an object in the field of view, a light scattering pattern in the field of view and/or a light intensity in the field of view.

Moreover, acoustic data from one or more acoustic sensors (or acoustic devices) in sensor devices 228 may be analyzed to determine the environmental condition. For example, the acoustic data may correspond to sound in the environment (such as temporal audio samples of the sound provided by a microphone). Based on the acoustic data, processing subsystem 210 may determine if a smoke detector or carbon-monoxide detector (and, more generally, an alarm device), either of which may be separate from environmental monitoring device 200, is activated (e.g., sounding an alert or an alarm) in the environment. Note that the sound may include a temporal 3 (T-3) acoustic pattern (with a beep, pause and an alarm pattern or signal) that is compatible with an American National Standards Institute standard S3.42 1990. (Thus, the one or more acoustic sensors may monitor one or more specific frequencies or acoustic patterns.) In some embodiments, processing subsystem 210 uses the acoustic data and predefined characterization of the environment to determine if an alarm device (such as a smoke detector or a carbon-monoxide detector) is activated. For example, the predefined characterization may include a location of the alarm device (such as a location of the alarm device relative to environmental monitoring device 200). This location may be specified by: an image of the environment, a positioning system (such as GPS), a communication network (such as a cellular-telephone network), and/or an acoustic latency in the external environment. Alternatively, the predefined characterization may include an acoustic transfer function of the environment proximate to the alarm device and environmental monitoring device 200.

If processing subsystem 210 determines that the smoke detector or the carbon-monoxide detector is activated, processing subsystem 210 may provide a control signal to optional speakers 240 (and, more generally, an acoustic output mechanism, such as a piezoelectric buzzer) so that an audible sound is output. This may assist the smoke detector or the carbon-monoxide detector in alerting individuals in the environment to the presence of the environmental condition. For example, one or more additional sensors in sensor devices 228 (and, more generally, a sensor mechanism) may provide sensor data when a biological life form is present in the environment (such as an individual or an animal). Processing subsystem 210 may use this sensor data to determine of the biological life form is present, and may output a control or output signal to networking subsystem 214 if the alert is detected and the biological life form is present. In response, networking subsystem 214 can communicate location information for environmental monitoring device 200 to an electronic device. In this way, for example, environmental monitoring device 200 can alert firemen or first responders to the presence of a child or a pet in a smoke-filled room or a room with carbon monoxide, to assist them in promptly locating and rescuing the child or the pet.

The predefined characterization can also include location information with respect to a biological organism (such as the child or the pet), and can be redefined at periodic or aperiodic intervals. For example, environmental monitoring device 200 may detect when a human is in a bedroom and specify their location relative to the environmental monitoring device 200, such as that environmental monitoring device 200 is approximately 3 meters from the human. This information may be useful to first responders in fires, earthquakes, floods, other natural disasters or emergency situations.

In addition, one or more additional sensors in sensor devices 228 may provide sensor data associated with monitoring of a physical phenomenon or a chemical (and, more generally, an environmental condition) in the environment. Using the sensor data and/or analyzed sensor data, processing subsystem 210 may assess a degree of threat in the environment, and processing subsystem 210 may provide a different control signal to optional speakers 240 so that different audible sounds are produced as the degree of threat changes. In some embodiments, the change to the audible sound provides quantitative feedback about the degree of the threat in the environment (and, more generally, the feedback may include quantitative information about the degree of the threat).

In response to an environmental condition or a threat, environmental monitoring device 200 may output an alert, which may include audible sound (or feedback) in the environment and/or information that is wirelessly communicated to one or more electronic devices (such as data-sharing electronic device 118 in FIG. 1). There may be different types of alerts (such as different warning sounds, lights, messages, etc.) for different environmental conditions. Additionally, environmental monitoring device 200 may output or provide more than one alert at the same time.

In some embodiments, processing subsystem 210 performs a remedial action in response to an alert or an alarm (i.e., one or more environmental conditions). This remedial action may include communicating with a regulator device to correct the environmental condition(s). For example, via networking subsystem 214, processing subsystem 210 may instruct the regulator device to: ventilate the area, activate a humidifier, power on or power off a regulator device, initiate the operation of a mode on a regulator device, etc. Alternatively, as described further below, processing subsystem 210 may provide a maintenance notification (such as a notification to change an air filter). Furthermore, the alert may indicate a remedial action, such as positive or negative changes that can restore the environmental condition to a safe value. Thus, the alert may indicate that a user should turn on the ventilation or wear a safety mask when painting or vacuuming, and/or may encourage the user to stop applying a chemical product (such as paint) or to slow down the rate of application.

The type of feedback or information output or provided by environmental monitoring device 200 may be specified by an alert setting stored in memory subsystem 212. As noted previously, the alert setting may be remotely modified, e.g., via wireless communication from another electronic device (such as a user's cellular telephone) using networking subsystem 214. In this way, an alert can be remotely disabled. However, in order to prevent accidental disabling of the alert, a separate control command or code may also be required. Alternatively, one or more sensors devices 228 may monitor a user command (such as a sound, a verbal instruction or command, a gesture, a sequence of bodily motions, a facial expression, etc.) in the environment, which may be required to modify the alert setting. In some embodiments, alerts are disabled (at least temporarily) if a user activates or changes a position of a button or switch on environmental monitoring device 200 (such as an optional switch 244 in feedback subsystem 232). When a state of optional switch 244 and/or alerts is changed, environmental monitoring device 200 may provide sensory feedback to the user (such as by vibrating or other tactile feedback, making a sound, changing an illuminated color of environmental monitoring device 200, etc.).

When the providing of the alert is disabled, processing subsystem 210 may continue to assess the threat (such as the possible presence of smoke or carbon monoxide) based on subsequent sensor data and, if the threat is increasing (such as if the concentration of carbon monoxide is increasing or has become dangerous), may reactivate the providing of the alert. Alternatively, after a time interval (such as 5, 10, 15 or 30 minutes), the modified alert setting may automatically revert to the original alert setting, so that environmental monitoring device 200 can provide alerts again. In some embodiments, a user subsequently changes the modified alert setting back to the original alert setting or resets the alert setting to default. Thus, environmental monitoring device 200 may continue to assess the impact of one or more environmental factors (and, more generally, the environmental condition) on the safety of the external environment, while also providing a user operational control over alerts. In addition, environmental monitoring device 200 may provide fail safes both in how alerts are disabled and by reactivating alerts in case the threat is increasing.

Furthermore, if the sensor data from the one or more sensor devices 228 indicate the presence of an environmental condition, processing subsystem 210 executing an environmental illumination application may select an illumination pattern from a set of illumination patterns, which are associated with illumination of the environment. In response, optional light sources 242 may output the selected illumination pattern. For example, optional light sources 242 may change the spatial pattern, wavelengths of light and/or light intensity in at least a portion of the environment. This may allow environmental monitoring device 200 to dynamically change the illumination of the environment based on the environmental condition. Thus, if processing subsystem 210 determines that an individual (such as a child) is sleeping, the illumination pattern may exclude or may reduce blue wavelengths of light (such as wavelengths between 460 and 480 nm), which can disrupt sleep. More generally, environmental monitoring device may provide lighting or illumination services based on actions of an individual and/a state of the individual. Note that the illumination pattern may be specified remotely (e.g., via networking interface 214) and/or via optional user-interface subsystem 216. For example, using user-interface device 226, the user may provide a user selection that specifies a desired illumination pattern.

In some embodiments, the one or more program modules 238 include a data-logging application. In conjunction with archive device 116 (FIGS. 1 and 4), the data-logging application may maintain a secure, certified historical record or log for the environment and/or a physical object in the environment (such as a 'housefax' record for an apartment or a building). Note that the physical object may include: a portion of a building (e.g., an apartment, a hotel room, an office suite, a storage unit, etc.), the building, a container (such as a box, a package or a shipping container), a vehicle (such as a car or truck), a liquid, and/or a train car. Notably, sensor subsystem 218 may securely communicate the sensor data to processing subsystem 210. Using optional secure channel 220, a digital signature for the sensor data may be generated, e.g., using a secure hash function and/or an encryption key that are associated with environmental monitoring device 200 and/or optional secure channel 220. For example, the digital signature may be generated using a secure hash of a time stamp, a random number (or a pseudorandom number, both of which are henceforth referred to as a 'random number'), and/or an identifier of environmental monitoring device 200. Then, the data-logging application may instruct networking subsystem 214 to communicate a certified data package (with the sensor data or analyzed sensor data, the digital signature, location information and/or an associated time stamp) to archive device 116 (FIG. 1) for inclusion in the historical record or log for the environment.

Moreover, the one or more program modules 238 may include a data-sharing application. This data-sharing application may enable a designated or authorized recipient to access protected sensor data that is stored in archive device 116 (FIG. 1). In particular, when executed by processing subsystem 210, the data-sharing application may instruct sensor subsystem 218 to measure or collect sensor data that represents the environmental condition. Then, the data-sharing application may protect the sensor data and/or analyzed sensor data. For example, the sensor data and/or the analyzed sensor data may be encrypted using an encryption key by processing subsystem 210 and/or optional secure channel 220. Alternatively or additionally, the sensor data and/or the analyzed sensor data may be protected using a secure hash function in conjunction with an identifier of environmental monitoring device 200 and/or a random number generated by processing subsystem 210. Next, data-sharing application may instruct networking subsystem 214 to provide the protected sensor data and/or the analyzed sensor data to archive device 116 (FIG. 1).

Subsequently, when environmental monitoring device 200 receives, via networking subsystem 214, a request for the sensor data from data-sharing electronic device 118 (FIG. 1), the data-sharing application may access a predefined authorization preference of a user of environmental monitoring device 200 that is stored in memory subsystem 212. If the predefined authorization preference of the user authorizes the recipient associated with the request, the data-sharing application may provide, via networking subsystem 214, authorization information to archive device 116 (FIG. 1) to release the sensor data to data-sharing electronic device 118 (FIG. 1). Alternatively, the data-sharing application may instruct feedback subsystem 232 to request feedback about the request from the user. This user feedback may be received via optional user-interface subsystem 216. If the user feedback approves the request, the data-sharing application may provide, via networking subsystem 214, authorization information to archive device 116 (FIG. 1) to release the sensor data to data-sharing electronic device 118 (FIG. 1). (Thus, the user of environmental monitoring device 200 may control when other parties are allowed to access the sensor data.) Note that the data-sharing application may also provide, via networking subsystem 214, protection information specifying how to unprotect the sensor data to archive device 116 (FIG. 1) and/or to data-sharing electronic device 118 (FIG. 1). For example, the data-sharing application may provide the encryption key and/or may indicate the secure hash function, the random number and/or the identifier. In some embodiments, this protection information is received from the user of environmental monitoring device 200, e.g., via networking interface 214 and/or optional user-interface subsystem 216.

In some embodiments, the one or more program modules 238 include a maintenance application. This maintenance application may provide a maintenance notification related to the operation of environmental monitoring device 200, one of the other electronic devices in FIG. 1 and/or one or more environmental conditions in the environment. For example, the maintenance application may provide an instruction to: perform maintenance, replace a battery (and, more generally, one of power sources 248 and 250), replace one of the one or more sensor devices 228, order another replacement component (such as a filter) and/or to take out the garbage. When providing the maintenance notification, the maintenance application may instruct feedback subsystem 232 to present the maintenance notification to the user or maintenance personnel, and/or may instruct networking subsystem 214 to communicate the maintenance notification to another electronic device, such as the user's cellular telephone. In some embodiments, maintenance application suggests or recommends a specific provider or product to address or perform a remedial action in response to a maintenance notification. Alternatively, maintenance application may direct a user to a document (such as a web page or website) that includes information related to a maintenance notification.

Environmental monitoring device 200 may be designed to facilitate monitoring of one or more environmental conditions in the environment in a cost-effective manner. For example, heat generated during operation of processing subsystem 210 may result in a convective fluid flow over one or more of sensor devices 228 that facilitates measurements of sensor data associated with an environmental condition in the environment. Alternatively, thermal-management subsystem 252 may include an optional fluid driver 254 (such as a fan or a pump) associated with the processor that produces a fluid flow (such as an airflow or liquid flow) over the one or more sensor devices 228. Moreover, environmental monitoring device 200 may include baffles that direct the fluid flow or a portion of the fluid flow over a selected sensor device in the one or more sensor devices 228. In some embodiments, processing subsystem 210 (and/or a steering mechanism in sensor subsystem 218) provides a control signal that dynamically adjusts a position or orientation of the baffles so that the fluid flow is directed over a selected sensor device in the one or more sensor devices 228. However, in other embodiments the position or orientation of the baffles is set manually by the user (e.g., by applying an external force or torque to the baffles) or the baffles have fixed positions or orientations.

Moreover, environmental monitoring device 200 may include power subsystem 246 with power sources 248 and 250. Each of these power sources may include: a battery (such as a rechargeable or a non-rechargeable battery), a DC power supply, a transformer, and/or a switched-mode power supply. Moreover, either or both of power sources 248 and 250 may operate in a voltage-limited mode or a current-limited mode.

Furthermore, these power sources may be mechanically and electrically coupled by an adaptor to a wall or electrical-outlet socket plug (such as a two or three-pronged electrical-outlet plug, which may be collapsible or retractable), a light socket (or light-bulb socket), electrical wiring, a generator, a USB port, a cellular-telephone charger cable, a photodiode, a photovoltaic cell, etc. This mechanical and electrical coupling may be rigid or may be remateable.

In an exemplary embodiment, power subsystem 246 may allow processing subsystem to analyze sensor data from the one or more sensor devices 228 to assess if the environmental conditions indicate at least one of a set of threats and, if yes, to provide a corresponding alert. In particular, power subsystem 246 may include a primary power source (power source 246) and a secondary power source (power source 250). The secondary power source may have at least a 10-year life and may power at least a subset of the functionality of environmental monitoring device 200 in the event the primary power source fails. For example, the one or more sensor devices 228 may include a smoke detector that is powered by the secondary power source in the event the primary power source fails or if an external power line is unavailable. Thus, power subsystem 246 may facilitate long-term monitoring of the environmental conditions and regulatory compliance.

In some embodiments, power subsystem 246 includes or functions as a pass-through power supply for an electrical connector to an external electronic device (such as an appliance) that can be plugged into the electrical connector. Power to this electrical connector (and, thus, the external electronic device) may be controlled locally by processing subsystem 210 or optional user-interface subsystem 216 (such as via optional switch 244), and/or remotely via networking subsystem 214. Moreover, the power to the electrical connector may be turned on or off in response to sensor data provided by sensor subsystem 218 (such as when a signal is greater than or less than a user-specified or an environmental-regulation-specified threshold value, e.g., a dust concentration of 20 mg/m$^3$).

Environmental monitoring device 200 may be mounted on a base that is rigidly mounted on or underneath a wall in the environment. This mechanical coupling may be rigid or remateable. For example, the remateable coupling may involve pins that are inserted into corresponding holes and rotated into a lock position. Alternatively, the remateable coupling may involve magnets that mechanically couple to each other so long as environmental monitoring device 200 and the base are within a predefined distance (such as 1-2 cm). Note that power subsystem 246 may receive power via the rigid or remateable coupling to the base, or via inductive charging. In addition, one or more of sensor devices 228 may monitor a spatial parameter, such as: a location of environmental monitoring device 200, a velocity of environmental monitoring device 200 and/or an acceleration of environmental monitoring device 200. If this spatial parameter changes without processing subsystem 210 first receiving a security code (e.g., via networking subsystem 214 and/or optional user-interface subsystem 216), environmental monitoring device 200 may provide an alert. For example, the alert may include an audible alarm output by optional speakers 240 and/or a message to another electronic device via networking subsystem 214. These features may facilitate convenient mounting and removal of environmental monitoring device 200, while preventing theft.

Within environmental monitoring device 200, processing subsystem 210, memory subsystem 212, networking subsystem 214, optional user-interface subsystem 216, sensor subsystem 218, feedback subsystem 232, power subsystem 246 and/or thermal-management subsystem 252 may be coupled using one or more interconnects, such as bus 230. These interconnects may include an electrical, optical, and/or electro-optical connection that the subsystems can use to communicate commands and data among one another. Note that different embodiments can include a different number or configuration of electrical, optical, and/or electro-optical connections among the subsystems. In some embodiments, environmental monitoring device 200 can detect tampering with secure components (such as optional secure channel 220 and/or bus 230) and may destroy encryption/decryption keys or information (such as a stored sensor data or authentication information) if tampering is detected.

Environmental monitoring device 200 can be (or can be included in) any electronic device with at least one network interface. For example, environmental monitoring device 200 can be (or can be included in): a sensor (such as a smart sensor), a tablet computer, a smartphone, a cellular telephone, an appliance, a regulator device, a consumer-electronic device (such as a baby monitor), a portable computing device, test equipment, a digital signal processor, a controller, a personal digital assistant, a laser printer (or other office equipment such as a photocopier), a personal organizer, a toy, a set-top box, a computing device (such as a laptop computer, a desktop computer, a server, and/or a subnotebook/netbook), a light (such as a nightlight), an alarm, a smoke detector, a carbon-monoxide detector, a monitoring device, and/or another electronic device.

Although specific components are used to describe environmental monitoring device 200, in alternative embodiments, different components and/or subsystems may be present in environmental monitoring device 200. For example, environmental monitoring device 200 may include one or more additional processing subsystems, memory subsystems, networking subsystems, user-interface subsystems, sensor subsystems, feedback subsystems, power subsystems and/or thermal-management subsystems. Additionally, one or more of the subsystems may not be present in environmental monitoring device 200. Moreover, in some embodiments, environmental monitoring device 200 may include one or more additional subsystems that are not shown in FIG. 2. For example, environmental monitoring device 200 can include: one or more optional speakers 240 (and, more generally, a physiological output subsystem that provides sensory information to the user), one or more motors that rotate one or more color wheels (or color-wheel indicators) with low power consumption (such as a brushed motor, a brushless motor, a piezo-type ratcheting motor, etc.), and/or an alarm subsystem. Note that the one or more optional speakers 240 and a microphone may be used to provide audio conferencing capability to another electronic device. Furthermore, note that a given motor may rotate a color wheel using an open-loop control technique or a closed-loop control technique based on an encoder, such as: an optical encoder, a mechanical encoder, a potentiometer, etc. Although separate subsystems are shown in FIG. 2, in some embodiments, some or all of a given subsystem or component can be integrated into one or more of the other subsystems or components in environmental monitoring device 200. For example, in some embodiments the one or more program modules 238 are included in operating system 236. In some embodiments, a component in a given subsystem is included in a different subsystem, e.g., optional switch 244 may be included in optional user-interface subsystem 216.

Moreover, the circuits and components in environmental monitoring device 200 may be implemented using any combination of analog and/or digital circuitry, including: bipolar, PMOS and/or NMOS gates or transistors. Furthermore, signals in these embodiments may include digital signals that have approximately discrete values and/or analog signals that have continuous values. Additionally, components and circuits may be single-ended or differential, and power supplies may be unipolar or bipolar.

An integrated circuit may implement some or all of the functionality of networking subsystem 214 (such as a radio) and, more generally, some or all of the functionality of environmental monitoring device 200. Moreover, the integrated circuit may include hardware and/or software mechanisms that are used for transmitting wireless signals from environmental monitoring device 200 to, and receiving signals at environmental monitoring device 200 from other electronic devices. Aside from the mechanisms herein described, radios are generally known in the art and hence are not described in detail. In general, networking subsystem 214 and/or the integrated circuit can include any number of radios. Note that the radios in multiple-radio embodiments function in a similar way to the radios described in single-radio embodiments.

In some embodiments, networking subsystem 214 and/or the integrated circuit include a configuration mechanism (such as one or more hardware and/or software mechanisms) that configures the radio(s) to transmit and/or receive on a given communication channel (e.g., a given carrier frequency). For example, in some embodiments, the configuration mechanism can be used to switch the radio from monitoring and/or transmitting on a given communication channel to monitoring and/or transmitting on a different communication channel. (Note that 'monitoring' as used herein comprises receiving signals from other electronic devices and possibly performing one or more processing operations on the received signals, e.g., determining if the received signal comprises an advertising frame, a petition, a beacon, etc.)

While a communication protocol compatible with Zig-Bee® was used as an illustrative example, the described embodiments of environmental monitoring device 200 may use a variety of network or communication interfaces. Furthermore, while some of the operations in the preceding embodiments were implemented in hardware or software, in general the operations in the preceding embodiments can be implemented in a wide variety of configurations and architectures. Therefore, some or all of the operations in the preceding embodiments may be performed in hardware, in software or both. For example, at least some of the operations performed by processing subsystem 210 may be performed by sensor subsystem 218.

Figure 4:
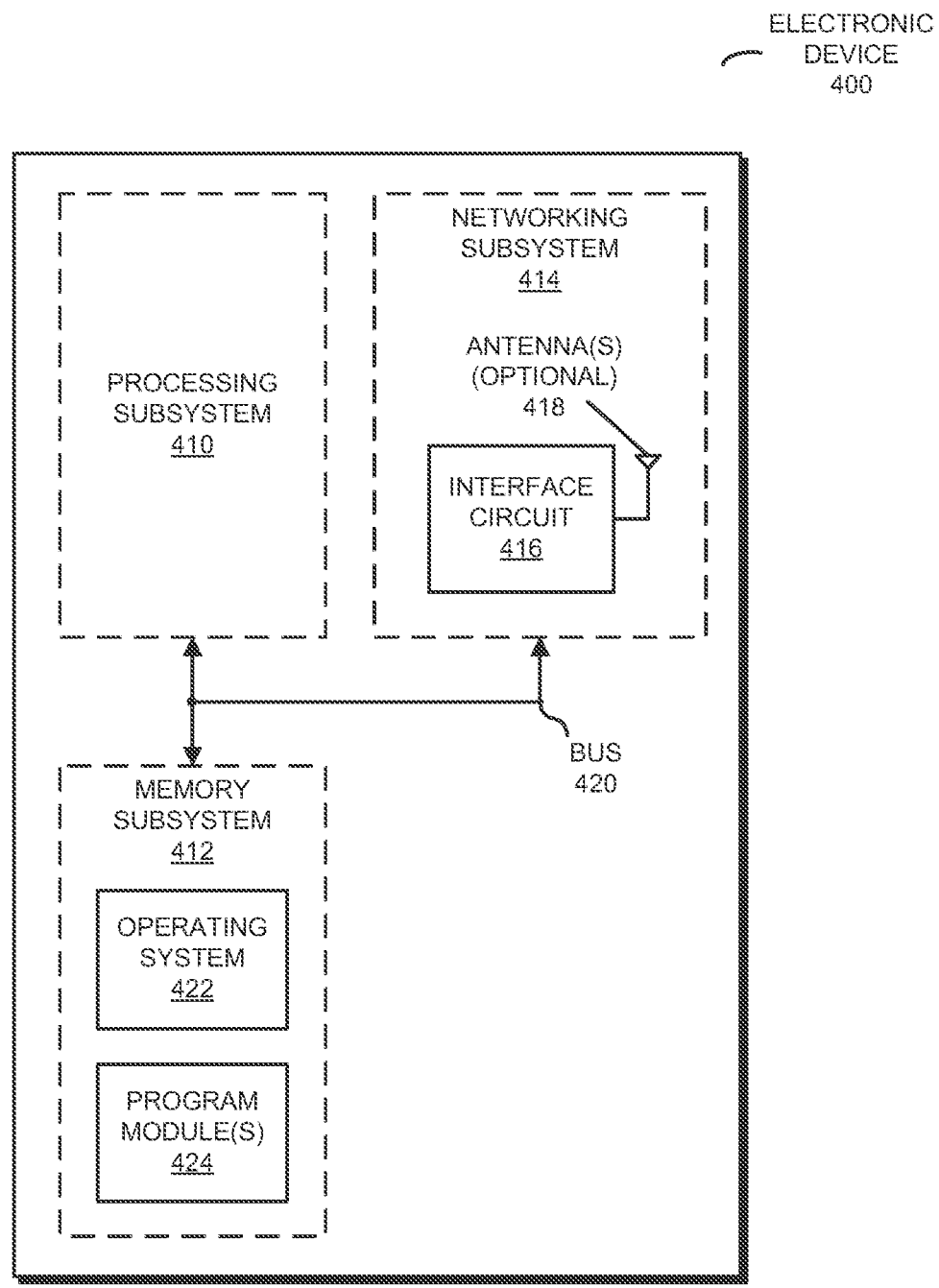
FIG. 4 is a block diagram illustrating an archive device of FIG. 1 in accordance with an embodiment of the present disclosure.

Furthermore, while the preceding discussion focused on the hardware, software and functionality in environmental monitoring device 200, archive device 116 (FIG. 1) and/or optional computer 120 (FIG. 1) may have the same or similar hardware (processors, memory, networking interfaces, etc.) and/or software to support the operations performed by these electronic devices or systems. This is shown in FIG. 4, which presents a block diagram illustrating electronic device 400, such as archive device 116 (FIG. 1). In particular, electronic device 400 includes processing subsystem 410, memory subsystem 412 and/or a networking subsystem 414. Processing subsystem 410 includes one or more devices configured to perform computational operations. For example, processing subsystem 410 can include one or more microprocessors, application-specific integrated circuits (ASICs), microcontrollers, programmable-logic devices, and/or one or more digital signal processors (DSPs).

Memory subsystem 412 includes one or more devices for storing data and/or instructions for processing subsystem 410 and/or networking subsystem 414. For example, memory subsystem 412 can include dynamic random access memory (DRAM), static random access memory (SRAM), and/or other types of memory. In some embodiments, instructions for processing subsystem 410 in memory subsystem 412 include: one or more program modules 424 or sets of instructions (such as an archiving application, an analysis application, a data-sharing application and/or a notification application), which may be executed in an operating environment (such as operating system 422) by processing subsystem 410. Note that the one or more computer programs may constitute a computer-program mechanism or a program module. Moreover, instructions in the various modules in memory subsystem 412 may be implemented in: a high-level procedural language, an object-oriented programming language, and/or in an assembly or machine language. Furthermore, the programming language may be compiled or interpreted, e.g., configurable or configured (which may be used interchangeably in this discussion), to be executed by processing subsystem 410.

In addition, memory subsystem 412 can include mechanisms for controlling access to the memory. In some embodiments, memory subsystem 412 includes a memory hierarchy that comprises one or more caches coupled to a memory in electronic device 400. In some of these embodiments, one or more of the caches is located in processing subsystem 410.

In some embodiments, memory subsystem 412 is coupled to one or more high-capacity mass-storage devices (not shown). For example, memory subsystem 412 can be coupled to a magnetic or optical drive, a solid-state drive, or another type of mass-storage device. In these embodiments, memory subsystem 412 can be used by electronic device 400 as fast-access storage for often-used data, while the mass-storage device is used to store less frequently used data. Note that memory subsystem 412 may include multiple storage devices at one or more locations. Thus, data storage by memory subsystem 412 may be distributed, such as a cloud-based data-storage system.

Networking subsystem 414 includes one or more devices configured to couple to and communicate on a wired, optical and/or wireless network (i.e., to perform network operations), including an interface circuit 416 and one or more optional antennas 418. For example, networking subsystem 414 can include: a ZigBee® networking subsystem, a Bluetooth™ networking system (which can include Bluetooth™ Low Energy, BLE or Bluetooth™ LE), a cellular networking system (e.g., a 3G/4G network such as UMTS, LTE, etc.), a USB networking system, a networking system based on the standards described in IEEE 802.11 (e.g., a Wi-Fi® networking system), an Ethernet networking system and/or another communication system.

Moreover, networking subsystem 414 includes processors, controllers, radios/antennas, sockets/plugs, and/or other devices used for coupling to, communicating on, and handling data and events for each supported networking or communication system. Note that mechanisms used for coupling to, communicating on, and handling data and events on the network for each network system are sometimes collectively referred to as a 'network interface' for the network system.

During operation of electronic device 400, processing subsystem 410 may execute one or more program modules 424, such as an archiving application. This archiving application may receive, via networking interface 414, data packets from one or more of environmental monitoring devices 110 (FIG. 1). These data packets may include sensor data and/or analyzed sensor data. In some embodiments, processing subsystem 410 executes an analysis application, which analyzes the received sensor data. For example, the received sensor data may be: time stamped for time-series processing, filtered, compressed, etc. In some additional embodiments, processing subsystem 410 executes an analysis application, which can compare received sensor data analysis from one or more of environmental monitoring devices 110 (FIG. 1).

Figure 5:
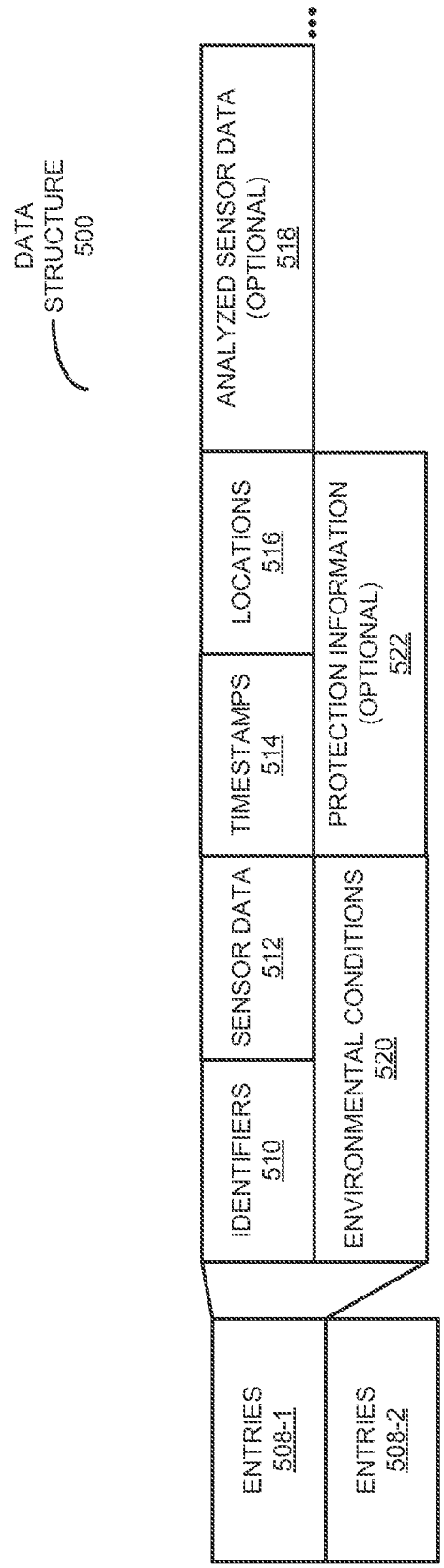
FIG. 5 is a block diagram illustrating a data structure with a historical record in the archive device of FIG. 4 in accordance with an embodiment of the present disclosure.

Then, archiving application may store the sensor data and/or the analyzed sensor data in a data structure in memory subsystem 412. This is shown in FIG. 5, which presents a block diagram illustrating data structure 500. In particular, data structure 500 may include entries 508 with: identifiers 510 of environmental monitoring devices, sensor data 512, timestamps 514, locations 516, optional analyzed sensor data 518, environmental conditions 520 and/or optional protection information 522.

Referring back to FIG. 4, in some embodiments the received data packets include protected information. For example, the sensor data and/or the analyzed sensor data may be encrypted using an encryption key associated with one of environmental monitoring devices 110 (FIG. 1) and/or a secure channel in the one of environmental monitoring devices 110 (FIG. 1). Alternatively or additionally, there may be a digital signature associated with the sensor data and/or the analyzed sensor data, and/or the sensor data and/or the analyzed sensor data may be protected using a secure hash function. In these embodiments, optional protection information 522 (FIG. 5) may include information that can confirm the source(s) of the received data packets (such as one or more of environmental monitoring devices 110 in FIG. 1) and/or can be used to unprotect the sensor data and/or the analyzed sensor data. Note that optional protection information 522 (FIG. 5) may be received, via networking interface 414, from one of environmental monitoring devices 110 (FIG. 1). This protection information may include the encryption key or an encryption key associated with the encryption key (which can be used to confirm the digital signature and/or decrypt encrypted information). Networking device 414 can utilize: encrypted tunneling in at least one networking interface, a network switch and/or network router between one of environmental monitoring devices 110 and archive device 116 in FIG. 1. Similarly, optional protection information 522 (FIG. 5) may specify the secure hash function, may include the identifier for one of environmental monitoring devices 110 (FIG. 1) and/or may include the random number (which also can be used to unprotect information). Note that protection information 522 may include fault tolerance information (such as parity bits or hashes) to aid in the detection of tampered data, corrupted data, and/or erroneous sensor readings in the event of a sensor failure or miscalibration.

In an exemplary embodiment, a public-private encryption-key technique is used. In particular, a certified, secure data package may be signed by one of environmental monitoring devices 110 (FIG. 1) using a public encryption key of archive device 116 (FIG. 1), and the digital signature may be verified and the certified, secure data package may be decrypted using the private encryption key of archive device 116 (FIG. 1). However, in other embodiments a symmetric encryption technique is used. Thus, the same encryption key may be used to sign, encrypt and/or decrypt the certified, secure data package.

In some embodiments, the one or more program modules 424 includes a data-sharing application. This data-sharing application may receive, via networking subsystem 414, authorization information for a recipient of sensor data and/or analyzed sensor data. In response to the authorization information, the data-sharing application may provide, via networking subsystem 414, the requested sensor data and/or analyzed sensor data to the recipient. Alternatively, the data-sharing application may provide, via networking subsystem 414, a pointer to a location in memory subsystem 412 where the recipient can access the requested sensor data and/or analyzed sensor data. Note that the data-sharing application may also optionally provide the optional protection information 522 (FIG. 5) to the recipient (which may allow the recipient to confirm the source(s) and/or to unprotect protected information).

Additionally, in some embodiments the one or more program modules 424 includes a notification application. This notification application may receive, via networking subsystem 414, information, such as feedback associated with one or more environmental conditions in environment 112 (FIG. 1) and/or a notification (such as a maintenance notification). In response, the notification application may communicate, via networking subsystem 414, the information and/or one or more reports based on the information (such as daily, weekly or monthly summaries of analyzed sensor data, which may be included in documents or files) to: one or more of environmental monitoring devices 110 (FIG. 1), data-sharing electronic device 118 (FIG. 1) and/or other electronic devices (such as computers or servers associated with or operated on behalf of: component suppliers, retailers, insurance companies, maintenance organizations, shipping companies, landlords or property owners, a corporate-compliance organization, inspectors, businesses, government agencies, etc.). For example, the communication of the information may utilize a Short Message Service, email, a social network and/or a message service with a restricted number of characters per message. Alternatively, the information may be posted to a web page or website (and, more generally, a location on a network), and one or more recipients may be notified via networking subsystem 414, e.g., a link to the location may be provided to the recipients.

When the notification includes a maintenance notification, the archiving application may store information specifying the maintenance notification in a historical record or log for the environment. In addition, the archiving application may store any subsequent remedial action (such as a repair or service performed on an electronic device in the environment) in a historical record or log for the environment in memory subsystem 412.

Within electronic device 400, processing subsystem 410, memory subsystem 412, and/or networking subsystem 414 may be coupled using one or more interconnects, such as bus 420. These interconnects may include an electrical, optical, and/or electro-optical connection that the subsystems can use to communicate commands and data among one another. Note that different embodiments can include a different number or configuration of electrical, optical, and/or electro-optical connections among the subsystems.

Electronic device 400 can be (or can be included in) any electronic device with at least one network interface. For example, electronic device 400 can be (or can be included in): a sensor (such as a smart sensor), a tablet computer, a smartphone, a cellular telephone, an appliance, a regulator device, a consumer-electronic device, a portable computing device, test equipment, a digital signal processor, a controller, a personal digital assistant, a facsimile machine, a laser printer (or other office equipment such as a photocopier), a personal organizer, a toy, a set-top box, a computing device (such as a laptop computer, a desktop computer, a server, and/or a sub-notebook/netbook), an alarm, a light (such as a nightlight), a monitoring device, and/or another electronic device.

Although specific components are used to describe electronic device 400, in alternative embodiments, different components and/or subsystems may be present in electronic device 400. For example, electronic device 400 may include one or more additional processing subsystems, memory subsystems, and/or networking subsystems. Additionally, one or more of the subsystems may not be present in electronic device 400. Moreover, in some embodiments, electronic device 400 may include one or more additional subsystems that are not shown in FIG. 4, such as a power supply and/or a user-interface subsystem (which a user may use to modify settings of one or more of environmental monitoring devices 110 in FIG. 1, such as settings for alarms or notifications). Although separate subsystems are shown in FIG. 4, in some embodiments, some or all of a given subsystem or component can be integrated into one or more of the other subsystems or components in electronic device 400. For example, in some embodiments the one or more program modules 424 are included in operating system 422.

Moreover, the circuits and components in electronic device 400 may be implemented using any combination of analog and/or digital circuitry, including: bipolar, PMOS and/or NMOS gates or transistors. Furthermore, signals in these embodiments may include digital signals that have approximately discrete values and/or analog signals that have continuous values. Additionally, components and circuits may be single-ended or differential, and power supplies may be unipolar or bipolar.

Note that an integrated circuit may implement some or all of the functionality of electronic device 400.

While some of the operations in the preceding embodiments were implemented in hardware or software, in general the operations in the preceding embodiments can be implemented in a wide variety of configurations and architectures. Therefore, some or all of the operations in the preceding embodiments may be performed in hardware, in software or both.

Figure 6:
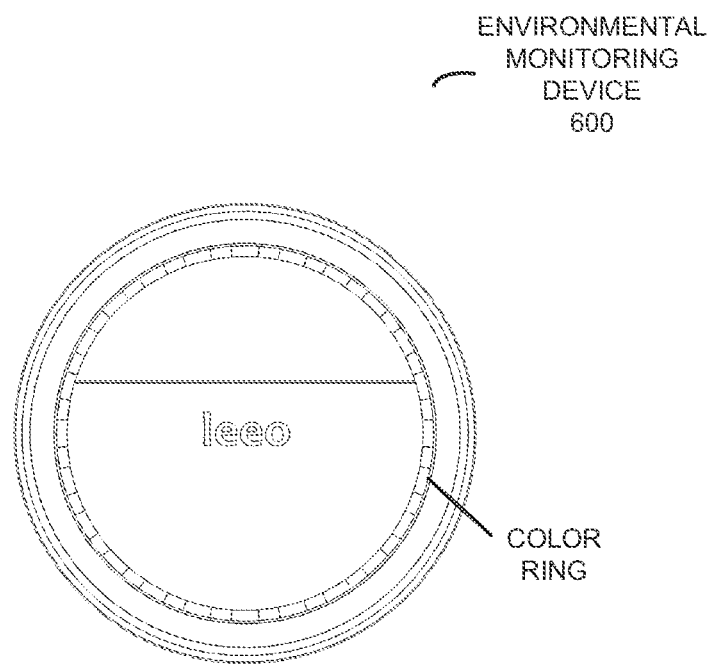
FIG. 6 is a drawing illustrating a front view of an environmental monitoring device in FIG. 1 in accordance with an embodiment of the present disclosure.
Figure 7:
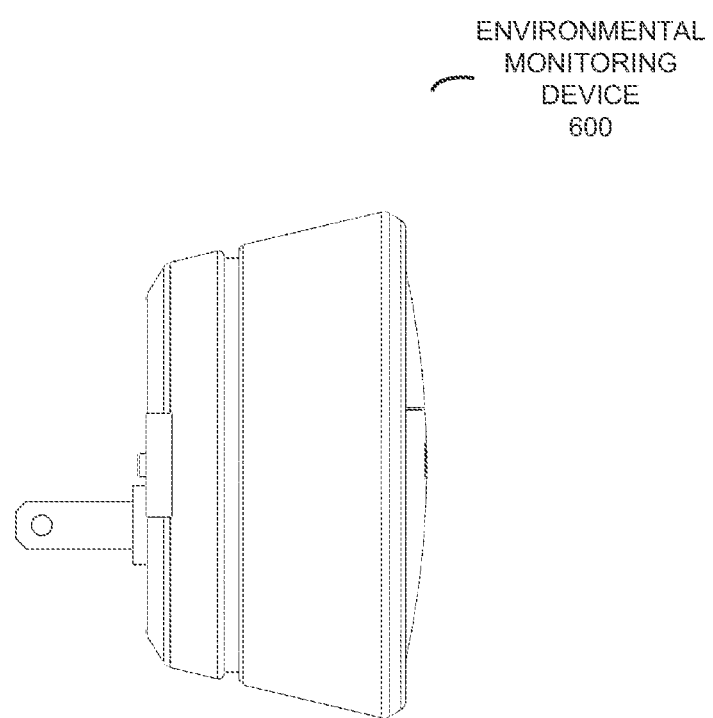
FIG. 7 is a drawing illustrating a side view of the environmental monitoring device in FIG. 6 in accordance with an embodiment of the present disclosure.
Figure 8:
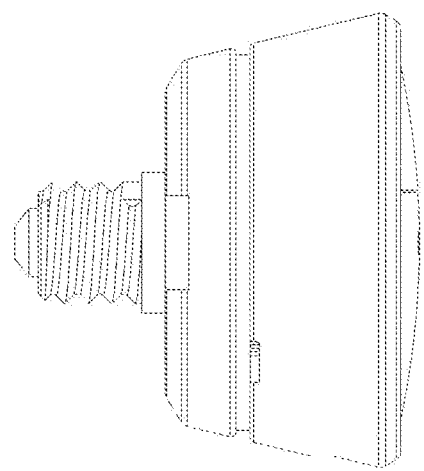
FIG. 8 is a drawing illustrating a side view of the environmental monitoring device in FIG. 6 in accordance with an embodiment of the present disclosure.

An exemplary embodiment of the environmental monitoring device is shown in FIGS. 6-8, which respectively show front, and side views of environmental monitoring device 600, which may be one of environmental monitoring devices 110 (FIG. 1). Alternatively, the environmental monitoring device may include a display. This shown in FIGS. 9 and 10, which respectively show front and side views of environmental monitoring device 900, which may be one of environmental monitoring devices 110 (FIG. 1).

Embodiments of the environmental monitoring device may include a grating in the chassis or housing (such as a case or a shell on the outside of the environmental monitoring device) that prevents large particles, soil and mud from damaging or otherwise obscuring inputs to one or more sensor devices in the environmental monitoring device. Alternatively or additionally, as described further below with reference to FIGS. 20 and 21, the chassis or housing may facilitate airflow or fluid flow through vents or openings to one or more sensor devices in the environmental monitoring device. In addition, as noted previously, the environmental monitoring device may include a forced-fluid driver (such as a fan) to facilitate airflow or fluid-flow through the vents. However, in other embodiments airflow or fluid flow is facilitated using convection (e.g., by heating the air or the fluid), or the airflow or fluid flow may occur passively.

Figure 11:
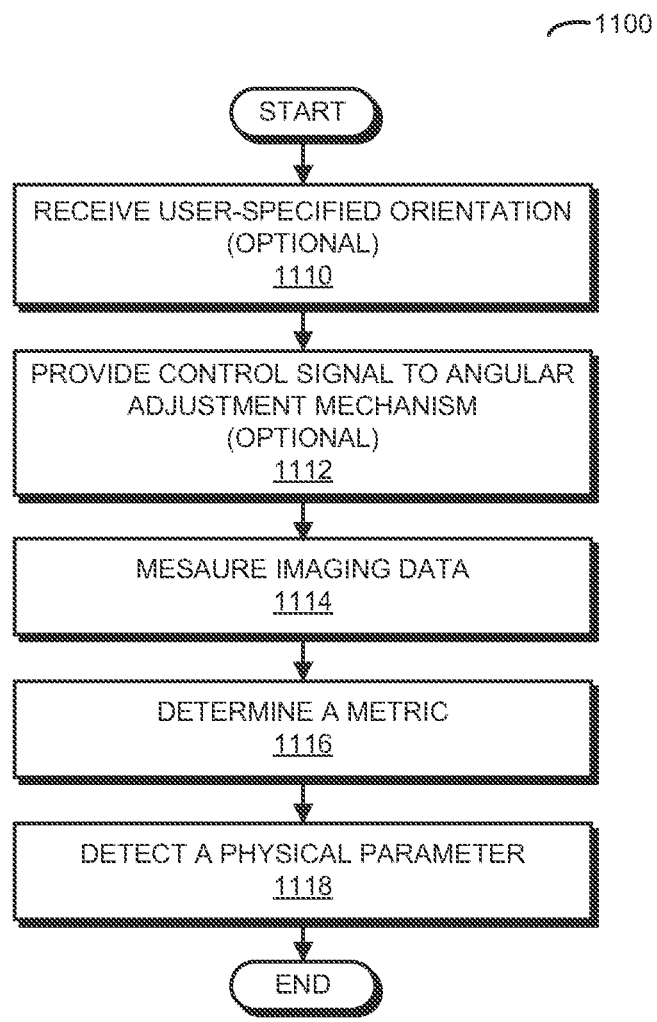
FIG. 11 is a flow diagram illustrating a method for determining a metric in accordance with an embodiment of the present disclosure.

We now further describe operation of the environmental monitoring device and, in particular, functionality of the environmental monitoring device in various embodiments. FIG. 11 presents a flow diagram illustrating a method 1100 for determining a metric, which may be performed by an imaging device in the environmental monitoring device. During operation, the imaging device may measure imaging data (operation 1114) for an external environment that includes the environmental monitoring device, where the imaging device has different spatial (or directional) sensitivity in different regions of the external environment, and the different spatial sensitivity in the different regions defines a field of view of the imaging device. For example, the imaging device may include a lens that provides the different spatial sensitivity. This lens may include a predefined distortion that provides the different spatial sensitivity (such as different magnifications for the different regions). In particular, the lens may include: a Fresnel lens, a cylindrical lens, lenticular lens, gradient index lens, etc. In some embodiments, the lens has: a circular shape, a cross shape, or a rectangular shape. Moreover, the lens may be symmetrical or non-symmetrical, and it may be adjusted, distorted, cut, processed, arranged, customized or otherwise adapted to provide the different spatial sensitivity and/or to accommodate abnormalities or limitations of a sensor device in the environmental monitoring device.

In an exemplary embodiment, the lens includes a set of concentric circles or ellipses with a common center. Alternatively or additionally, the lens has a cross shape. In some embodiments, the lens has a distorted cross shape, in which one arm is longer than the other (e.g., the cross may appear as if it were on a curved surface when it is on a flat surface). This distorted shape may optimize sensor data received from the sensor device. Note that a cover for the lens may have an outer shape that matches the contours of the outer front face of a chassis or housing of the environmental monitoring device. Moreover, the lens may be formed on the interior surface of a lens piece so that the lens is not clearly visible from the exterior of the environmental monitoring device.

Then, the imaging device may determine the metric (operation 1116) based on the imaging data. For example, determining the metric may involve computing: a difference vector between two images in the field of view that were acquired at different times, a difference in the light intensity between two images in the field of view that were acquired at different times, a histogram of the light intensity in pixels in the field of view, a Fourier transform of an image in the field of view, etc.

Next, a processor in the environmental monitoring device may detect a physical parameter (operation 1118) based on the metric. This physical parameter may include: motion of an object in the field of view; a light scattering pattern in the field of view; and/or a light intensity in the field of view. For example, the metric may be compared to a threshold value, and the physical parameter may be detected based on the comparison. Thus, if the metric includes a normalized difference vector or a normalized difference in the light intensity with a magnitude that exceeds a threshold value of 0.25 or 0.5, the motion of the object may be detected. In general, the environmental monitoring device may detect the physical parameter based on: an image, video, and motion sensors that detect changing patterns in the scattering of light.

In some embodiments, the processor in the environmental monitoring device optionally receives a user-specified orientation (operation 1110). Then, the processor may optionally provide a control signal to an angular adjustment mechanism (operation 1112) in response to the user-specified orientation. This control signal may change the orientation of the field of view by selectively rotating the angular adjustment mechanism about an axis. For example, the angular adjustment mechanism may include a motor, such as a stepper motor. Alternatively, the angular adjustment mechanism may include a MEMS mirror that can be adjusted to scatter or reflect light (such as laser light) over a wide range of angles. Note that the processor may execute a program module that includes instructions for operations 1110 and 1112.

While the preceding example illustrated automated control of the angular adjustment mechanism, in other embodiments the orientation may be changed manually. For example, the angular adjustment mechanism may have a stationary position and an adjustment position along the axis. In the stationary position, the angular adjustment mechanism may have a fixed orientation. However, in the adjustment position, the angular adjustment mechanism may selectively rotate about the axis (such as in 5° increments). Furthermore, instead of responding to the control signal, the angular adjustment mechanism may displace from the stationary position to the adjustment position in response to an external force or torque applied to the angular adjustment mechanism. In particular, a user of the environmental monitoring device may apply the external force or torque (e.g., by pushing in on a front face of the environmental monitoring device and rotating to the desired orientation). In some embodiments, a user changes the spatial sensitivity by changing the imaging device (such as by attaching a different lens to the environmental monitoring device).

In these ways, the environmental monitoring device may facilitate more accurate or focused monitoring of at least some of the different regions (or a portion of the external environment) relative to a remainder of the regions (or a remainder of the external environment). For example, the environmental monitoring device may be more focused on a region directly in front of the environmental monitoring device, while at other times a wider field of view may be used. Alternatively, the environmental monitoring device may be more sensitive to an up and a down direction.

Figure 12:
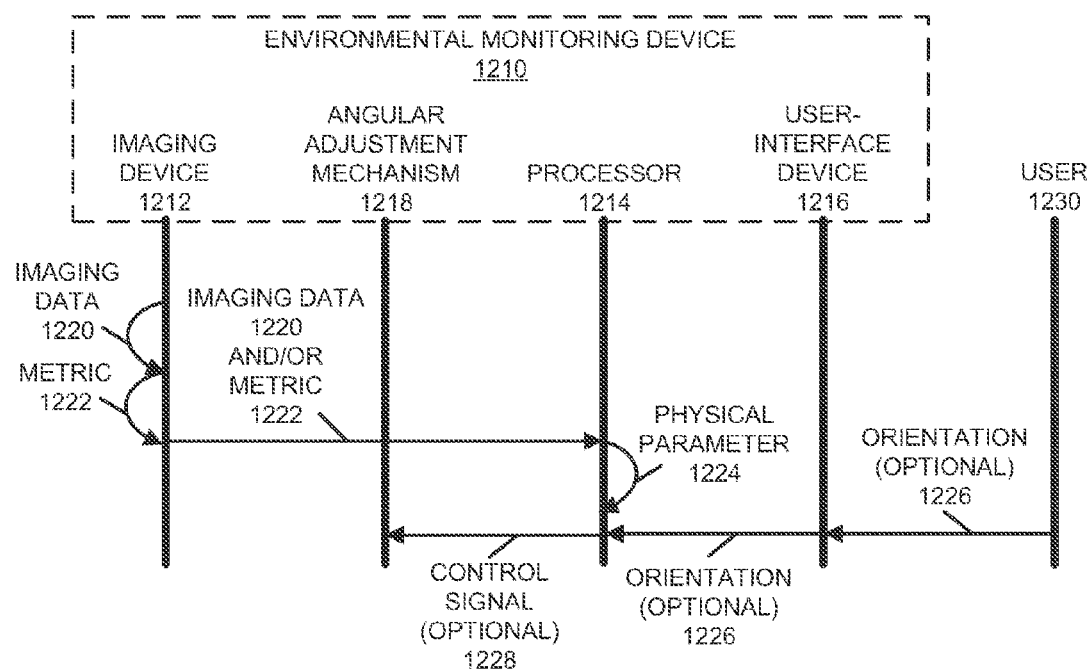
FIG. 12 is a drawing illustrating communication within an environmental monitoring device during the method of FIG. 11 in accordance with an embodiment of the present disclosure.

FIG. 12 presents a drawing illustrating communication within environmental monitoring device 1210 during method 1100 (FIG. 11). During operation of environmental monitoring device 1210 (such as during a motion-sensing mode of operation), imaging device 1212 may measure imaging data 1220 for the external environment with the different spatial sensitivity in the different regions that defines the field of view. Then, imaging device 1212 may determine metric 1222 based on imaging data 1220.

Next, imaging device 1212 may provide imaging data 1220 and/or metric 1222 to processor 1214. Moreover, processor 1214 may detect a physical parameter 1224 based on metric 1222.

In some embodiments, processor 1214 optionally receives a user-specified orientation 1226 from a user 1230 via user-interface device 1216. Then, processor 1214 may optionally provide a control signal 1228 to angular adjustment mechanism 1218 in response to user-specified orientation 1226 to change the orientation of the field of view by selectively rotating the angular adjustment mechanism about the axis.

Figure 13:
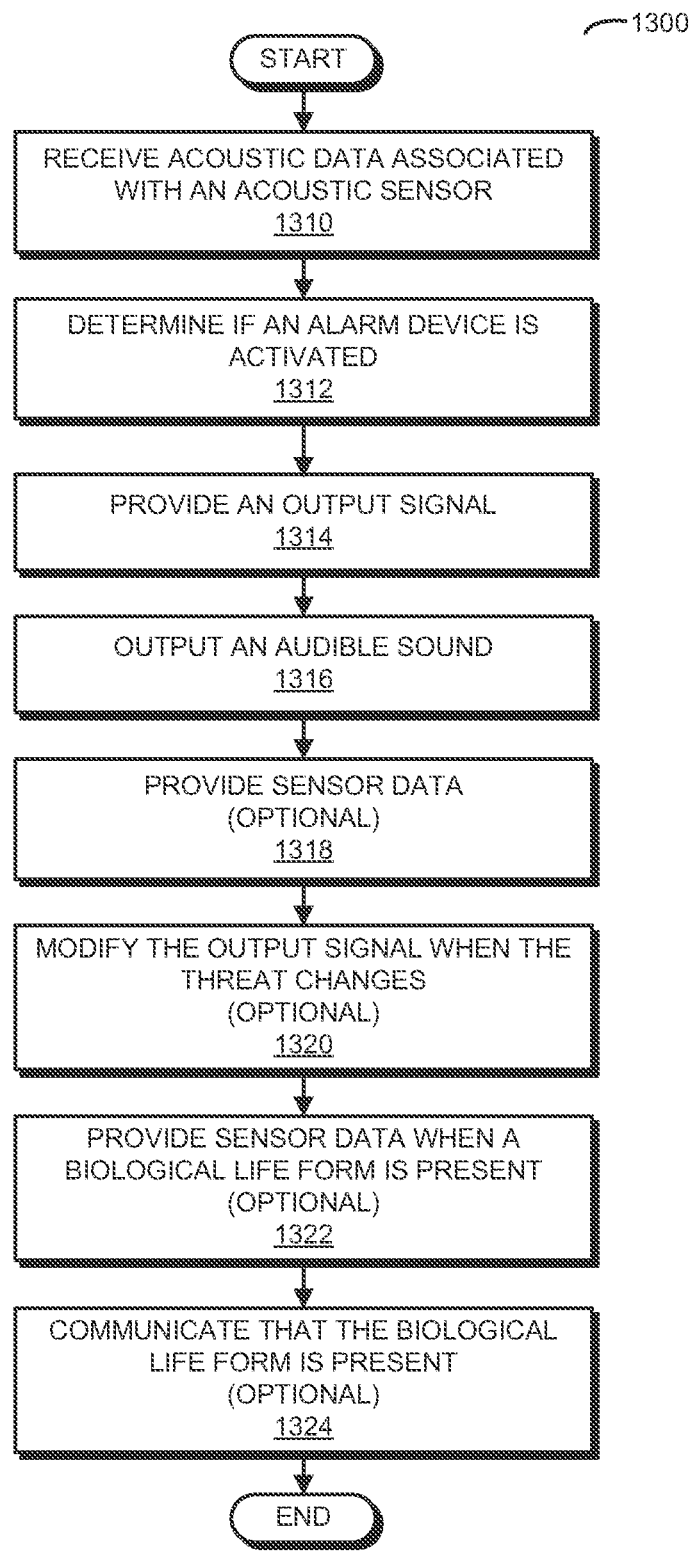
FIG. 13 is a flow diagram illustrating a method for determining if an alarm device is activated in accordance with an embodiment of the present disclosure.

In some embodiments, the environmental monitoring device supplements or assists the functioning of an alarm device in an external environment. This is shown in FIG. 13, which presents a flow diagram illustrating a method 1300 for determining if an alarm device is activated. Method 1300 may be performed by a processor in the environmental monitoring device. For example, the processor may execute a program module that includes instructions for operations in method 1300. During operation, the processor may receive (or access) acoustic data (or analyzed acoustic data) associated with an acoustic sensor (operation 1310) in the environmental monitoring device, where the acoustic data is based on measurements of a sound in an external environment that includes the environmental monitoring device. For example, the acoustic data may include a sound intensity in a frequency band or within the bandwidth of a filter (such as audible frequencies, or frequencies less than 2, 5, 10 or 20 kHz). Alternatively, the acoustic data may include an acoustic spectrum and/or time intervals between tones in the sound. In general, the acoustic data may include or be associated with: an alarm, a detector, a human voice, music, a vibration, an automobile noise (such as a car pulling into a garage), water dripping, wind blowing through an open window (or a broken window), a door, a tea kettle whistling, and/or wall.

Then, the processor may determine if the alarm device, which is separate from the environmental monitoring device (and may not communicate with and/or may not have electrical coupling to the environmental monitoring device), is activated (operation 1312) based on the acoustic data. For example, the alarm device may include a smoke detector, and the processor may determine if the smoke detector is activated based on a temporal 3 acoustic pattern that is compatible with an American National Standards Institute standard S3.42 1990.

Moreover, the processor may provide an output signal (operation 1314) that indicates the alarm device is activated, and one or more speakers (or audio transducers) in the environmental monitoring device may output audible sound (operation 1316) in the external environment based on the output signal. For example, the audible sound may include an alarm at one or more frequencies within the human-hearing range or a verbal warning message (such as 'warning: smoke detected').

Next, a sensor device in the environmental monitoring device may optionally provide sensor data (operation 1318) based on measurements of an environmental condition in the external environment. For example, the sensor data may indicate the concentration of a chemical compound, the temperature or the amount of particulate matter in the environment. In response to the sensor data, the processor may optionally assess a degree of threat in the external environment and may optionally modify the output signal when the threat changes (operation 1320). Furthermore, the one or more speakers may change the audible sound based on the modified output signal. This change to the audible sound may provide quantitative feedback about the degree of the threat (as opposed to a binary response, such as providing or not providing an alert). In particular, the change in the audible sound may include: an increase in the sound intensity, a change in the sound frequency (such as an increasing frequency), a change in the time interval between tones (such as a decreasing time interval), a change in a verbal warning (such as transitioning from 'warning: unhealthy air quality has been detected' to 'emergency: the air quality in this room is life-threatening, evacuate immediately'), etc.

Figure 9:
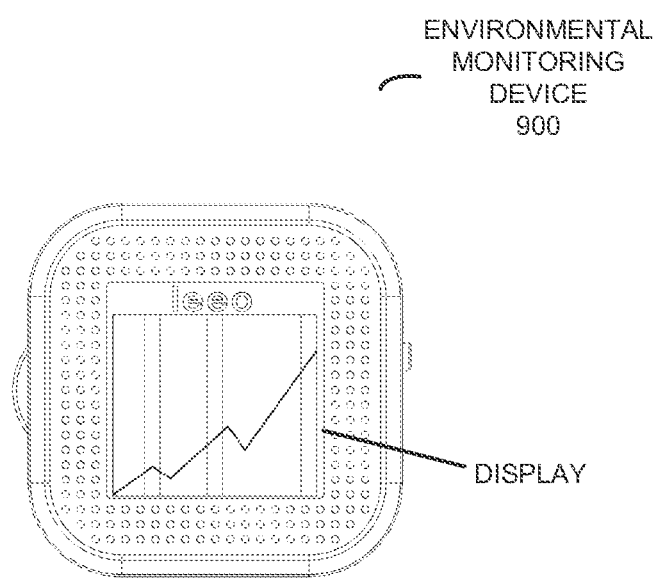
FIG. 9 is a drawing illustrating a front view of an environmental monitoring device in FIG. 1 in accordance with an embodiment of the present disclosure.
Figure 10:
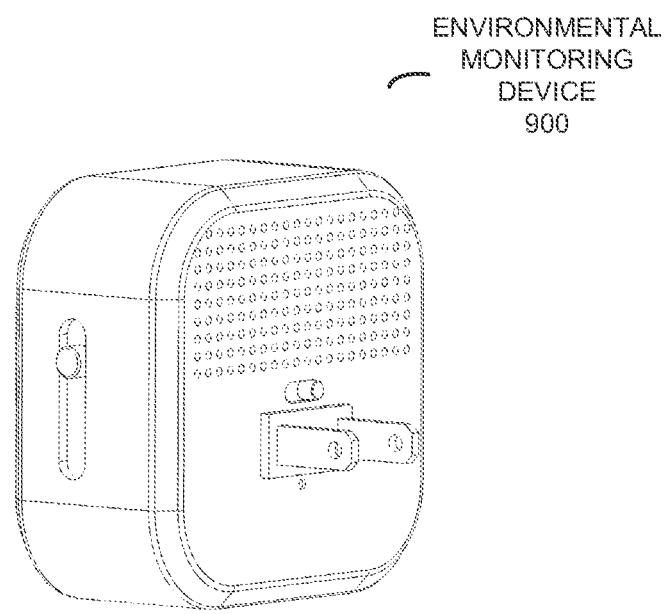
FIG. 10 is a drawing illustrating a side view of the environmental monitoring device in FIG. 9 in accordance with an embodiment of the present disclosure.

While the preceding discussion used audio feedback about the environmental condition in the environment, more generally the environmental monitoring device may also provide other types feedback about one or more environmental conditions in the environment. As shown in FIG. 9, in some embodiments the environmental monitoring device displays a graph (such as: a pie chart, a bar chart, a scatter plot, a time-series plot, a tabular summary, a spectrum, a spectrogram and/or another type of graphical analysis) to provide the user with information about the one or more environmental conditions. Alternatively or additionally, the graph may include images of chemicals, along with color scales or numbers. The image of a given chemical can grow or shrink in size in proportion to the chemical levels or concentrations detected. These images may offer information about relative health or safety of the environment, and/or may be of general interest.

In some embodiments, the feedback is provided via a color-wheel indicator that is rotated by a motor based on a signal that indicates the strength of an environmental condition or using a color-wheel graphic. For example, an indicator or a marker aligned with the color-wheel indicator may indicate which area in the color wheel corresponds to the current environmental condition. Alternatively, as shown in FIG. 6, a color-wheel indicator may include a rotatable or selectively illuminated dial or ring (which is sometimes referred to as a 'color ring') with a band of color or shades of grayscale on the outside of the color wheel so that a user can identify the approximate level of environmental condition based on the color(s) or grayscale values displayed on the ring. In another display option, the color-wheel indicator may include a color or texture-based gauge. Furthermore, the environmental monitoring device may include multiple color-wheel indicators in the feedback subsystem that can be used together to display additional information, or to provide additional resolution and/or precision to the feedback. In an exemplary embodiment, a transparent color wheel with additional colors may be rotated (possibly at a different angular velocity from other color wheels) to modify the colors presented. Similarly, shades of gray or transparent gradients of increasing opacity of red, green, and/or blue (or cyan, magenta, and/or yellow) may be used around the ring of a given color wheel.

In an exemplary embodiment, the feedback includes different types of audio feedback or alarms. For example, the environmental monitoring device may emit sound in a range from 1 to 1000 decibels, and may emit audio at different volumes at different times. For example, the environmental monitoring device may include a piezoelectric buzzer and/or a speaker. The piezoelectric buzzer may beep three times at a volume level of 60-120 decibels within a range of 5-200 feet (such as at 85 decibels within a range of 10 feet). Then, the speaker may emit a prerecorded message instructing residents to leave a home or office at a volume level of 60-120 decibels. Moreover, the environmental monitoring device may repeat this pattern if the sensor device detects a smoke concentration or a carbon-monoxide concentration above a predetermined threshold value and may sound continuously at a volume level of 60-120 decibels with a range of 5-200 feet (such as 85 decibels within a range of 10 feet). Alternatively or additionally, the environmental monitoring device may provide an alarm using a mechanical beeper that sounds at 60-230 decibels within a range of 5-200 feet (such as 105 decibels within a range of 10 feet) if the sensor device detects combustible gas concentration above a predetermined threshold. Furthermore, if the environmental monitoring device detects food being burned in the kitchen, the environmental monitoring device may notify a human using a tone emitted from a microphone before a piezoelectric buzzer sounds or provides the temporal 3 acoustic pattern.

In these ways, the environmental monitoring device may support the function of the alarm device, both is sounding the alarm and in providing more detailed and actionable information for individual's in the environment. For example, the sensor device may include a smoke detector and the alarm device may include a carbon-monoxide detector. Alternatively, the sensor device may include a carbon-monoxide detector and the alarm device may include a smoke detector.

Additionally, the sensor device may optionally provide sensor data when a biological life form is present (operation 1322) in the external environment, and an interface circuit in a networking subsystem in the environmental monitoring device may optionally communicate that the biological life form is present (operation 1324) to an electronic device in response to another output signal from the processor, where the processor may determine if the biological life form is present in the external environment based on the sensor data, and may provide the output signal if the alarm device is activated and the biological life form is present. For example, the sensor data may include motion information (such as an echo in response to a radar pulse), an infrared signature of the biological life form, Doppler information associated with the biological life form (such as a Doppler shift associated with breathing) and/or an audible distress tone or distress call broadcast by a first responder (such as a fireman). Note that the interface circuit may communicate a location of the environmental monitoring device to the electronic device in response to the output signal.

This capability may allow the environmental monitoring device to alert firemen and/or other first responders to the location of the biological life form and/or to the physiological condition of the biological life form in the event of an emergency in the environment (such as a fire, the presence of a noxious chemical or the presence of carbon monoxide). For example, the environmental monitoring device may be able to detect a child or a pet in a burning home, and may be able to direct rescuers to their location to facilitate a faster, less risky and/or more efficient rescue. Alternatively or additionally, if a fireman is injured or in distress and issues a Mayday call, the environmental monitoring device may detect this information and may relay it to other fireman to assist in getting prompt aid for the fireman.

Figure 14:
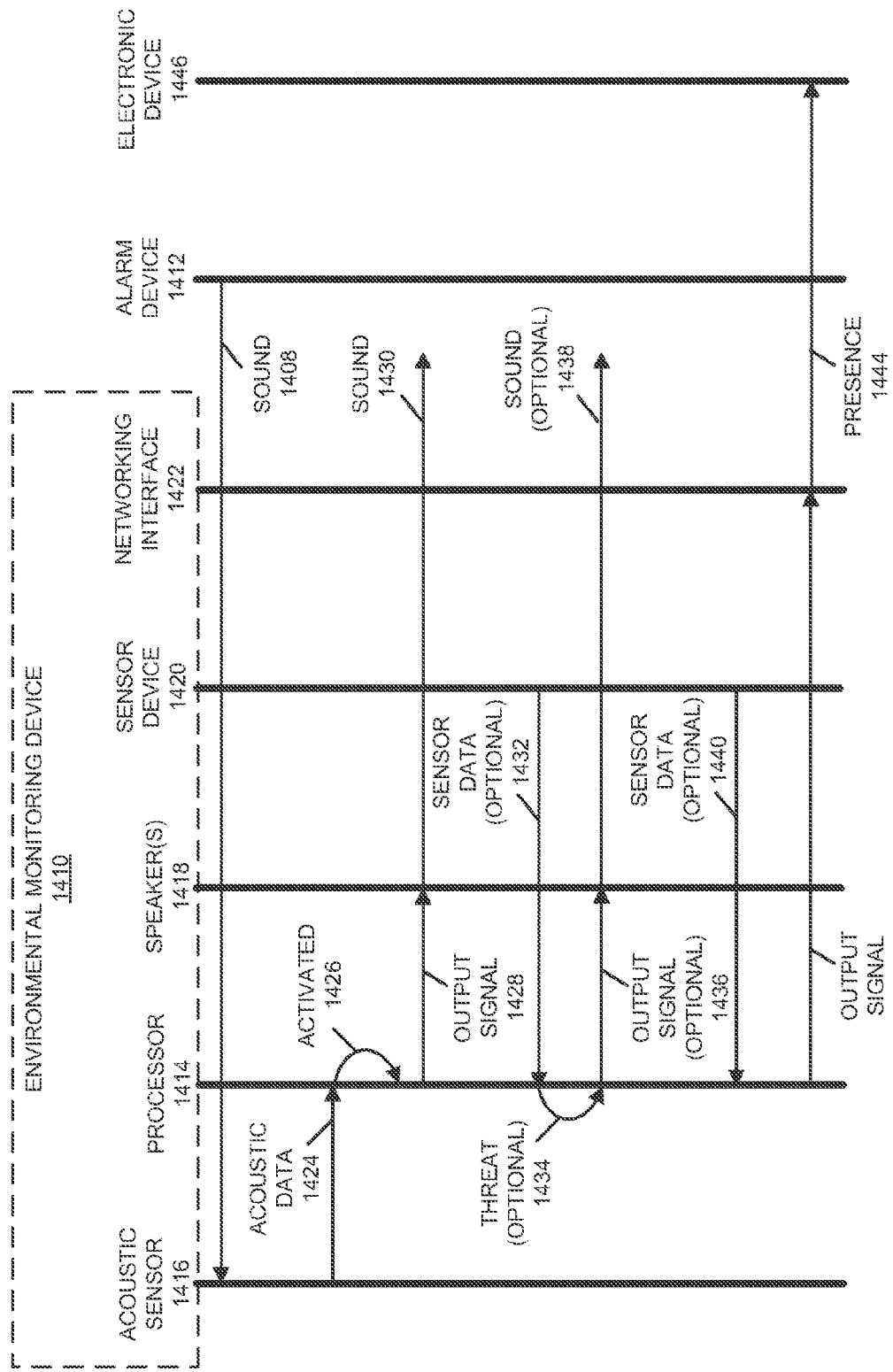
FIG. 14 is a drawing illustrating communication between an environmental monitoring device and the alarm device during the method of FIG. 13 in accordance with an embodiment of the present disclosure.

FIG. 14 presents a drawing illustrating communication between environmental monitoring device 1410 and alarm device 1412 during method 1300 (FIG. 13). During operation of environmental monitoring device 1410, processor 1414 may receive acoustic data 1424 from acoustic sensor 1416 based on the sound 1408 in the external environment from alarm device 1412. Then, processor 1414 may determine if alarm device 1412 is activated 1426.

Moreover, processor 1414 may provide an output signal 1428 that indicates alarm device 1412 is activated, and one or more speakers 1418 may output audible sound 1430 in the external environment based on output signal 1428. Next, a sensor device 1420 may optionally provide sensor data 1432 to processor 1414 based on measurements of the environmental condition in the external environment. In response to sensor data 1432, processor 1414 may optionally assess a degree of threat 1434 in the external environment and may optionally provide modified output signal 1436 when the threat changes. Furthermore, the one or more speakers 1418 may provide changed audible sound 1438 based on modified output signal 1436.

Additionally, sensor device 1420 may optionally provide sensor data 1440 when a biological life form is present in the external environment. An interface circuit in a networking subsystem 1422 may optionally communicate that the biological life form is present 1444 to an electronic device 1446 in response to output signal 1442 from processor 1414.

Figure 15:
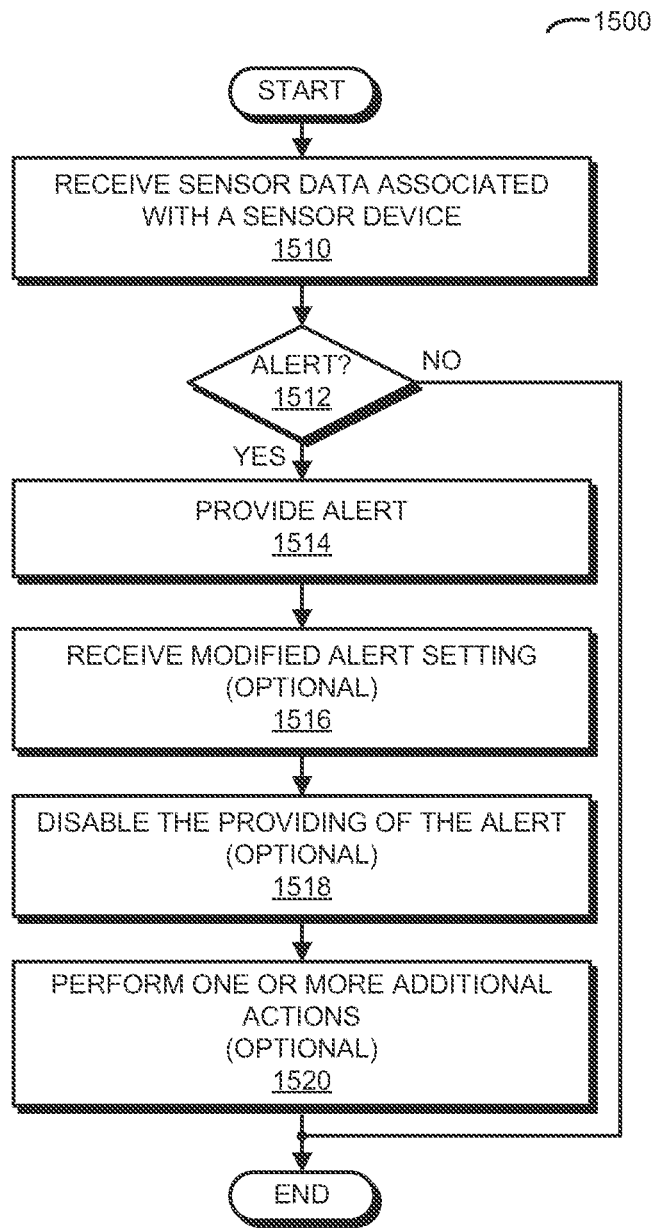
FIG. 15 is a flow diagram illustrating a method for providing an alert based on an alert setting in accordance with an embodiment of the present disclosure.

In some embodiments, operation of the environmental monitoring device may be remotely configured. This is shown in FIG. 15, which presents a flow diagram illustrating a method 1500 for providing an alert based on an alert setting, which may be performed by a processor in the environmental monitoring device. For example, the processor may execute a program module that includes instructions for operations in method 1500. During operation, the processor may receive (or access) sensor data (or analyzed sensor data) associated with a sensor device (operation 1510) based on measurements of an environmental condition in an external environment that includes the environmental monitoring device.

Then, the processor, assesses (operation 1512) if the environmental condition indicates a threat. If no, method 1500 ends. Otherwise, the processor provides the alert (operation 1514) to an electronic device, which is separate from the environmental monitoring device (and may not communicate with and/or may not have electrical coupling to the environmental monitoring device), based on the alert setting (which may specify when or the requirements for an alert to be communicated and how the alert is communicated, such as: an audible alarm having a tone and a volume setting, a Short Message Service, email, a social network, a messaging service with a restricted number of characters per message, a telephone call, etc.). For example, the processor may provide an output or a control signal to a networking interface that, in response, wirelessly communicates the alert to the electronic device (such as a cellular telephone of a user or owner of the environmental monitoring device.) This capability may enable remote monitoring of the environment, such as while the user runs errands or is travelling. Note that the alert may include information quantifying a degree of the threat, such as a concentration of a chemical or a level of risk to individuals in the external environment. In some embodiments, the processor also provides the alert in the external environment. In particular, the processor may provide an output or a control signal to one or more speakers, which output an audible sound in the external environment.

Separately or additionally, the environmental monitoring device may receive, from the electronic device, the modified alert setting and optionally a (separate) control command (operation 1516). For example, the modified alert setting and the option control command may be wirelessly received from the user. In response, the processor disables the providing of the alert (operation 1518) based on the modified alert setting and the optional control command. Note that the control command, such as a code, a safe word or a password, may help prevent accidental or unintended disabling of the alerts.

Furthermore, the processor may optionally perform one or more additional actions (operation 1520). For example, the processor may assess the threat after receiving the modified alert setting and may reactivate the providing of the alert if the threat continues to increase. Alternatively or additionally, the processor may revert from the modified alert setting to the alert setting after a time interval (such as 5, 10, 15 or 30 minutes).

While the previous embodiments illustrated remote disabling of alerts (and, more generally, remote configuration of the alert setting and/or operation of the environmental monitoring device, including an operating mode of the environmental monitoring device), in other embodiments the user may disable the alert based on an action performed in the environment. For example, the sensor device in the environmental monitoring device may provide additional sensor data based on monitoring of a user command and an optional (separate) control command in the external environment (such as a sound, a verbal instruction or command, a gesture, a sequence of bodily motions, a facial expression, etc.). Note that the control command may include a safe word, a password or a security code that is spoken by the user or that is provided by the user via a user interface. In response to receiving the additional sensor data and the optional control command, the processor may disable the providing of the alert. Alternatively or additionally, the processor may disable the providing of the alert when the user activates or changes the position of a switch in a feedback subsystem in the environmental monitoring device. Note that the switch may be a physical switch, knob or dial, or a virtual switch (or a user-interface object or icon) that is presented on a display in the environmental monitoring device.

Furthermore, while the previous embodiments illustrated remote modification of the alert setting, in some embodiments the user modifies the alert setting by interacting with a user interface (such as a user-interface object or icon and, more generally, a selection mechanism) in the feedback subsystem that allows the user to select the type of alert or feedback (including disabling alerts). For example, a selection box or a slider bar may allow the user to select options or settings such as: basic, intermediate or advanced feedback (depending on the technical level of the user or the application of the environmental monitoring device). The user may also use a user interface in the environmental monitoring device and/or the display to select feedback and notification options or settings, such as: the danger alarms and alerts, threshold values for detecting environmental conditions (such an environment-specific threshold values, which may be calibrated based on a history of an environment), optimal settings for a particular environmental monitoring device or environment (such as calibration settings, power-consumption settings, etc.) or a generic environmental monitoring device or environment, etc. Alternatively, the thresholds may be determined based on sensor data and/or environmental conditions associated with multiple environmental monitoring devices, e.g., using a supervised learning technique (such as support vector machines, classification and regression trees, a neural network, regression analysis, Bayesian analysis, etc.). Note that the environmental monitoring device may also display and/or provide to the electronic device operating information, such as: sensor life, uptime, battery life remaining, network connectivity, danger alarms enabled or disabled, and/or status messages.

Figure 16:
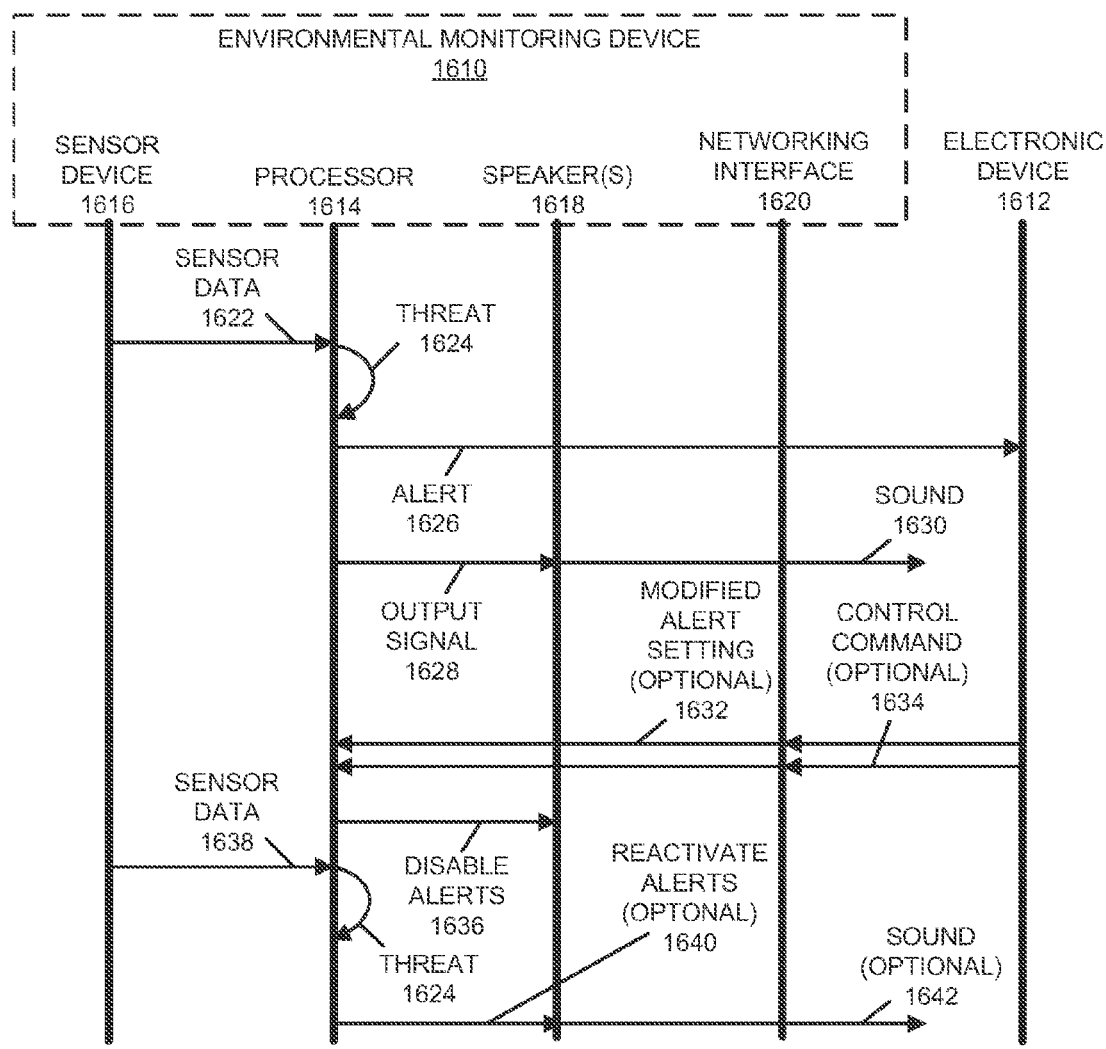
FIG. 16 is a drawing illustrating communication between an environmental monitoring device and an electronic device during the method of FIG. 15 in accordance with an embodiment of the present disclosure.

FIG. 16 presents a drawing illustrating communication between an environmental monitoring device 1610 and an electronic device 1612 during method 1500 (FIG. 15). During operation of environmental monitoring device 1610, processor 1614 may receive sensor data 1622 associated with a sensor device 1616 based on measurements of an environmental condition in an external environment. Then, if processor 1614 assesses the environmental condition indicates a threat 1624, processor 1614 may provide alert 1626 to electronic device 1612 based on the alert setting. In some embodiments, processor 1614 provides an output signal 1628 to one or more speakers 1618, which output an audible sound 1630 in the external environment.

Separately or additionally, networking subsystem 1620 may optionally receive, from electronic device 1612, modified alert setting 1632 and optionally control command 1634 in one or more packets or messages. In response, processor 1614 optionally disables alerts 1636.

Furthermore, processor 1614 may assess threat 1624 based on additional sensor data 1638 after receiving optional modified alert setting 1632, and may optionally reactivate the alerts 1640 if threat 1624 continues to increase. Alternatively or additionally, processor 1614 may revert from modified alert setting 1632 to the alert setting after a time interval. In response to either, the one or more speakers 1618 may optionally provide sound 1642.

Figure 17:
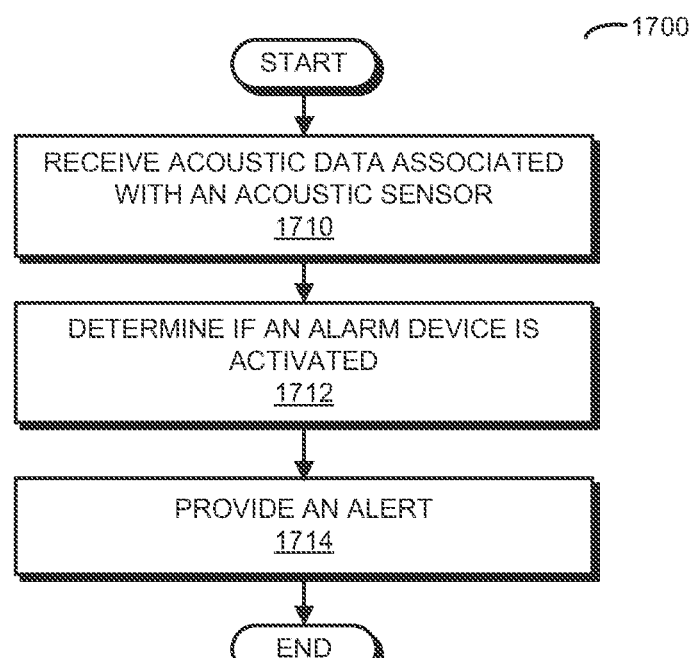
FIG. 17 is a flow diagram illustrating a method for providing an alert in accordance with an embodiment of the present disclosure.

In some embodiments, the environmental monitoring device determines if the alarm device is activated based, at least in part, on predefined (or predetermined) characterization of the external environment. This is shown in FIG. 17, which presents a flow diagram illustrating a method 1700 for providing an alert, which may be performed by a processor in the environmental monitoring device. For example, the processor may execute a program module that includes instructions for operations in method 1700. During operation, the processor may receive (or access) acoustic data (or analyzed acoustic data) associated with an acoustic sensor (operation 1710) based on measurements of sound in an external environment that includes the environmental monitoring device.

Then, the processor may determine if the alarm device, which is separate from the environmental monitoring device (and may not communicate with and/or may not have electrical coupling to the environmental monitoring device), is activated (operation 1712) based on the acoustic data and the predefined characterization of the external environment. For example, the predefined characterization may include a location of the alarm device in the external environment. This location may be specified by: an image of the external environment, a positioning system (such as GPS), a communication network (such as a cellular-telephone network), and/or an acoustic latency in the external environment (which can be used to determine distance). Moreover, the location of the alarm device may be relative to a location of the environmental monitoring device in the external environment. Furthermore, the predefined characterization may include an acoustic transfer function of the external environment proximate to the alarm device and the environmental monitoring device. This acoustic transfer function may be determined by the user using an application executing on the user's cellular telephone, which may output acoustic energy (such as a beacon or other signals) and measure echoes or an acoustic return as the user moves the cellular telephone through the external environment (and, thus, generates an acoustic map of the external environment). In conjunction with known locations of the cellular telephone, this information may allow the application to determine acoustic transfer function, which is then communicated to the environmental monitoring device. Moreover, using the acoustic transfer function, the processor may correct the acoustic data for distortion (such as amplitude loss and/or phase shifts) associated with the external environment, thereby allowing the processor to determine if the alarm device is activated (and, if there is more than one alarm device in the external environment, to determine which alarm device is activated).

Next, the processor may provide the alert (operation 1714) if the alarm device is activated. For example, the processor may provide an output or a control signal to one or more speakers that, in response, output an audible sound in the external environment. Alternatively or additionally, the processor may provide an output or a control signal to a networking subsystem, which wirelessly communicates the alert to another electronic device (such as the user's cellular telephone).

Figure 18:
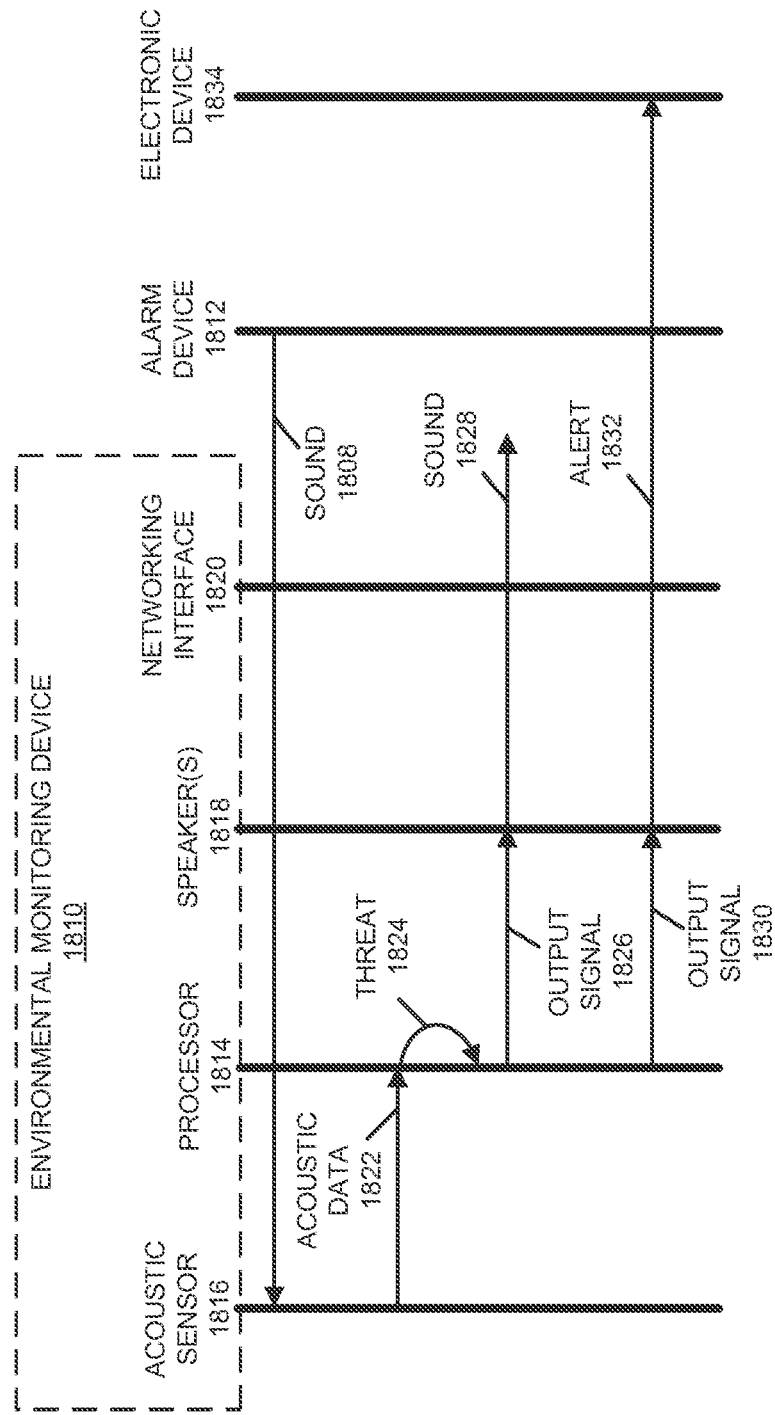
FIG. 18 is a drawing illustrating communication between an environmental monitoring device and an alarm device during the method of FIG. 17 in accordance with an embodiment of the present disclosure.

FIG. 18 presents a drawing illustrating communication between an environmental monitoring device 1810 and an alarm device 1812 during method 1700 (FIG. 17). During operation of environmental monitoring device 1810, processor 1814 may receive acoustic data 1822 associated with an acoustic sensor 1816 based on measurements of sound 1808 in an external environment from alarm device 1812.

Then, processor 1810 may determine if alarm device 1812 is activated 1824 based on acoustic data 1822 and the predefined characterization of the external environment.

Next, processor 1810 may provide the alert if alarm device 1812 is activated 1824. For example, processor 1810 may provide an output signal 1826 to one or more speakers 1818 that, in response, output an audible sound 1828 in the external environment. Alternatively or additionally, processor 1810 may provide an output signal 1830 to a networking subsystem 1820, which wirelessly communicates alert 1832 to another electronic device 1834.

Figure 19:
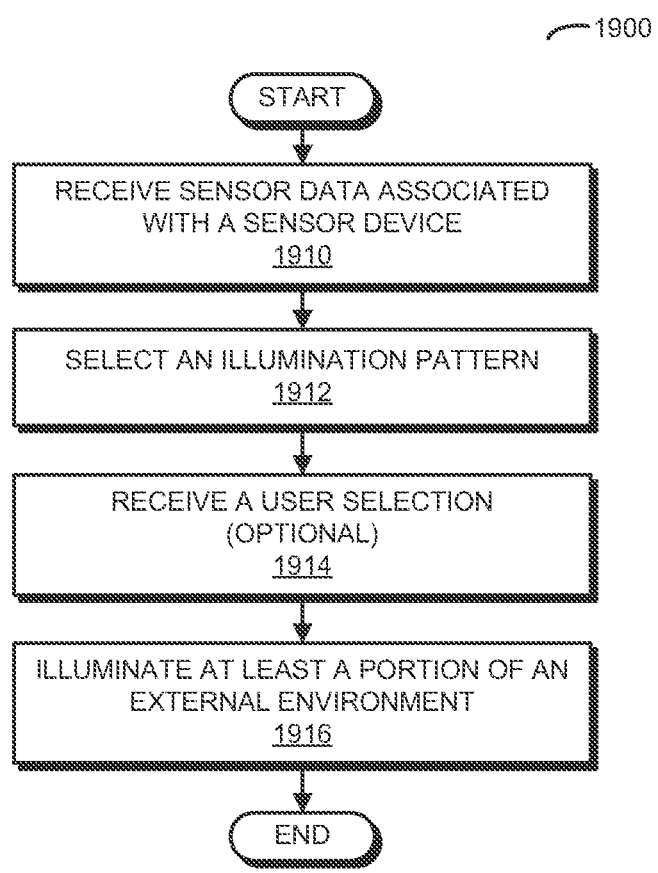
FIG. 19 is a flow diagram illustrating a method for illuminating at least a portion of an external environment in accordance with an embodiment of the present disclosure.

In some embodiments, the environmental monitoring device uses monitoring of one or more environmental conditions in an external environment to dynamically adapt an illumination pattern or lighting. This is shown in FIG. 19, which presents a flow diagram illustrating a method 1900 for illuminating at least a portion of an external environment, which may be performed by a processor in the environmental monitoring device. For example, the processor may execute a program module that includes instructions for operations in method 1900. During operation, the processor may receive (or access) sensor data (or analyzed sensor data) associated with a sensor device (operation 1910) based on measurements of an environmental condition in the external environment that includes the environmental monitoring device.

Then, the processor may select an illumination pattern (operation 1912) from a set of illumination patterns based on the sensor data, where the set of illumination patterns are associated with non-zero illumination of the external environment. Thus, in response to the sensor data, the processor may transition from one illumination pattern to another.

Alternatively or additionally, a user-input mechanism (such as a user interface) in the environmental monitoring device may optionally receive a user selection (operation 1914) that specifies a desired illumination pattern. In response to the received user selection, the processor may change the selected illumination pattern.

Furthermore, one or more light sources in the environmental monitoring device may illuminate at least a portion of the external environment (operation 1916) based on the selected illumination pattern.

For example, at least two of the illumination patterns in the set of illumination patterns may have: different spatial patterns in the external environment, different temporal patterns (or variations as a function of time, such as continuous, intermittent and/or modulated temporal patterns), different wavelengths of light, and/or different light intensities. Moreover, the environmental condition may include: opening of a door, an individual getting out of bed, an individual waking up, an individual (such as a baby) crying, an individual tossing and turning in bed (such as when the individual is having a nightmare), an individual shivering (which may be identified by an increasing amplitude of motion or vibration of the individual); and/or a change in health condition of an individual (such as a child coughing or having breathing trouble). Furthermore, at least one illumination pattern in the set of illumination patterns illuminates under a piece of furniture (such as a bed) in the external environment.

Thus, if a parent opens a door to a child's bedroom (which may constitute an environmental condition), the illumination pattern or lighting in the bedroom may change (e.g., the illumination pattern may transition from a 'nightlight' illuminating downward towards the floor to a narrow, low-intensity beam of light that shines on the child's bed). Similarly, if the child gets out of bed or wakes up (which also may constitute environmental conditions), the illumination pattern may change from the nightlight to a general illumination of the bedroom with a temporally slow increasing light intensity or to illuminating below the child's bed (so they can 'monster proof' the room). Alternatively, if the child is trying to fall to sleep (yet another environmental condition), the selected illumination pattern may attempt to assist or facilitate sleep. In particular, human dark or night vision is sensitive to visible wavelengths in the blue-portion of the spectrum. Consequently, the selected illumination pattern may include wavelengths of light in a predefined range, such as: wavelengths greater than approximately 530 nanometers or a predefined range that excludes wavelengths between approximately 460-480 nanometers. This predefined range may be implemented using one or more optical filters in or associated with the one or more light sources. More generally, the illumination pattern may be associated with: a light intensity or brightness, one or more wavelengths of light, a modulation pattern, etc. For example, the color of the illumination pattern at a given time may be specified by a hue and a saturation.

Figure 20:
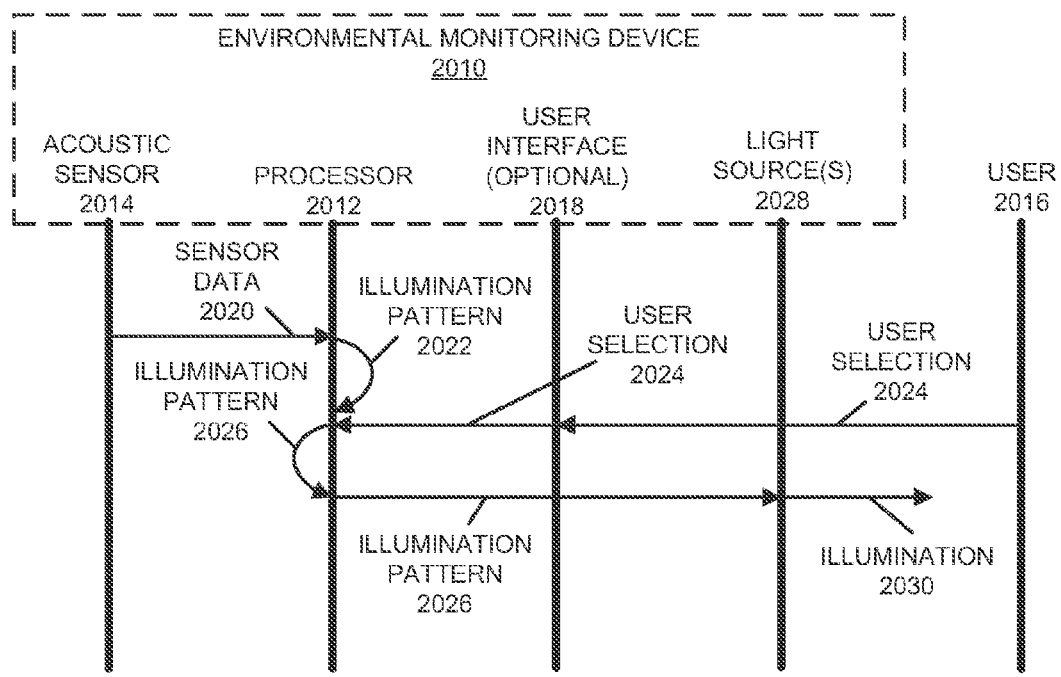
FIG. 20 is a drawing illustrating communication within an environmental monitoring device during the method of FIG. 19 in accordance with an embodiment of the present disclosure.

FIG. 20 presents a drawing illustrating communication within an environmental monitoring device 2010 during method 1900 (FIG. 19). During operation of environmental monitoring device 2010, processor 2012 may receive sensor data 2020 associated with a sensor device 2014 based on measurements of an environmental condition in the external environment.

Then, processor 2012 may select an illumination pattern 2022 from a set of illumination patterns based on sensor data 2020. Alternatively or additionally, a user 2016 may optionally provide a user selection 2024 that specifies a desired illumination pattern to user-input mechanism 2018, which is then provided to processor 2012. In response to the received user selection 2024, processor 2012 may change the selected illumination pattern 2026.

Furthermore, one or more light sources 2028 may provide illumination 2030 of at least a portion of the external environment based on the selected illumination pattern 2026.

In an exemplary embodiment, the environmental monitoring device of FIGS. 19 and 20 is used to provide an illumination pattern in the environment and sensor data based on a monitored environmental condition. In particular, home users (such as home owners, tenants, roommates, etc.) and commercial users (such as office users, industrial users, hospitality users, etc.) often require or prefer lighting on walkways and other areas of their home or business at night. In addition, users of both homes and businesses are often concerned about the environmental quality in the environments that they are living and working in. The environmental monitoring device may include a sensor device and may provide light (i.e., the illumination pattern) when desired by the user (e.g., at night), and may collect sensor data at any desired hour of the day, even when light may not be required or even desired by a user. The sensor data may be used by a user to assess the quality of their environment and determine if their environment is good and stable (e.g., the air quality has low levels of volatile organic compounds and allergens). Alternatively, the user can determine if their environment is potentially harmful or contains allergens that need to be addressed.

A light source in the environmental monitoring device may provide light (i.e., the illumination pattern) that can be for a variety of applications, such as: illuminating dark areas, signaling, display lighting, photography, etc. This light source may be: a light emitting diode, a plasma generation device, an incandescent light bulb, a light fixture (with or without an installed light source), a flashlight, a headlamp, a backlight for a screen, a photography flash device, a safety signal, an emergency light, etc. Moreover, the light source may emit light continuously, intermittently, modulated or in any other suitable visual pattern. In one embodiment, upon powering up the light source, the environmental monitoring device increases and decreases the brightness of the light source at a rate that simulates human breathing for 30 seconds. Additionally, the wavelength or color output by the light source may be: blue, white, yellow, or any other suitable hue, and can be in the ultraviolet spectrum, visible light spectrum, infrared spectrum, or any other suitable range of wavelengths. These wavelength ranges and/or colors may be chosen to serve specific functions. For example, in one embodiment the light output from the lighting source may be filtered to avoid wavelengths between 460 and 480 nm. Alternatively, the output light may be to only allow wavelengths of light greater than 530 nm. In other embodiments, the light source has low output in the wavelengths between 460 and 480 nm or below 530 nm. Note that wavelengths of light in the 460-480 nm range may be associated with dim-light melatonin onset, which may result in the depletion of melatonin levels. By filtering or choosing light sources with little or no output at wavelengths less than 530 nm, melatonin production in a child or an adult may not be disturbed during the night, and, therefore, their rest may be unaffected by the optical output from a nightlight. In another example, the color of the output light or of an illuminated environmental monitoring device may provide visual feedback or an indication of the monitored environmental condition (such as 'green' for ok, 'yellow' for concern, and 'red' for a warning, or 'blue' when there is a wireless connection to another electronic device and flashing 'red' when there is no wireless connection).

Figure 21:
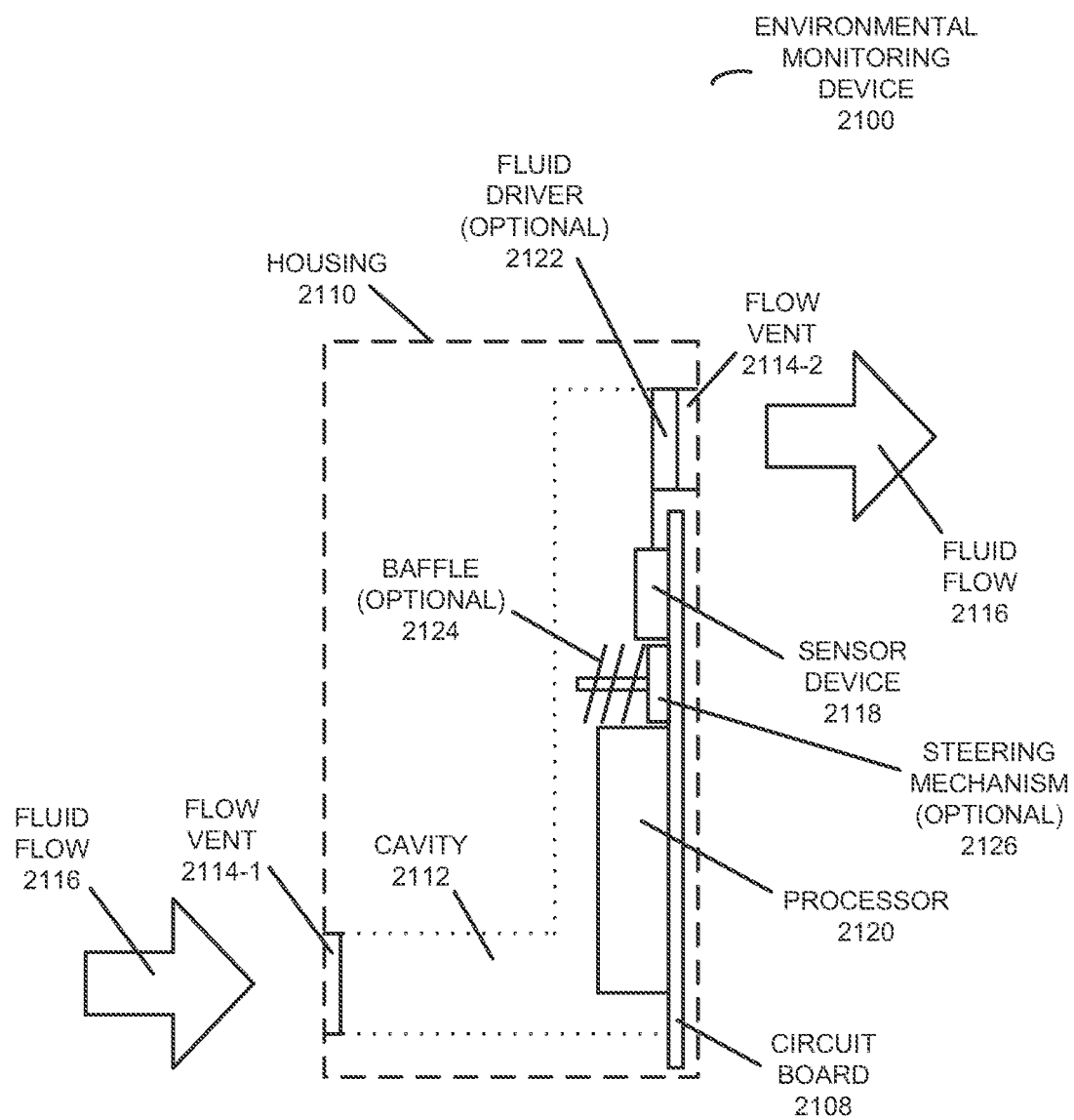
FIG. 21 is a block diagram illustrating a cross-sectional view of an environmental monitoring device in accordance with an embodiment of the present disclosure.

In some embodiments, the configuration and/or architecture of the environmental monitoring device may facilitate monitoring of one or more environmental conditions. This is shown in FIG. 21, which presents a block diagram illustrating a cross-sectional view of an environmental monitoring device 2100. This environmental monitoring device may include a housing 2110 having walls that define a cavity 2112 within housing 2110, and may include flow vents 2114 in at least one of the walls that, during operation of environmental monitoring device 2100, direct a fluid flow 2116 into and out of cavity 2112.

Moreover, environmental monitoring device 2100 may include a sensor device 2118 within cavity 2112, which provides sensor data based on measurements of an environmental condition in an external environment that includes environmental monitoring device 2100. Furthermore, environmental monitoring device 2100 may include a processor 2120 (and, more generally, an integrated circuit) within cavity 2112, which processes the sensor data. Note that fluid flow 2116 may be associated with operation of processor 2120, and processor 2120 may be positioned relative to sensor device 2118 so that fluid flow 2116 is directed over sensor device 2118 to facilitate the measurements. Note that sensor device 2118 and processor 2120 may be on a common circuit board 2108 or different circuit boards.

Fluid flow 2116 may include a convective fluid flow associated with heat generated during operation of processor 2120. Alternatively or additionally, environmental monitoring device 2100 may include an optional fluid driver 2122 and, during operation of processor 2120, optional fluid driver 2122 may force fluid flow 2116 into and out of cavity 2112 (and, thus, over sensor device 2118).

Additionally, sensor device 2118 may include a set of sensors, and environmental monitoring device 2100 may include an optional baffle 2124 that directs fluid flow 2116 over a selected sensor in the set of sensors. An orientation of optional baffle 2124 may be controlled by optional steering mechanism 2126 (based on a control signal provided by processor 2120) and/or manually by a user of environmental monitoring device 2100. For example, the optional steering mechanism 2126 may control optional baffle 2124 so that fluid flow 2116 is sequentially directed over different sensors in the set of sensors so that the sensors are polled, thereby facilitating temporal sampling of sensor data.

In an exemplary embodiment, the environmental monitoring device includes an air-intake mechanism that, during operation, allows air to enter into the environmental monitoring device, and to pass by or over a sensor device (such as a sensing array). The air-intake mechanism may be located on the front face, the side, or the back face of the environmental monitoring device. Moreover, the air-intake mechanism may be: a beveled groove, an opening, a series of perforations in the surface of environmental monitoring device, or another suitable type of ventilation. The environmental monitoring device may include a fan to help draw air into the environmental monitoring device. This fan may be: an axial fan, a centrifugal fan, a blower, a mechanical flap, a turbine, etc. For example, the front face of the environmental monitoring device 2100 may include a circular beveled groove through which air can enter and an axial fan located behind the groove that can draw air in. Alternatively, the front surface of the environmental monitoring device may have a square shape, a rectangular shape, a triangular shape, a pentagonal shape, hexagonal shape, or any other suitable polygon, and may include rounded corners with perforations that allow air to flow inside the environmental monitoring device.

Furthermore, an air-output mechanism may allow air that has entered the environmental monitoring device to exit. This air-output mechanism may include: a beveled groove, an exhaust port, a perforation, etc. The air-output mechanism may be located on the front face, the side, or the back face of the environmental monitoring device. For example, the back surface or face of the environmental monitoring device may include two exhaust ports through which air can exit a chassis or housing. Alternatively, the back surface of the environmental monitoring device may include a perforated square through which air can flow.

Additionally, the components in the environmental monitoring device may be arranged so heat generated during operation of one or more of the components heats air being taken in through the air-intake mechanism. For example, the environmental monitoring device may have a chamber (e.g., a convection chamber) through which the heated air rises and exits the environmental monitoring device via the air-output mechanism. In some embodiments, a heating element is included near the thermally radiating components to improve or increase the movement of air due to convection of heat from the thermally radiating components. In some embodiments, air enters through the air-intake mechanism and into a chamber, where it is heated by the thermally radiating components and/or the heating element. As the temperature of the air increases, the air can rise and circulate past the sensor device and out through the air-output mechanism.

Figure 22:
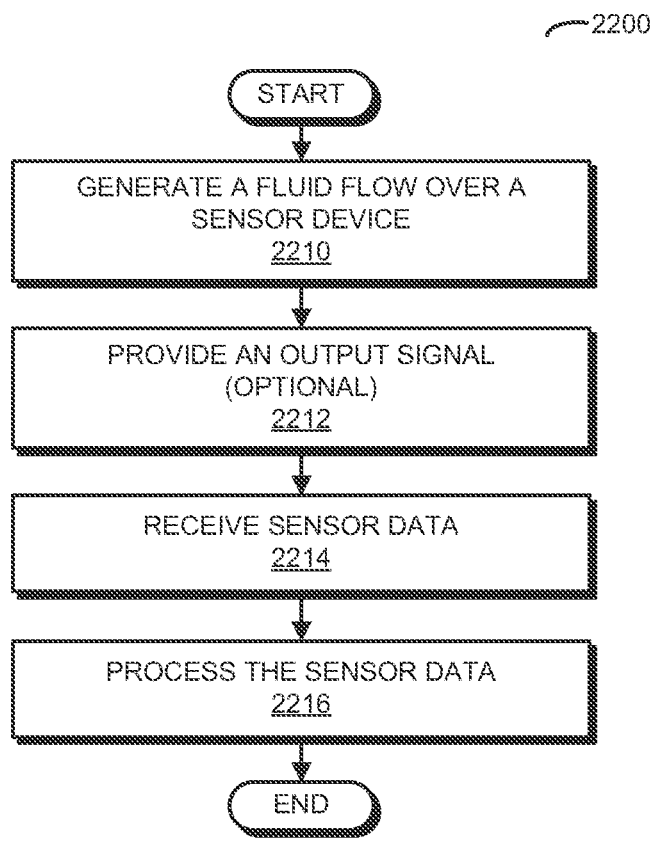
FIG. 22 is a flow diagram illustrating a method for processing sensor data in accordance with an embodiment of the present disclosure.

Operation of environmental monitoring device 2100 is further shown in FIG. 22, which presents a flow diagram illustrating a method 2200 for processing sensor data. This method may be performed by a processor in an environmental monitoring device 2100 in FIG. 21. In particular, during operation the processor may generate a fluid flow over a sensor device (operation 2210) in the environmental monitoring device, where the fluid flow is associated with operation of the processor, and where the processor is positioned relative to the sensor device so that the fluid flow is directed over the sensor device to facilitate measurements. For example, the fluid flow may include a convective fluid flow associated with heat generated during operation of the processor. Alternatively or additionally, the environmental monitoring device may include a fluid driver and, during operation of the processor, the fluid driver may force the fluid flow into and out of a cavity in the environmental monitoring device (and, thus, over the sensor device). Thus, the fluid flow may include an airflow and the fluid driver may include a fan, or the fluid flow may include a liquid flow and the fluid driver may include a pump.

In some embodiments, a steering mechanism (such as a stepper motor) optionally changes an orientation of a baffle in the environmental monitoring device based on a selected sensor. In particular, the processor may optionally provide an output signal (operation 2212) to the steering mechanism based on the selected sensor. Alternatively, an orientation of the baffle may change in response to an external force applied to the baffle (e.g., by a user of the environmental monitoring device).

Then, the processor may receive the sensor data (operation 2214) from the sensor device based on measurements of an environmental condition in the external environment that includes the environmental monitoring device. Note that the sensor device may include: an air-quality sensor, a particle counter, and/or a volatile-organic-compound sensor.

Next, the processor may process the sensor data (operation 2216). For example, the processor may: analyze the sensor data, filter the sensor data, compare the sensor data to data from other environmental monitoring devices, and/or perform another operation.

Figure 23:
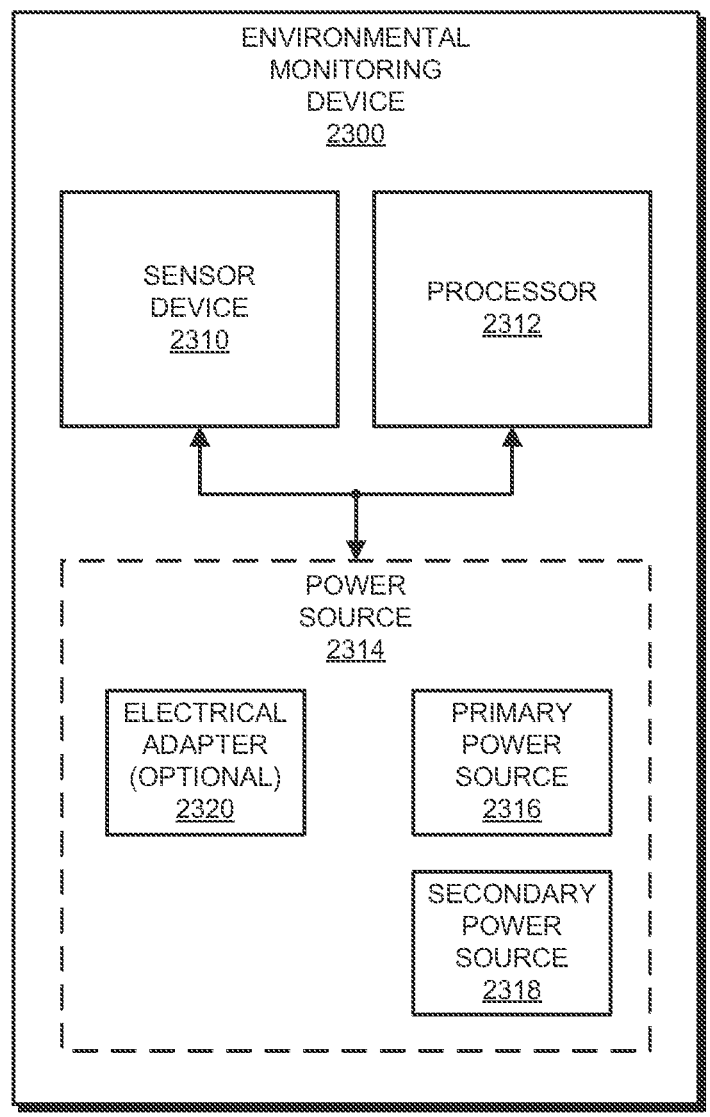
FIG. 23 is a block diagram illustrating an environmental monitoring device in accordance with an embodiment of the present disclosure.

In some embodiments, the environmental monitoring device includes a power source that ensures that at least a subset of the functionality of the environmental monitoring device is available over a time interval (such as 10 years). This is shown in FIG. 23, which presents a block diagram illustrating an environmental monitoring device 2300. In particular, environmental monitoring device 2300 may include a sensor device 2310 that provides sensor data based on measurements of environmental conditions in an external environment that includes environmental monitoring device 2300. Moreover, a processor 2312 may assess if the environmental conditions indicate an occurrence of at least one of a set of threats (which includes one or more threats). If yes, processor 2312 may provide a corresponding alert. Furthermore, environmental monitoring device 2300 may include a power source 2314 that includes a primary power source 2316 and a secondary power source 2318, where secondary power source 2318 may have at least a 10-year life and may power at least a subset of the functionality of environmental monitoring device 2300 (such as minimal or basic safety functionality) in the event primary power source 2316 fails. For example, secondary power source 2318 may include several batteries in parallel with each other. Furthermore, secondary power source 2318 may be sealed into or non-removable from environmental monitoring device 2300.

Note that the environmental conditions (and, thus, the set of threats) may include: presence of smoke, presence of carbon monoxide, fire, etc. Thus, sensor device 2310 may include a smoke detector that provides a smoke alert when smoke is present, and a carbon-monoxide detector that provides a carbon-monoxide alert when carbon monoxide is present. Moreover, the subset of the functionality may include providing an alert when smoke or carbon monoxide is present in the external environment. In this way, environmental monitoring device 2300 may be compliant with regulations that mandate that smoke detectors or carbon-monoxide detector have at least 10-year life.

In some embodiments, environmental monitoring device 2300 includes an optional electrical adaptor 2320 that can be electrically coupled to a power line. Alternatively or additionally, optional electrical adaptor 2320 may include an electrical connector that can be rotatably coupled to a light socket (as illustrated in FIG. 8).

Furthermore, primary power source 2316 may include a rechargeable battery. However, in other embodiments primary power source 2316 includes a non-rechargeable battery. Additionally, primary power source 2316 may be recharged via: a Universal Serial Bus connector and/or a cellular-telephone charger cable. For example, power sources 2316 and 2318 may be alternately or sequentially charged.

Figure 24:
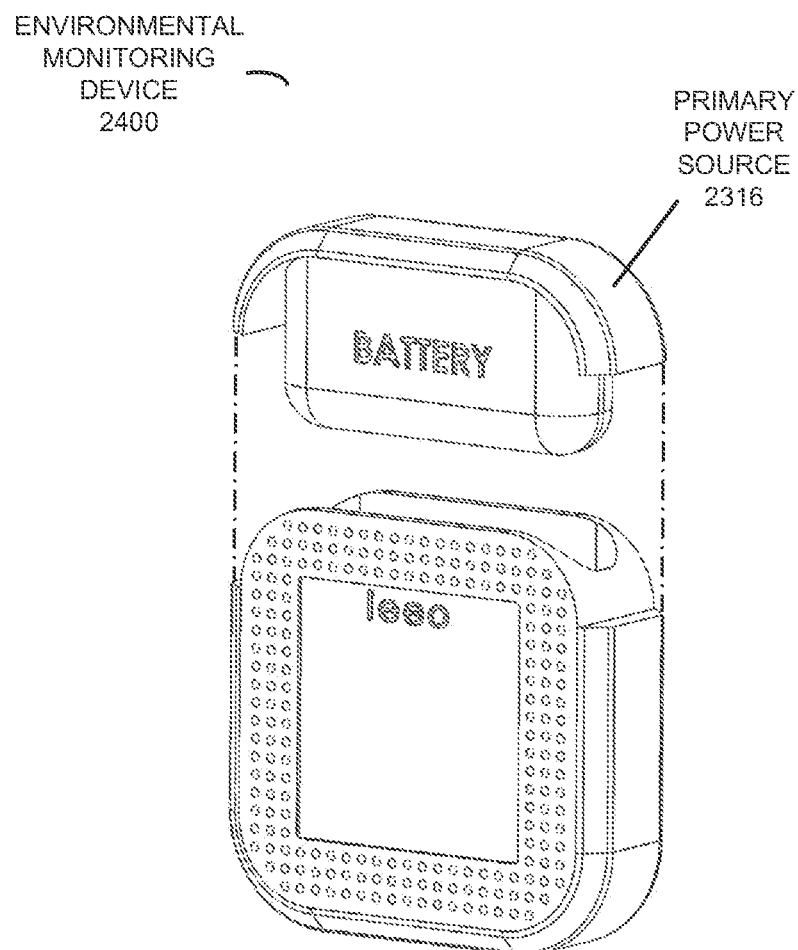
FIG. 24 is a drawing illustrating an environmental monitoring device in accordance with an embodiment of the present disclosure.

In some embodiments, primary power source 2316 is remateably mechanically and electrically coupled to environmental monitoring device 2300. For example, primary power source 2316 may be removed from and reattached to environmental monitoring device 2300 using: a broom handle and/or a magnet. In particular, a broom handle can push on primary power source 2316, which may cause primary power source 2316 to 'pop out' of environmental monitoring device 2300. In particular, primary power source 2316 may be removed from environmental monitoring device 2300 by a compressed spring when an external force is applied to undo a latch, and may be reattached to environmental monitoring device 2300 when an external force is applied to compress the spring and close the latch. (Note that this type of removable primary power source 2316 is sometimes referred to as a 'push-latched battery cartridge.') Alternatively, if a shaft with a magnet remateably magnetically couples or attaches to primary power source 2316, an external force (such as that supplied by a user pulling on the shaft) may be applied to primary power source 2316 to overcome friction, a force associated with bilateral protrusions or bumps in a housing surrounding primary power source 2316, and/or a force associated with a magnet in the housing. In these ways, primary power source 2316 may be removed from environmental monitoring device 2300 and/or subsequently reinserted or replaced. This is shown in FIG. 24, which presents a drawing illustrating environmental monitoring device 2400.

In an exemplary embodiment, one or more power sources can be removed or placed into the environmental monitoring device using assistance mechanism. The assistance mechanism may include: a ring, a hook, a magnetic strip, a rare earth magnet, a latch, a sticky material (such as double-sided tape), etc. For example, a power supply in the environmental monitoring device may include a battery that can be removed from a chassis or housing of the environmental monitoring device. This battery may be encased in a battery package or battery holder, which includes features (such as the assistance mechanism) that facilitate removal or placement of the battery. In some embodiments, an accessory-removal assistance device (such as a pole or broom handle) is used to facilitate easy removal of the battery package from a distance. In particular, the battery package may include a loop through which the accessory-removal assistance device can be hooked and pulled so that the battery package and the power supply separate from the main chassis of the environmental monitoring device. This loop may be embedded within the battery package and may protrude after a switch is depressed, at which point the battery package can be separated from the main chassis. Alternatively, a magnet may be embedded in the battery package so that it can be pulled away from the body of the chassis using another magnet on the accessory-removal assistance device.

Figure 25:
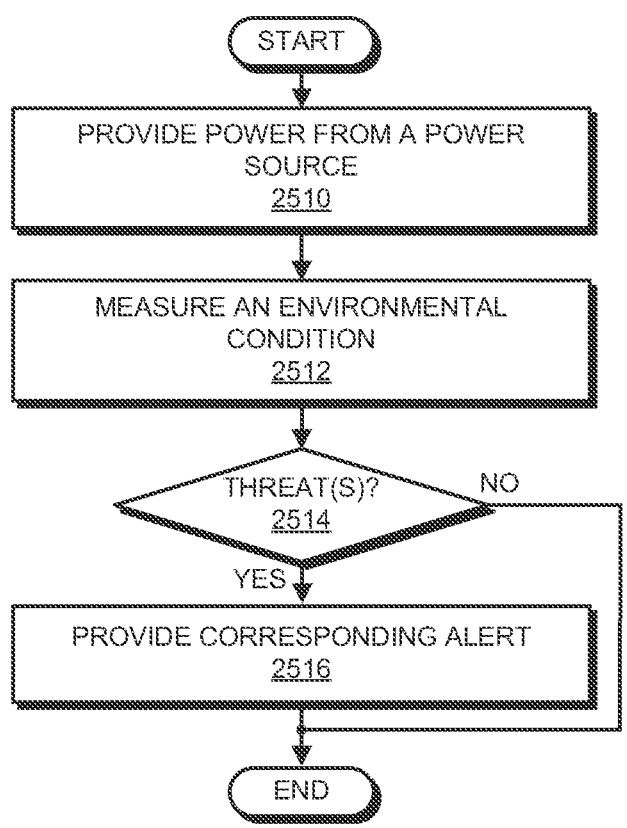
FIG. 25 is a flow diagram illustrating a method for providing an alert in accordance with an embodiment of the present disclosure.

Operation of environmental monitoring device 2300 (FIG. 23) is further shown in FIG. 25, which presents a flow diagram illustrating a method 2500 for providing an alert. In particular, during operation the environmental monitoring device may provide power from a power source (operation 2510) in the environmental monitoring device to a sensor device and a processor. The power source may include a primary power source and a secondary power source. Furthermore, the secondary power source may have at least the 10-year life and may power at least the subset of the functionality of the environmental monitoring device in the event the primary power source fails. Then, the sensor device may measure the environmental condition (operation 2512) in the external environment that includes the environmental monitoring device. Moreover, the processor may assess if the environmental conditions indicates the occurrence of at least the one of the set of threats (operation 2514) based on the measurements. For example, the set of threats may include one or more threats, such as the presence of carbon monoxide, the presence of smoke, fire, etc. If not, method 2500 may end. Otherwise, if at least the one of the set of threats is present, the processor may provide the corresponding alert (operation 2516).

Figure 26:
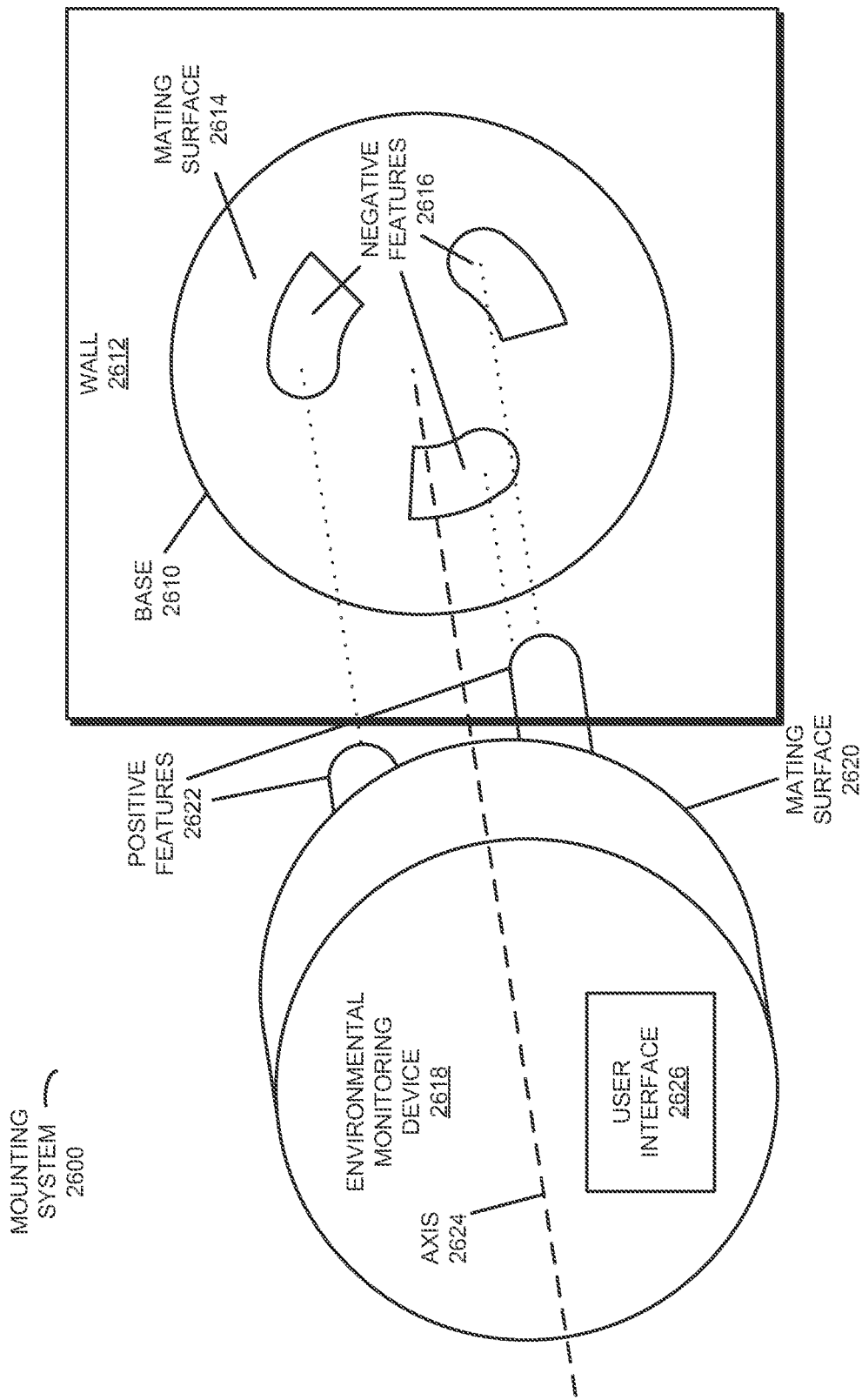
FIG. 26 is a block diagram illustrating a mounting system in accordance with an embodiment of the present disclosure.

In some embodiments, a mounting system is used to mount the environmental monitoring device on an external surface, such as a wall, ceiling, floor and/or a suitable surface in the external environment. This is shown in FIG. 26, which presents a block diagram illustrating a mounting system 2600. In particular, mounting system 2600 may include a base 2610 that can be rigidly mounted on an external surface (such as to a stud, a conduit box or a junction box in a wall 2612, using screws, nails, glue, sticky tack, or another suitable fastener). This base may have a mating surface 2614 with negative features 2616 (such as female receptors or holes) in recessed regions below mating surface 2614. Moreover, mounting system 2600 may include environmental monitoring device 2618 having a mating surface 2620 with positive features 2622 (such as male receptors or pins), which correspond to negative features 2616, protruding above mating surface 2620, where mating surface 2620 faces mating surface 2614, and where positive features 2622 can be remateably coupled to negative features 2616. In some embodiments, the remateable coupling involves the use of a tool, such as a wrench or an Allen or hex key that is used to release a locking mechanism (e.g., a lock nut). (However, in other embodiments a tool is not used.) Note that the remateable coupling may involve: pushing positive features 2622 into negative features 2616; rotating environmental monitoring device 2618 relative to base 2610 about an axis 2624 perpendicular to mating surface 2614 so that positive features 2622 interlock with negative features 2616; and applying a torque about axis 2624 to snap positive features 2622 into a lock position in negative features 2616.

In some embodiments, base 2610 can be electrically coupled to an external power line. Thus, the remateable coupling may include mechanical coupling and/or electrical coupling.

Furthermore, positive features 2622 can be remateably decoupled from negative features 2616. This remateable decoupling may involve: applying a torque to environmental monitoring device 2618 relative to base 2610 about axis 2624 in an opposite sense to the torque used to remateably couple positive features 2622 and negative features 2616 until positive features 2622 snap out of the lock position; rotating environmental monitoring device 2618 relative to base 2610 about axis 2624 in an opposite sense to the rotation used to remateably couple positive features 2622 and negative features 2616; and pulling positive features 2622 out of negative features 2616.

To prevent or deter theft of environmental monitoring device 2618, in some embodiments environmental monitoring device 2618 is registered as belonging at a particular location, and can only be moved if environmental monitoring device 2618 receives a security code. For example, the security code may be supplied wirelessly from an electronic device (such as a cellular telephone) and/or may be entered into a user interface 2626. Moreover, a sensor device in environmental monitoring device 2618 may monitor a spatial parameter of environmental monitoring device 2618. If a change in the spatial parameter relative to base 2610 exceeds a threshold value (such as a relative change in the spatial parameter of 10 or 25%) without environmental monitoring device 2618 first receiving the security code, environmental monitoring device 2618 may provide an alert (such as outputting an audible alarm or wirelessly communicating an alert message to the electronic device) and/or may disable environmental monitoring device 2618. An external system adapted to receive data from environmental monitoring device 2618 may provide an alert if a data connection or data transmission is interrupted or ceased in this way. Note that the spatial parameter may include a location of environmental monitoring device 2618, a velocity of environmental monitoring device 2618 and/or an acceleration of environmental monitoring device 2618. Thus, the spatial parameter may include: a derivative of the location, an integration of the velocity and/or a double integration of the acceleration.

Figure 27:
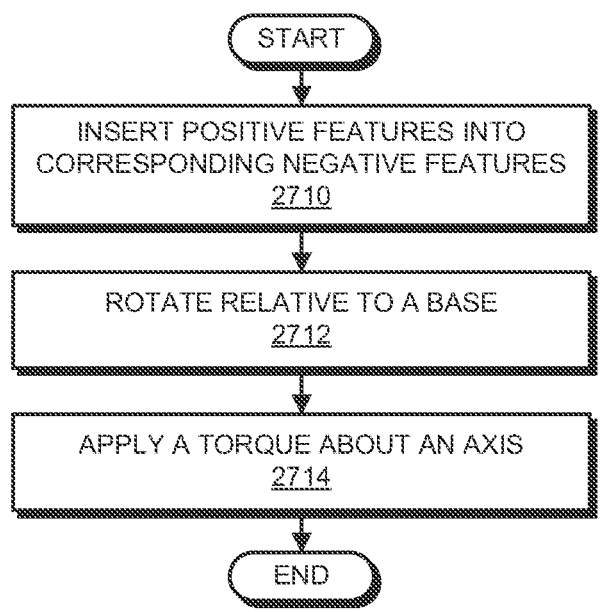
FIG. 27 is a flow diagram illustrating a method for mounting the environmental monitoring device of FIG. 26 in accordance with an embodiment of the present disclosure.

FIG. 27 presents a flow diagram illustrating a method 2700 for mounting an environmental monitoring device, such as environmental monitoring device 2618 (FIG. 26). During this method, positive features, protruding above a first mating surface of an environmental monitoring device, may be inserted into corresponding negative features (operation 2710) on a second mating surface of a base. Then, the environmental monitoring device may be rotated relative to the base (operation 2712) about an axis perpendicular to the second mating surface so that the positive features interlock with the negative features. Next, a torque may be applied about the axis (operation 2714) to snap the positive features into a lock position in the negative features.

Figure 28:
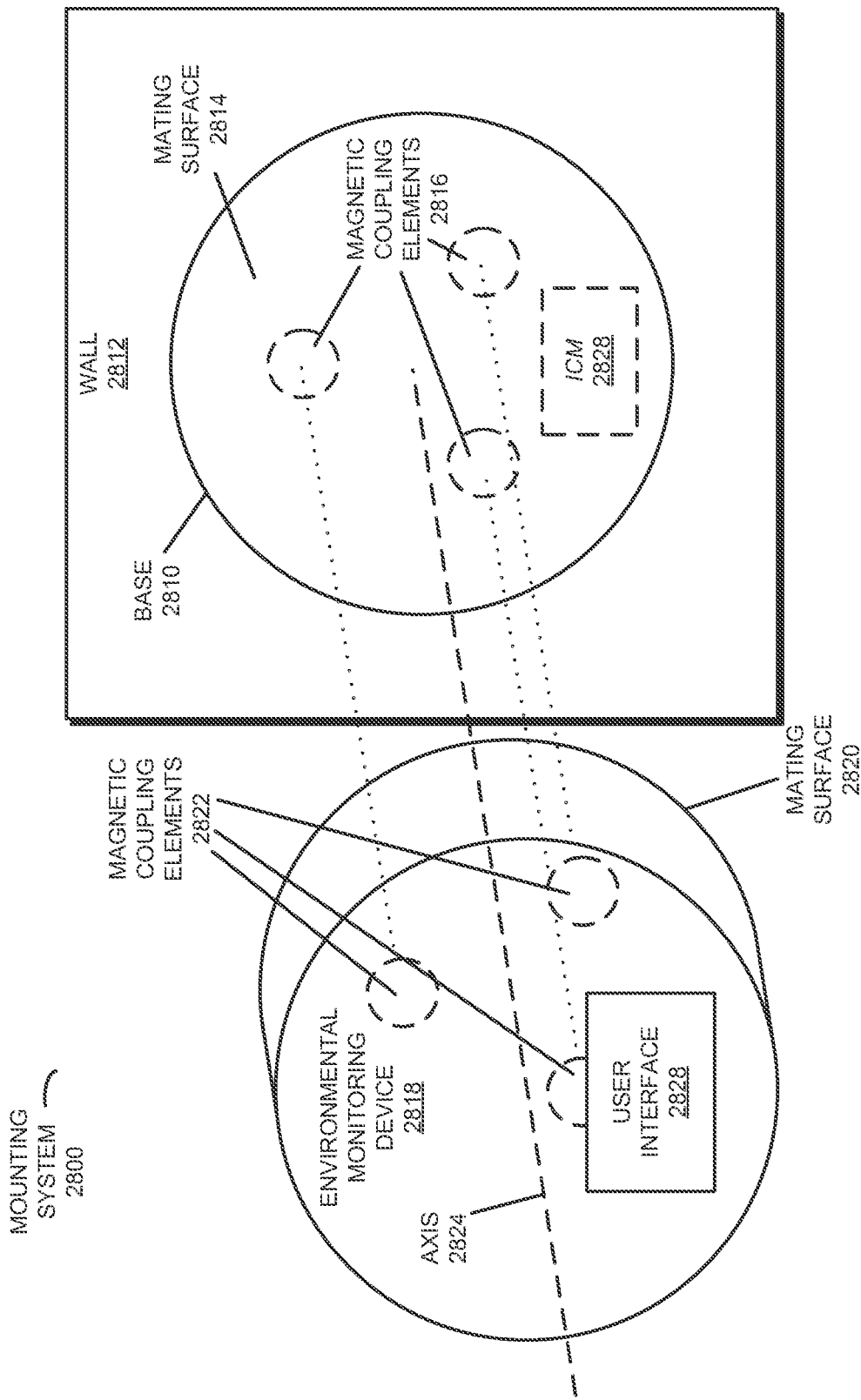
FIG. 28 is a block diagram illustrating a mounting system in accordance with an embodiment of the present disclosure.

A variation on the mounting system is shown in FIG. 28, which presents a block diagram illustrating a mounting system 2800. In particular, this mounting system may include a base 2810 that can be rigidly mounted on an external surface (such as to a stud, a conduit box or a junction box in a wall 2812 having a thickness). This base may have a mating surface 2814 that includes magnetic coupling elements 2816 (e.g., three permanent magnets or electromagnets in a triangular arrangement). Moreover, mounting system 2800 may include an environmental monitoring device 2818 having a mating surface 2820 with magnet coupling elements 2822 (e.g., three permanent magnets or electromagnets in a triangular arrangement), where the mating surface 2820 faces mating surface 2814, and where magnet coupling elements 2816 can be remateably coupled to magnet coupling elements 2822 (e.g., via a magnetic field between magnetic coupling elements 2816 and 2822). In some embodiments, the remateable coupling involves the use of a tool, such as a wrench or an Allen or hex key that is used to release a locking mechanism (e.g., a lock nut). (However, in other embodiments a tool is not used.) The remateable coupling may involve: positioning mating surface 2820 within a predefined distance (such as 2-3 cm or more than the thickness of wall 2812, which may be ⅝ or ¾ in) from mating surface 2814 along an axis 2824 perpendicular to mating surface 2814; and positioning magnet coupling elements 2816 substantially overlapping (such as an overlap of more than 50%) magnet coupling elements 2822.

Moreover, base 2810 can be electrically coupled to an external power line. Thus, the remateable coupling may include mechanical coupling and/or electrical coupling. Furthermore, base 2810 may include an inductive charging mechanism (ICM) 2826 that inductively charges a power source or supply (not shown) in the environmental monitoring device 2818 when magnet coupling elements 2816 are remateably coupled to magnetic coupling elements 2822. Alternatively or additionally, inductive charging mechanism 2826 may inductively provide power to environmental monitoring device 2818 when magnet coupling elements 2816 are remateably coupled to magnetic coupling elements 2822.

In some embodiments, magnetic coupling elements 2816 can be remateably decoupled from magnetic coupling elements 2822. This remateable decoupling may involve pulling on environmental monitoring device 2818 along axis 2824 until a coupling force associated with magnetic coupling elements 2816 and 2822 is exceeded.

To prevent or deter theft of environmental monitoring device 2818, in some embodiments environmental monitoring device 2818 is registered as belonging at a particular location, and can only be moved if environmental monitoring device 2818 receives a security code. For example, the security code may be supplied wirelessly from an electronic device (such as a cellular telephone) and/or may be entered into a user interface 2828. Moreover, a sensor device in environmental monitoring device 2818 may monitor a spatial parameter of environmental monitoring device 2818. If a change in the spatial parameter relative to base 2810 exceeds a threshold value (such as a relative change in the spatial parameter of 10 or 25%) without environmental monitoring device 2818 first receiving the security code, environmental monitoring device 2818 may provide an alert (such as outputting an audible alarm or wirelessly communicating an alert message to the electronic device) and/or may disable environmental monitoring device 2818. An external system adapted to receive data from environmental monitoring device 2818 may provide an alert if a data connection or data transmission is interrupted or ceased in this way. Note that the spatial parameter may include a location of environmental monitoring device 2818, a velocity of environmental monitoring device 2818 and/or an acceleration of environmental monitoring device 2818. Thus, the spatial parameter may include: a derivative of the location, an integration of the velocity and/or a double integration of the acceleration.

Figure 29:
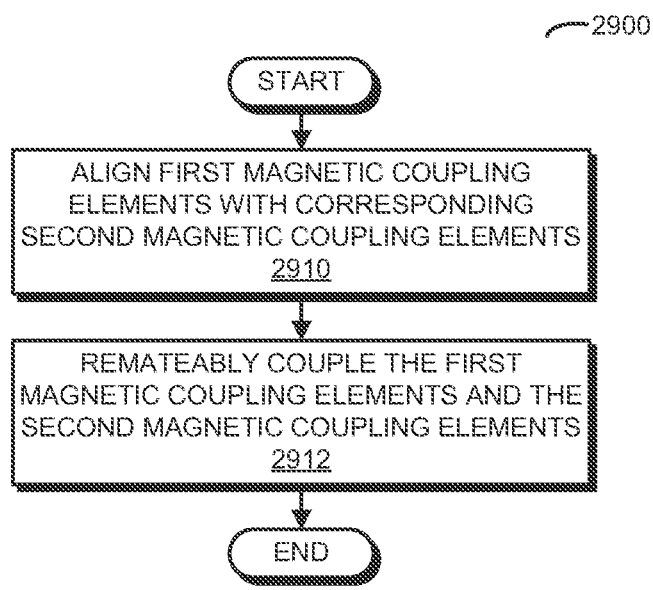
FIG. 29 is a flow diagram illustrating a method for mounting the environmental monitoring device of FIG. 28 in accordance with an embodiment of the present disclosure.

FIG. 29 presents a flow diagram illustrating a method 2900 for mounting an environmental monitoring device, such as environmental monitoring device 2818 (FIG. 28). During this method, first magnetic coupling elements, on a first mating surface of an environmental monitoring device, may be aligned with corresponding second magnetic coupling elements (operation 2910) on a second surface of a base. Then, the first magnetic coupling elements and the second magnetic coupling elements may be remateably coupled (operation 2912) by a magnetic field between the first magnetic coupling elements and the second magnetic coupling elements. For example, the magnetic field may induce an electric field that results in a force of attraction between the environmental monitoring device and the base.

While positive and negative features and magnetic coupling elements were used as illustrations in the preceding embodiments, in other embodiments the environmental monitoring device is remateably coupled to the base using: hooks, adhesive, screws, snaps, Velcro, and/or another suitable connector.

In some embodiments of one or more of the preceding methods, there may be additional or fewer operations. Furthermore, the order of the operations may be changed, and/or two or more operations may be combined into a single operation. For example, in FIG. 19, instead of or in addition to changing the illumination pattern, the environmental monitoring device may change an operating mode in response to image data and/or sensor data. In addition, in some of the preceding embodiments there are fewer components, more components, a position of a component is changed and/or two or more components are combined.

A wide variety of materials may be used to fabricate the environmental monitoring device (and, in particular, the housing or chassis of the environmental monitoring device), including: organic materials (such as plastic, polyethylene, wood, etc.), inorganic materials (such as a metal), glass, concrete, rubber, a semiconductor, a fabric, etc. Moreover, the housing or chassis may be transparent or opaque.

In the preceding description, we refer to 'some embodiments.' Note that 'some embodiments' describes a subset of all of the possible embodiments, but does not always specify the same subset of embodiments.

The foregoing description is intended to enable any person skilled in the art to make and use the disclosure, and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown, but is to be accorded the widest scope consistent with the principles and features disclosed herein.

What is claimed is:

1. An environmental monitoring device, comprising:
   a housing having walls that define a cavity within the housing;
   flow vents in at least one of the walls configured to direct a fluid flow into and out of the cavity during operation of the environmental monitoring device;
   a sensor mechanism, within the cavity, configured to provide sensor data based on measurements of an environmental condition in an external environment that includes the environmental monitoring device, wherein the sensor mechanism includes a set of sensors;
   a baffle configured to direct the fluid flow over a selected sensor in the set of sensors, wherein an orientation of the baffle is configured to change in response to an external force applied to the baffle; and
   a processor, within the cavity and electrically coupled to the sensor mechanism, configured to process the sensor data, wherein the fluid flow is associated with operation of the processor; and
   wherein the processor is positioned relative to the sensor mechanism so that the fluid flow is directed over the sensor mechanism to facilitate the measurements.

2. The environmental monitoring device of claim 1, wherein the fluid flow includes a convective fluid flow associated with heat generated during operation of the processor.

3. The environmental monitoring device of claim 1, wherein the environmental monitoring device further comprises a fluid driver; and
   wherein, during operation of the processor, the fluid driver forces the fluid flow into and out of the cavity.

4. The environmental monitoring device of claim 3, wherein the fluid flow includes an airflow and the fluid driver includes a fan.

5. The environmental monitoring device of claim 3, wherein the fluid flow includes a liquid flow and the fluid driver includes a pump.

6. The environmental monitoring device of claim 1, wherein the fluid flow includes one of: an airflow, and a liquid flow.

7. The environmental monitoring device of claim 1, wherein the sensor mechanism includes one of: an air-quality sensor, a particle counter, and a volatile-organic-compound sensor.

8. The environmental monitoring device of claim 1, wherein the environmental monitoring device further includes a steering mechanism configured to change an orientation of the baffle based on the selected sensor.

9. The environmental monitoring device of claim 8, wherein a control mechanism is electrically coupled to the steering mechanism and is configured to provide an output signal to the steering mechanism based on the selected sensor; and wherein the output signal specifies the selected sensor.

10. An environmental monitoring device, comprising:

a housing having walls that define a cavity within the housing;

flow vents in at least one of the walls configured to direct an airflow into and out of the cavity;

a sensor mechanism, within the cavity, configured to provide sensor data based on measurements of an environmental condition in an external environment that includes the environmental monitoring device, wherein the sensor mechanism includes a set of sensors;

a baffle configured to direct the fluid flow over a selected sensor in the set of sensors wherein an orientation of the baffle is configured to change in response to an external force applied to the baffle; and a processor, within the cavity and electrically coupled to the sensor mechanism, configured to process the sensor data, wherein the airflow includes a convective airflow associated with heat generated during operation of the processor; and wherein the processor is positioned relative to the sensor mechanism so that the airflow is directed over the sensor mechanism to facilitate the measurements.

11. The environmental monitoring device of claim 10, wherein the sensor mechanism includes one of: an air-quality sensor, a particle counter, and a volatile-organic-compound sensor.

12. A processor-implemented method for processing sensor data, wherein the method comprises:

generating a fluid flow over a sensor mechanism in an environmental monitoring device, wherein the fluid flow is associated with operation of the processor, and wherein the processor is positioned relative to the sensor mechanism so that the fluid flow is directed over the sensor mechanism to facilitate measurements;

receiving sensor data from the sensor mechanism based on the measurements of the environmental condition in an external environment that includes the environmental monitoring device, wherein the sensor mechanism includes a set of sensors;

changing an orientation of a baffle that directs the fluid flow over a selected sensor in the set of sensors by applying an external force to the baffle; and using the processor, processing the sensor data.

13. The method of claim 12, wherein the fluid flow includes a convective fluid flow associated with heat generated during operation of the processor.

14. The method of claim 12, wherein the environmental monitoring device further comprises a fluid driver; and wherein, during operation of the processor, the fluid driver forces the fluid flow over the processor and the sensor mechanism.

15. The method of claim 12, wherein the fluid flow includes one of: an air flow, and a liquid flow.

16. The method of claim 12, wherein the sensor mechanism includes a set of sensors; and wherein the method further includes directing the fluid flow over a selected sensor in the set of sensors using a baffle in the environmental monitoring device.

17. An environmental monitoring device, comprising:

a housing having walls that define a cavity within the housing;

flow vents in at least one of the walls configured to direct a fluid flow into and out of the cavity during operation of the environmental monitoring device;

a sensor mechanism, within the cavity, configured to provide sensor data based on measurements of an environmental condition in an external environment that includes the environmental monitoring device, wherein the sensor mechanism includes a set of sensors;

a baffle configured to direct the airflow over a selected sensor in the set of sensors;

a steering mechanism configured to change an orientation of the baffle based on the selected sensor;

a control mechanism, electrically coupled to the steering mechanism, configured to provide an output signal to the steering mechanism based on the selected sensor, wherein the output signal specifies the selected sensor; and a processor, within the cavity and electrically coupled to the sensor mechanism, configured to process the sensor data, wherein the fluid flow is associated with operation of the processor; and wherein the processor is positioned relative to the sensor mechanism so that the fluid flow is directed over the sensor mechanism to facilitate the measurements.

18. An environmental monitoring device, comprising:

a housing having walls that define a cavity within the housing;

flow vents in at least one of the walls configured to direct an airflow into and out of the cavity;

a sensor mechanism, within the cavity, configured to provide sensor data based on measurements of an environmental condition in an external environment that includes the environmental monitoring device, wherein the sensor mechanism includes a set of sensors;

a baffle configured to direct the airflow over a selected sensor in the set of sensors;

a steering mechanism configured to change an orientation of the baffle based on the selected sensor;

a control mechanism, electrically coupled to the steering mechanism, configured to provide an output signal to the steering mechanism based on the selected sensor, wherein the output signal specifies the selected sensor; and a processor, within the cavity and electrically coupled to the sensor mechanism, configured to process the sensor data, wherein the airflow includes a convective airflow associated with heat generated during operation of the processor; and wherein the processor is positioned relative to the sensor mechanism so that the airflow is directed over the sensor mechanism to facilitate the measurements.

19. A processor-implemented method for processing sensor data, wherein the method comprises:

generating a fluid flow over a sensor mechanism in an environmental monitoring device, wherein the fluid flow is associated with operation of the processor, and wherein the processor is positioned relative to the sensor mechanism so that the fluid flow is directed over the sensor mechanism to facilitate measurements;

receiving sensor data from the sensor mechanism based on the measurements of the environmental condition in an external environment that includes the environmental monitoring device, wherein the sensor mechanism includes a set of sensors;

changing an orientation of a baffle that directs the fluid flow over a selected sensor in the set of sensors using a steering mechanism based on an output signal from a control mechanism that specifies the selected sensor; and using the processor, processing the sensor data.

* * * * *